(12) United States Patent
Farmer et al.

(10) Patent No.: US 8,486,989 B2
(45) Date of Patent: Jul. 16, 2013

(54) INHIBITORS OF SERINE PROTEASES, PARTICULARLY HCV NS3-NS4A PROTEASE

(75) Inventors: Luc J. Farmer, Foxboro, MA (US); Robert B. Perni, Marlborough, MA (US); Janos Pitlik, Westborough, MA (US); John H. van Drie, Jr., Andover, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1237 days.

(21) Appl. No.: 11/805,085

(22) Filed: May 22, 2007

(65) Prior Publication Data
US 2008/0045480 A1 Feb. 21, 2008

Related U.S. Application Data

(62) Division of application No. 10/280,940, filed on Oct. 24, 2002, now Pat. No. 7,241,796.

(60) Provisional application No. 60/343,862, filed on Oct. 24, 2001.

(51) Int. Cl.
| A61K 31/40 | (2006.01) |
| A61K 51/00 | (2006.01) |
| A01N 43/38 | (2006.01) |
| C07D 209/56 | (2006.01) |
| C07D 487/00 | (2006.01) |
| C07D 491/00 | (2006.01) |

(52) U.S. Cl.
USPC ............. 514/411; 514/410; 514/19; 548/424; 548/429; 548/430; 424/1.69

(58) Field of Classification Search
None
See application file for complete search history.

(56) References Cited

U.S. PATENT DOCUMENTS

| 6,909,000 B2 * | 6/2005 | Farmer et al. ................. 544/406 |
| 7,241,796 B2 * | 7/2007 | Farmer et al. ................. 514/411 |
| 7,273,885 B2 * | 9/2007 | Pitlik et al. ..................... 514/414 |
| 2005/0197299 A1 * | 9/2005 | Babine et al. .................... 514/18 |
| 2010/0137583 A1 * | 6/2010 | Babine et al. ................. 544/101 |

FOREIGN PATENT DOCUMENTS

| WO | 97/43310 | 11/1997 |
| WO | 98/17679 | 4/1998 |
| WO | WO 98/17679 | * 4/1998 |
| WO | 98/46630 | 10/1998 |
| WO | 99/07733 | 2/1999 |
| WO | 99/07734 | 2/1999 |
| WO | WO 99/07733 | * 2/1999 |
| WO | WO 99/07734 | * 2/1999 |
| WO | 99/50230 | 10/1999 |
| WO | WO 99/50230 | * 10/1999 |
| WO | 99/64442 | 12/1999 |
| WO | 00/09543 | 2/2000 |
| WO | 00/94558 | 2/2000 |
| WO | WO 00/09543 | * 2/2000 |
| WO | WO 00/09558 | * 2/2000 |
| WO | 01/74768 | 10/2001 |
| WO | 02/08244 | 1/2002 |

OTHER PUBLICATIONS

O. Weiland, "Interferon Therapy in Chronic Hepatitis C Virus Infection", FEMS Microbiol. Rev., 14, pp. 279-288 (1994) (as cited in present specification, para 9).*
LaPlante, S.R., et al., "NMR Line-Broadening and Transferred NOESY as a Medicinal Chemistry Tool for Studying Inhibitors of the Hepatitis C Virus NS3 Protease Domain," Bioorgan. & Med. Chem. Ltrs, 10:2271-2274 (2000).
Llinas-Brunet, M., et al., "Highly Potent and Selective Peptide-Based Inhibitors of the Hepatitis C Virus Serine Protease: Towards Smaller Inhibitors," Bioorgan. & Med. Chem Ltrs., 10:2267-2270 (2000).
Dunsdon, R.M., et al., "Solid Phase Synthesis of Aminoboronic Acids: Potent Inhibitors of the Hepatitis C Virus NS3 Proteinase," Bioorg. & Med. Chem. Ltrs., 10:1577-1579 (2000).
Han, W., et al., "α-Ketoamides, α-Ketoesters and α-Diketones as HCV NS3 Protease Inhibitors," Bioorgan. & Med. Chem. Ltrs., 10:711-713 (2000).
Llinas-Brunet, M., et al., "Peptide-Based Inhibitors of the Hepatitis C Virus Serine Protease," Bioorgan. & Med. Chem. Ltrs., 8:1713-1718 (1988).

* cited by examiner

*Primary Examiner* — Maury Audet
(74) *Attorney, Agent, or Firm* — Lisa A. Dixon; Susan C. Kelly

(57) ABSTRACT

The present invention relates to peptidomimetic compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

34 Claims, No Drawings

INHIBITORS OF SERINE PROTEASES, PARTICULARLY HCV NS3-NS4A PROTEASE

RELATED APPLICATIONS

This application is a divisional application of Ser. No. 10/280,940, filed Oct. 24, 2002, now U.S. Pat. No. 7,241,796, which claims the benefit of U.S. Provisional Patent Application 60/343,862 filed Oct. 24, 2001. The entire contents of each of the above applications are incorporated herein by reference.

TECHNICAL FIELD OF THE INVENTION

The present invention relates to peptidomimetic compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et al., "Expression and Identification of Hepatitis C Virus Polyprotein Cleavage Products," *J. Virol.*, 67, pp. 1385-1395 (1993); L. Tomei et al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Several potential HCV protease inhibitors have been described in the prior art [PCT publication Nos. WO 00/09558, WO 00/09543, WO 99/64442, WO 99/07733, WO 99/07734, WO 99/50230, WO 98/46630, WO 98/17679 and WO 97/43310, U.S. Pat. No. 5,990,276, M. Llinas-Brunet et al., *Bioorg. Med. Chem. Lett.*, 8, pp. 1713-18 (1998); W. Han et al., *Bioorg. Med. Chem. Lett.*, 10, 711-13 (2000); R. Dunsdon et al., *Bioorg. Med. Chem. Lett.*, 10, pp. 1571-79 (2000); M. Llinas-Brunet et al., *Bioorg. Med. Chem. Lett.*, 10, pp. 2267-70 (2000); and S. LaPlante et al., Bioorg. Med. Chem. Lett., 10, pp. 2271-74 (2000)]. Unfortunately, there are no serine protease inhibitors available currently as anti-HCV agents.

Furthermore, the current understanding of HCV has not led to any other satisfactory anti-HCV agents or treatments. The only established therapy for HCV disease is interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and induce long term remission in only a fraction (~25%) of cases [O. Weiland, "Interferon Therapy in Chronic Hepatitis C Virus Infection", *FEMS Microbiol.*

Rev., 14, pp. 279-288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides a compound of formula (I):

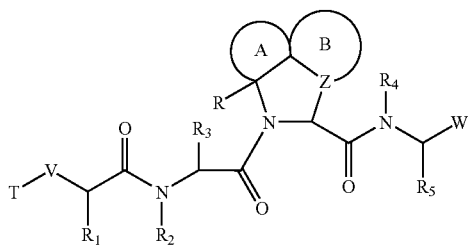

(I)

wherein:
ring A is a carbocyclic or heterocyclic ring, wherein ring A is optionally fused to a carbocyclic, heterocyclic or heteroaryl ring;
wherein ring A has up to 3 substituents selected independently from J;
ring B is a carbocyclic or heterocyclic ring, wherein ring B is optionally fused to a carbocyclic, heterocyclic or heteroaryl ring;
wherein ring B has up to 3 substituents selected independently from J;
J is halogen, —OR', —NO$_2$, —CF$_3$, —OCF$_3$, —R', oxo, —O-benzyl, —O-phenyl, 1,2-methylenedioxy, 1,2-ethylenedioxy, —N(R')$_2$, —SR', —SOR', —SO$_2$R', —C(O)R', —COOR' or —CON(R')$_2$, —OC(O)R' wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
$R_1$ and $R_3$ are independently:
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, or SO$_2$ in a chemically stable arrangement;
$R_2$ and $R_4$ are independently
hydrogen,
(C1-C12)-aliphatic,
(C3-C10)-cycloalkyl-(C1-C12)-aliphatic, or
(C6-C10)aryl-(C1-C12)-aliphatic,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, or SO$_2$ in a chemically stable arrangement;
Z is a carbon atom, —CHR—N—, —HN—CR— or —CHR—CHR—, —O—CHR—, —S—CHR—, —SO—CHR—, —SO$_2$—CHR—, or —N—;
wherein R is aliphatic, aryl, aralkyl or cycloalkyl;
$R_5$ is —(C1-C12) aliphatic, wherein any hydrogen is optionally substituted with halogen, and wherein any 10 hydrogen or halogen atom bound to any terminal carbon atom of $R_5$ is optionally substituted with sulfhydryl or hydroxy;
W is selected from: —C(O)OH;

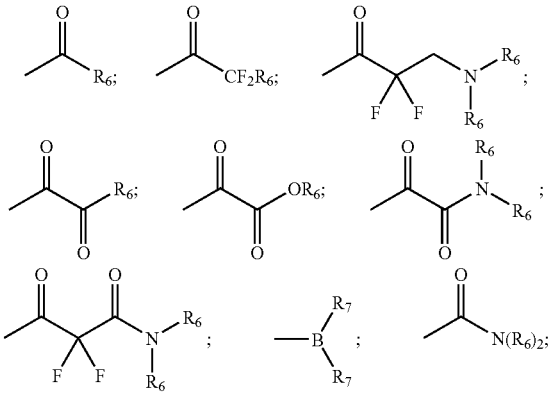

wherein each $R_6$ is independently:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic, or
two $R_6$groups, which are bound to the same nitrogen atom, form together with that nitrogen atom, a (C3-C10)-heterocyclic ring;
wherein $R_6$ is optionally substituted with up to 3 J substituents;
each $R_7$ is hydroxy, alkoxy, or aryloxy; or
each $R_7$ is an oxygen atom linked to an aliphatic group and, together with the boron to which they are each bound, the two $R_7$ groups form a 3-6 membered ring;
V is a bond, —CH(R$_8$)—, —N(R$_8$)—, —O—, —O—CH(R$_8$)—, —CH(R$_8$)—O—, —S—, —S—CH(R$_8$)—, —CH(R$_8$)—S—, —C(O)—, —C(O)—O—, —O—C(O)—, —C(O)—S—, —S—C(O)—, —C(O)—CHR$_8$—, —CHR₈—C(O)—, —N(R₈)C(O)—, —C(O)N(R₈)—, —S(O)—, —S(O)—CH(R₈), —CH(R₈)—S(O)—, —S(O)N(R₈)—, —N(R₈)S(O)—, —S(O)—N(R₈)—, —CH(R₈)—N(R)₈—S(O)—, —N(R₈)—S(O)—CH(R₈)—, —CH(R₈)—S(O)—N(R₈)—, —CH(R₈)—S(O)₂—, —S(O)₂—CH(R₈)—, —S(O)₂N(R₈)—, —N(R₈)—S(O)₂—, —S(O)₂—N(R₈)—CHR₈—, —CHR₈—N(R₈)—S(O)₂—, —N(R₈)—S(O)₂—CHR₈or —CH(R₈)—S(O)₂—N(R₈)—;

wherein R₈ is hydrogen or (C1-C12)-aliphatic;
T is selected from:
(C6-C10)-aryl,
(C6-C10)-aryl-(C1-C12)aliphatic,
(C3-C10)-cycloalkyl or -cycloalkenyl,
(C1-C12)-aliphatic-[(C3-C10)-cycloalkyl or -cycloalkenyl],
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic; or
T is selected from:

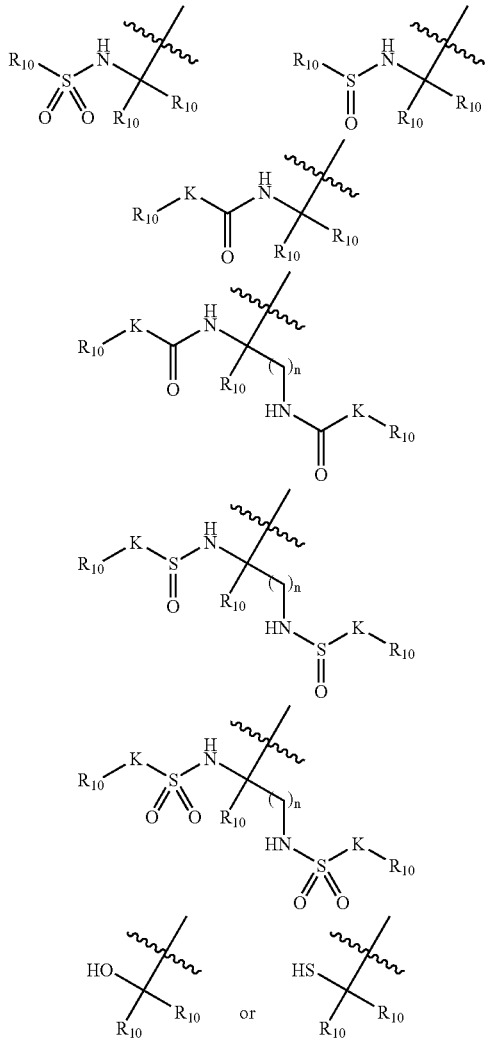

wherein:
R₁₀ is:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic,
wherein each T is optionally substituted with up to 3 J substituents;
K is a bond, (C1-C12)-aliphatic, —O—, —S—, —NR₉—, —C(O)—, or —C(O)—NR₉—, wherein R₉ is hydrogen or (C1-C12)-aliphatic; and
n is 1-3.

The present invention also provides a compound of formula (II):

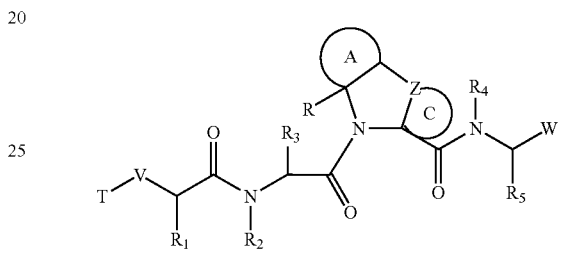

wherein:
T, V, R, R₁, R₂, R₃, R₄, R₅, Z and W are as defined above for compounds of formula (I);
ring A is a carbocyclic, heteroaryl or heterocyclic ring, wherein ring A is optionally fused to an carbocyclic, heterocyclic or heteroaryl ring;
wherein ring A has up to 4 substituents selected independently from J;
ring C is a cycloalkyl or heterocyclic ring; and
wherein ring C has up to 3 substituents selected independently from J; wherein J is as defined above for compounds of formula (I).

The present invention also provides a compound of formula (III):

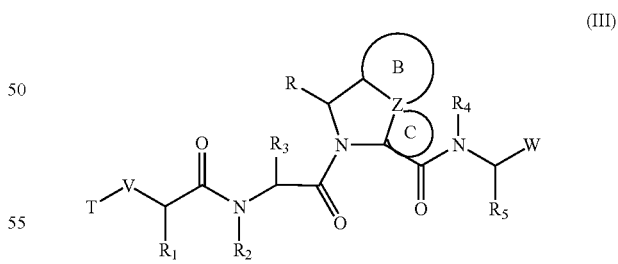

wherein:
T, V, R, R₁, R₂, R₃, R₄, R₅, Z and W are as defined above for compounds of formula (I);
ring B is a carbocyclic or heterocyclic ring, wherein ring B is optionally fused to a carbocyclic, heterocyclic or heteroaryl ring;
wherein ring B has up to 3 substituents selected independently from J;
ring C is a cycloalkyl or heterocyclic ring; and wherein ring C has up to 3 substituents selected independently from J; wherein J is as defined above for compounds of formula (I).

The present invention also provides a compound of formula (IV):

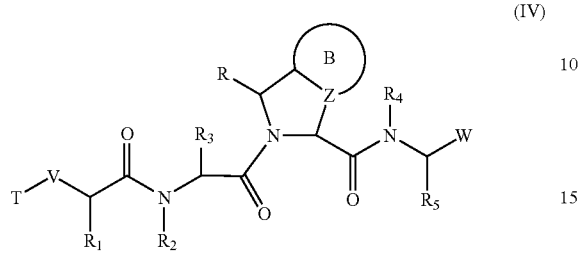

wherein:
T, V, R, $R_1$, $R_2$, $R_3$, $R_4$, $R_5$, Z and W are as defined above for compounds of formula (I);
ring B is a bridged bicyclic ring system containing 6-12 carbon atoms, wherein ring B is saturated or partially unsaturated; or
the ring system comprising ring B, together with the ring containing Z and the nitrogen atom, contains more than ten ring atoms; and
wherein ring B has up to 3 substituents selected independently from J; wherein J is as defined above for compounds of formula (I).

The invention also relates to compositions that comprise the above compounds and the use thereof. Such compositions may be useful to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

DETAILED DESCRIPTION OF THE INVENTION

In the description, the following abbreviations are used:

| Designation | Reagent or Fragment |
|---|---|
| Abu | aminobutyric acid |
| Ac | acetyl |
| AcOH | acetic acid |
| Bn | benzyl |
| Boc | tert-butyloxycarbonyl |
| Bz | benzoyl |
| Cbz | carbobenzyloxy |
| CDI | carbonyldiimidazole |
| DCE | 1,2-dichloroethane |
| DCM | dichloromethane |
| DIEA | diisopropylethylamine |
| DMA | dimethylacetamide |
| DMAP | dimethylaminopyridine |
| DMF | dimethylformamide |
| DPPA | diphenylphosphorylazide |
| DMSO | dimethylsulfoxide |
| Et | ethyl |
| EtOAc | ethyl acetate |
| FMOC | 9-fluorenylmethoxycarbonyl |
| HbtU | O-benzotriazolyl-N,N,N',N'-tetramethyluronium hexafluorophosphate |
| HOBt | N-hydroxybenzotriazole |

-continued

| Designation | Reagent or Fragment |
|---|---|
| HPLC | high performance liquid chromatography |
| Me | methyl |
| MS | mass spectrometry |
| NMP | N-methyl pyrrolidinone |
| ND | not determined |
| Pip | piperidine |
| Prz | piperazine |
| PyBrop | bromo-tris-pyrrolidinophosphonium hexafluorophosphate |
| Pyr | pyridine |
| THF | tetrahydrofuran |
| TFA | trifluoroacetic acid |
| TFE | trifluoroethanol |
| Tol | toluene |

The present invention provides a compound of formula (I):

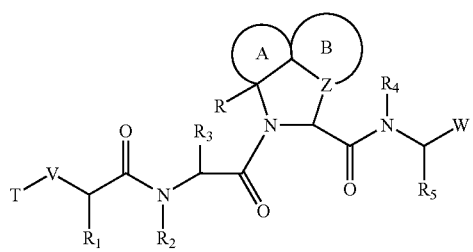

wherein:
ring A is a carbocyclic or heterocyclic ring, wherein ring A is optionally fused to a carbocyclic, heterocyclic or heteroaryl ring;
wherein ring A has up to 3 substituents selected independently from J;
ring B is a carbocyclic or heterocyclic ring, wherein ring B is optionally fused to a carbocyclic, heterocyclic or heteroaryl ring;
wherein ring B has up to 3 substituents selected independently from J;
J is halogen, —OR', —$NO_2$, —$CF_3$, —$OCF_3$, —R', oxo, —OR', —O-benzyl, —O-phenyl, 1,2-methylenedioxy, 1,2-ethylenedioxy, —N(R')$_2$, —SR', —SOR', —$SO_2$R', —C(O)R', —COOR' or —CON(R')$_2$, wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
$R_1$ and $R_3$ are independently:
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic, (C5-C10)-heteroaryl, or
(C5-C10)-heteroaryl-(C1-C12)-aliphatic,
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, or $SO_2$ in a chemically stable arrangement;
$R_2$ and $R_4$ are independently
hydrogen,
(C1-C12)-aliphatic,
(C3-C10)-cycloalkyl-(C1-C12)-aliphatic, or
(C6-C10)aryl-(C1-C12)-aliphatic,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, or $SO_2$ in a chemically stable arrangement;
Z is a carbon atom, —CHR—N—, —HN—CR— or —CHR—CHR—, —O—CHR, —S—CHR, —SO—CHR, —$SO_2$—CHR, or —N—;
wherein R is aliphatic, aryl, aralkyl or cycloalkyl;
$R_5$ is —(C1-C12) aliphatic, wherein any hydrogen is optionally substituted with halogen, and wherein any hydrogen or halogen atom bound to any terminal carbon atom of $R_5$ is optionally substituted with sulfhydryl or hydroxy;
W is selected from: —C(O)OH;

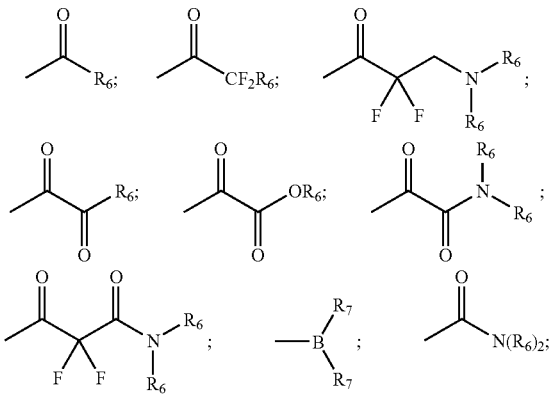

wherein each $R_6$ is independently:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic, or
two $R_6$ groups, which are bound to the same nitrogen atom, form together with that nitrogen atom, a (C3-C10)-heterocyclic ring;
wherein $R_6$ is optionally substituted with up to 3 J substituents;
each $R_7$ is hydroxy, alkoxy, or aryloxy; or
each $R_7$ is an oxygen atom linked to an aliphatic group and, together with the boron to which they are each bound, the two $R_7$ groups form a 3-6 membered ring;

V is a bond, —CH($R_8$)—, —N($R_8$)—, —O—, —O—CH($R_8$), —CH($R_8$)—O—, —S—, —S—CH($R_8$)—, —CH($R_8$)—S—, —C(O)—, —C(O)—O—, —O—C(O)—, —C(O)—S—, —C(O)—CH$R_8$—, —CH$R_8$—C(O)—, —N($R_8$)C(O)—, —C(O)N($R_8$)—, —S(O)—, —S(O)—CH($R_8$), —CH($R_8$)—S(O)—, —S(O)N($R_8$)—, —N($R_8$)S(O)—, —S(O)—N($R_8$)—CH$R_8$, —N($R_8$)—S(O)—CH$R_8$—, —CH$R_8$—S(O)$_2$, —S(O)$_2$—CH($R_8$)—, —CH($R_8$)—S(O)$_2$—, —S(O)$_2$N($R_8$)—, —N($R_8$)—S(O)$_2$—, —S(O)$_2$—N($R_8$)—CH$R_8$ or —N($R_8$)—S(O)$_2$—CH$R_8$;
wherein $R_8$ is hydrogen or (C1-C12)-aliphatic;
T is selected from:
(C6-C10)-aryl,
(C6-C10)-aryl-(C1-C12)aliphatic,
(C3-C10)-cycloalkyl or -cycloalkenyl,
(C1-C12)-aliphatic-[(C3-C10)-cycloalkyl or -cycloalkenyl],
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic; or
T is selected from:

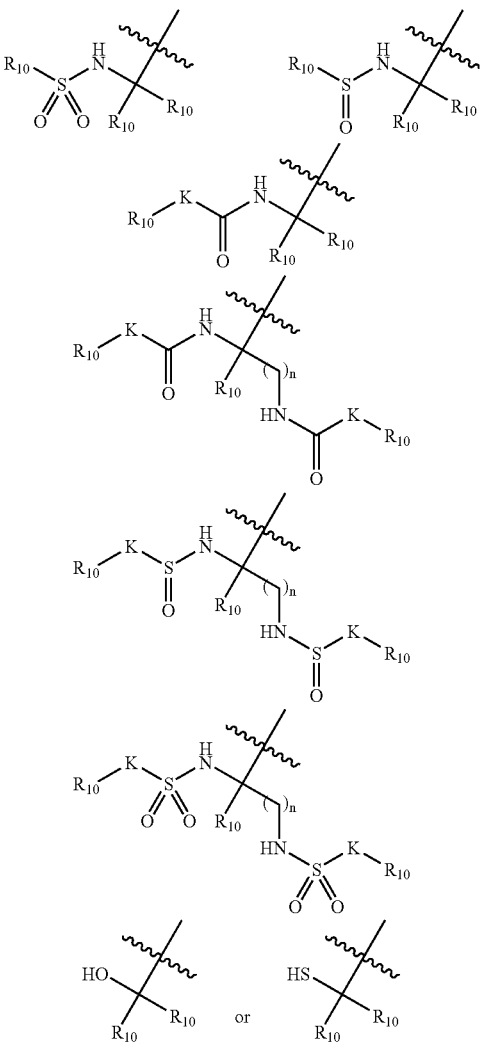

wherein:
$R_{10}$ is:
hydrogen,
(C1-C12)-aliphatic, (C1-C12)-aliphatic-[(C3-C10)-cycloalkyl or -cycloalkenyl], (C6-C10)-aryl, (C6-C10)-aryl-(C1-C12)aliphatic, (C3-C10)-cycloalkyl or -cycloalkenyl, (C3-C10)-heterocyclyl, (C3-C10)-heterocyclyl-(C1-C12)-aliphatic, (C5-C10)-heteroaryl, or (C5-C10)-heteroaryl-(C1-C12)-aliphatic, wherein each T is optionally substituted with up to 3 J substituents;

K is a bond, (C1-C12)-aliphatic, —O—, —S—, —NR$_9$—, —CC(O)—, or —C(O)—NR$_9$—, wherein R$_9$ is hydrogen or (C1-C12)-aliphatic; and n is 1-3.

Definitions

The term "aryl" as used herein means a monocyclic or bicyclic carbocyclic aromatic ring system comprising 6 to 10 atoms. Phenyl is an example of a monocyclic aromatic ring system. Bicyclic carbocyclic aromatic ring systems include systems wherein both rings are aromatic, e.g., naphthyl, and systems wherein only one of the two rings is aromatic, e.g., tetralin.

The bond "———" refers to an optionally present bond.

The term "heterocyclyl" or "heterocyclic" as used herein means a 3-10 membered monocyclic or bicyclic non-aromatic ring system having up to 4 heteroatom or heteroatom groups in each ring selected from O, N, NH, S, SO or SO$_2$ in a chemically stable arrangement. In such a bicyclic non-aromatic ring system embodiment of "heterocyclyl":

both rings may contain said heteroatom or heteroatom groups; or one ring may contain said heteroatom or heteroatom groups and the other ring may be a C3-C6 cycloalkyl or phenyl.

Heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroaryll" as used herein means a 5-membered monocyclic or bicyclic aromatic ring system having up to 4 heteroatom or heteroatom groups in each ring selected from O, N, NH or S in a chemically stable arrangement. In such a bicyclic aromatic ring system embodiment of "heteroaryl":

one or both rings may be aromatic;

both rings may contain said heteroatom or heteroatom groups; or one ring may contain said heteroatom or heteroatom groups and the other ring may be a C3-C6 cycloalkyl or phenyl.

Heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl). Each of the above aryl, heterocyclyl or heteroaryl above may contain up to 3 substituents independently selected from halogen, —OR', —NO$_2$, —CF$_3$, —OCF$_3$, —R', oxo, —OR', —O-benzyl, —O-phenyl, 1,2-methylenedioxy, 1,2-ethylenedioxy, —N(R')$_2$, —C(O)R', —COOR' or —CON(R')$_2$, wherein R' is independently selected from H, (C1-C6)-alkyl, (C2-C6)-alkenyl or alkynyl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

In an alternate embodiment of formulae (I)-(IV), R' is —CH$_2$—CH(CH$_3$)—CH$_3$, —C(CH$_3$)$_3$, —CH(CH$_3$)$_2$, —CH(CH$_3$)—CH$_2$—CH$_3$ or cyclohexyl; V is —C(O)N(R$_8$)—, —S(O)N(R$_8$)—, —S(O)$_2$N(R$_8$)—, a bond, —CH(R$_8$)—, —N(R$_8$)—, —O—, —O—CH(R$_8$)—, —S—, —S—CH(R$_8$), —C(O)—, —C(O)—O—, —C(O)—S—, —C(O)—CHR$_8$—, —S(O)—, —S(O)—CH(R$_8$), —S(O)—N(R$_8$)—CHR$_8$, —S(O)$_2$—, —S—(O)$_2$—CH(R$_8$)—, or —S(O)$_2$—N(R$_8$)—CHR$_8$; or J is halogen, —OR', —NO$_2$, —CF$_3$, —OCF$_3$, —R', oxo, —OR', —O-benzyl, —O-phenyl, 1,2-methylenedioxy, 1,2-ethylenedioxy, —N(R')$_2$, —SR', —SOR', —SO$_2$R', —C(O)R', —COOR' or —CON(R')$_2$, wherein R' is independently selected from:

hydrogen, (C1-C12)-aliphatic, (C3-C10)-cycloalkyl or -cycloalkenyl, (C1-C12)-aliphatic-[(C3-C10)-cycloalkyl or -cycloalkenyl], (C6-C10)-aryl, (C6-C10)-aryl-(C1-C12)aliphatic, (C3-C10)-heterocyclyl, (C6-C10)-heterocyclyl-(C1-C12)aliphatic, (C5-C10)-heteroaryl, or (C5-C10)-heteroaryl-(C1-C12)-aliphatic;

and the other variables are as defined herein.

In compounds of formula (I), ring A is preferably selected from:

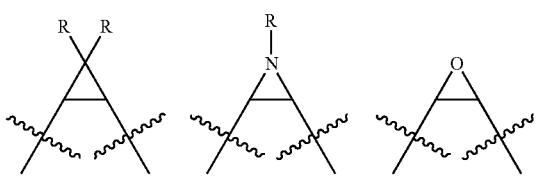

-continued
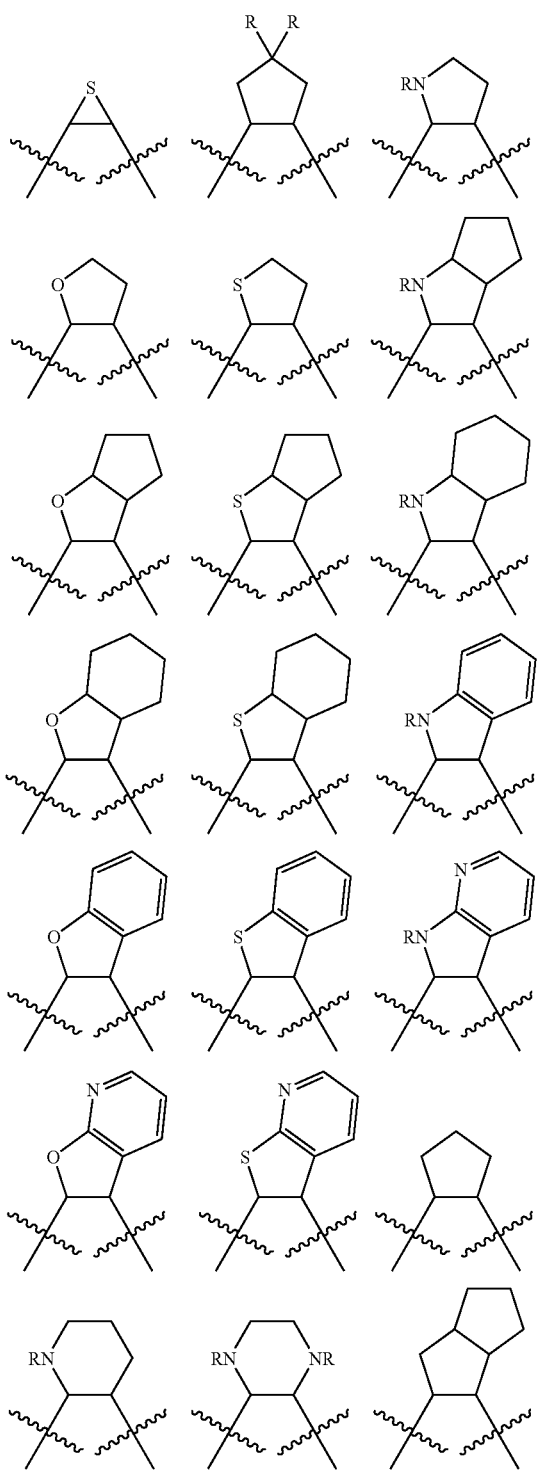
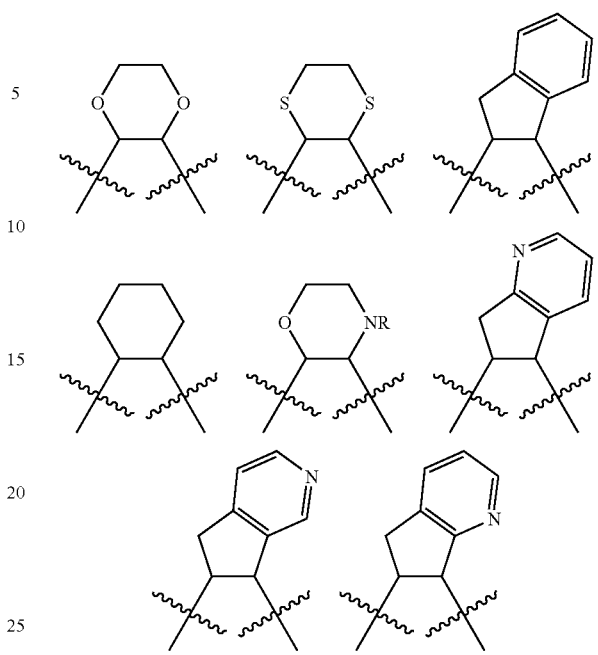
wherein R is aliphatic, aryl, aralkyl or cycloalkyl.
More preferably, ring A is selected from:
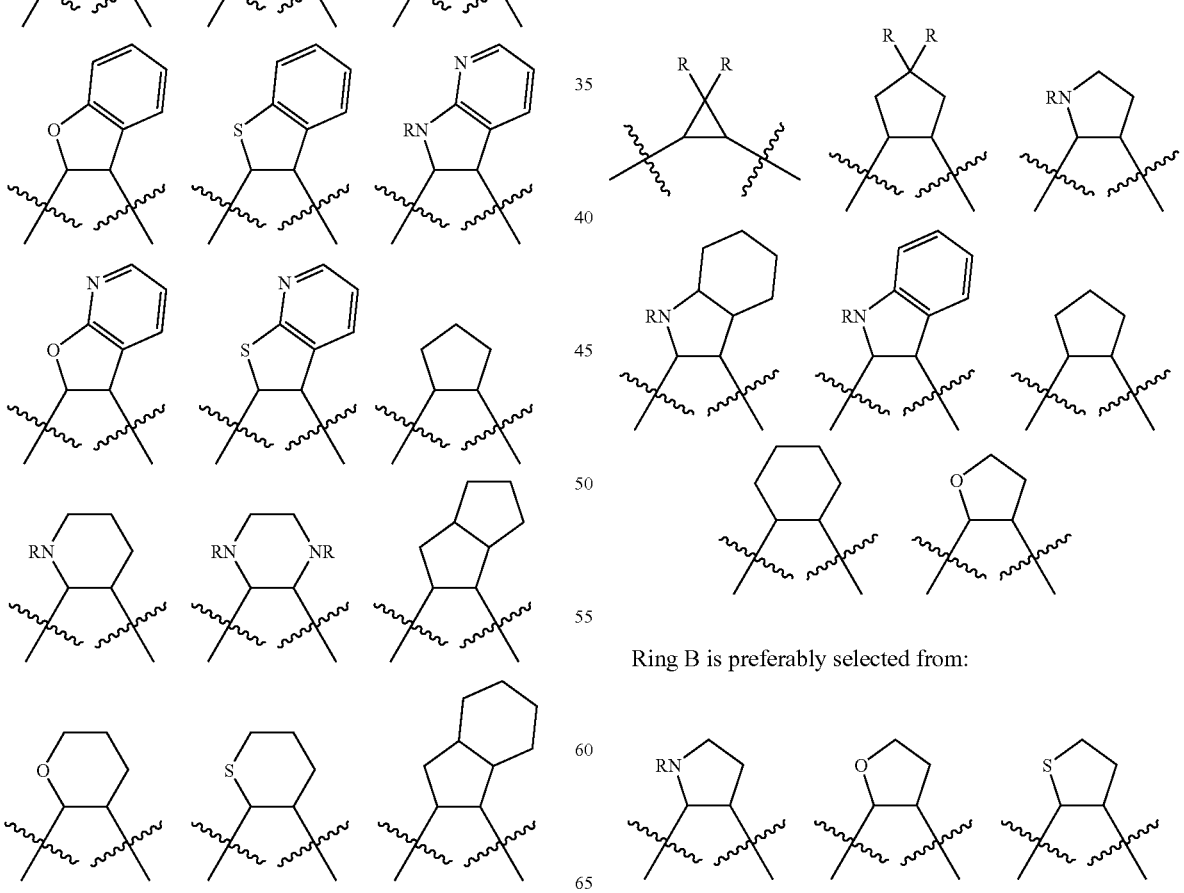
Ring B is preferably selected from:

-continued

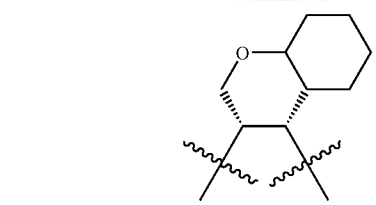

wherein R is aliphatic, aryl, aralkyl or cycloalkyl.

More preferably, ring B is selected from:

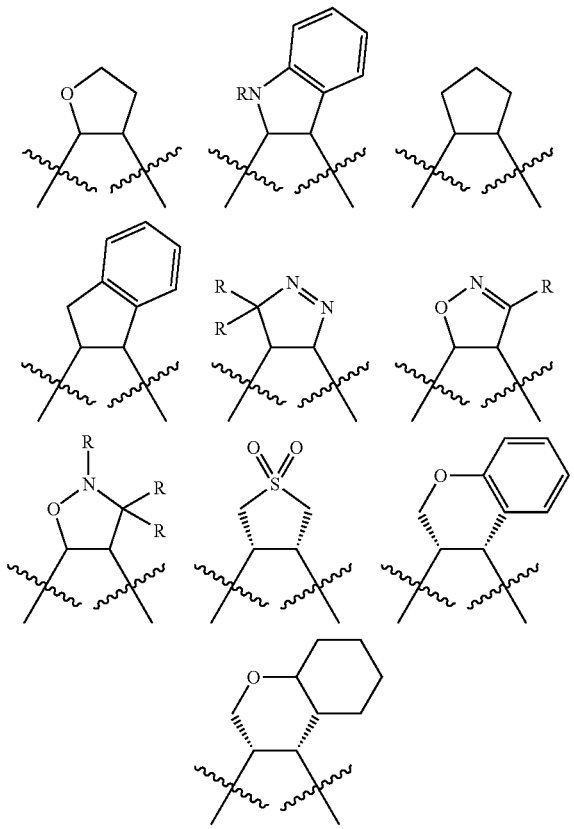

According to another preferred embodiment of compounds of formula (I), rings A, B, together with the ring connected thereto include:

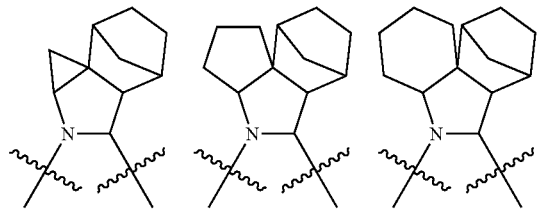

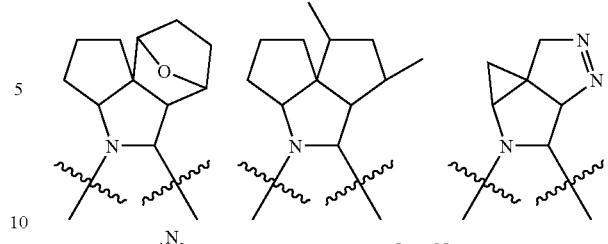

According to another preferred embodiment, $R_1$ is selected from —(C1-C10)alkyl, —(C3-C7)cycloalkyl, or —((C1-C6)alkyl)-((C3-C7)cycloalkyl). More preferably, $R_1$ is selected from:

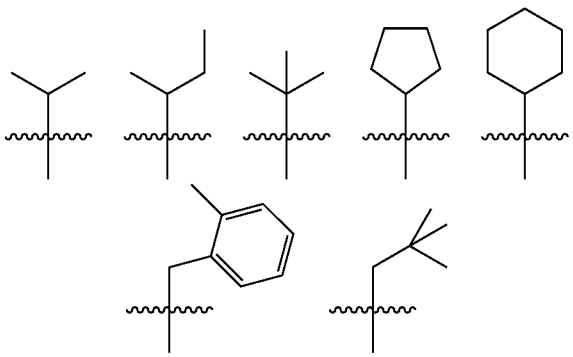

Even more preferably, $R_1$ is selected from —$CH_2$—C($CH_3)_3$, —C($CH_3)_3$, —CH($CH_3)_2$, —CH($CH_3$)—$CH_2$—$CH_3$, or cyclohexyl. Most preferably $R_1$ is cyclohexyl.

According to another preferred embodiment, $R_2$ is (C1-C12)-aliphatic. More preferably, $R_2$ is selected from hydrogen, methyl, ethyl or propyl. Even more preferably, $R_2$ is hydrogen or methyl. Most preferably, $R_2$ is hydrogen.

According to another preferred embodiment, $R_3$ is selected from —(C1-C10)alkyl, —(C3-C7)cycloalkyl, or —((C1-C6)alkyl)-((C3-C7)cycloalkyl).

More preferably, $R_3$ is selected from:

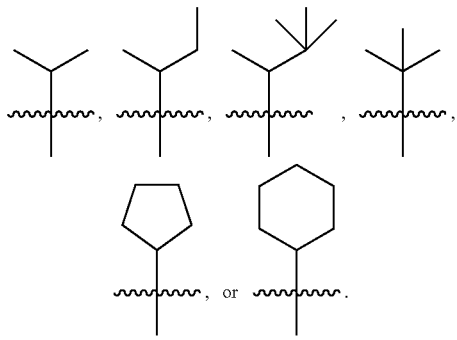

Even more preferably, $R_3$ is selected from —C($CH_3)_2$, —CH($CH_3)_2$, —CH($CH_3$)—$CH_2$—$CH_3$, or cyclohexyl. Most preferably, $R_3$ is selected from —C($CH_3)_3$ or —CH($CH_3)_2$.

According to another preferred embodiment, $R_4$ is (C1-C12)-aliphatic. More preferably, $R_4$ is selected from hydrogen, methyl, ethyl or propyl. Even more preferably, $R_4$ is selected from hydrogen.

According to another preferred embodiment, $R_5$ is —(C2-C7)alkyl optionally substituted with halogen.

Preferably, $R_5$ is selected from:

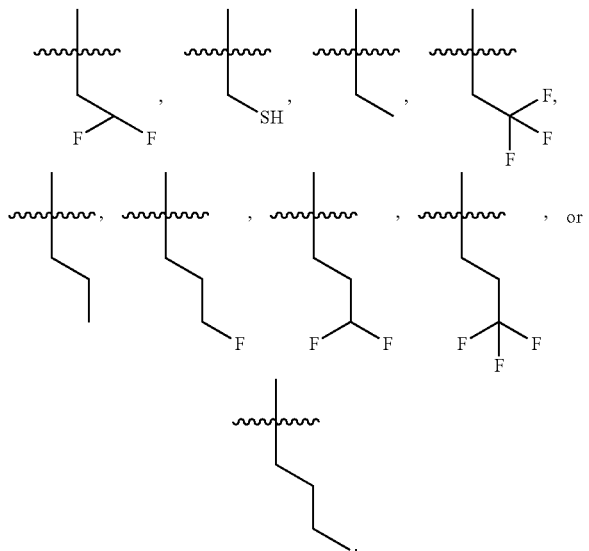

More preferably, $R_5$ is selected from —$CH_2CH_2CH_3$, —$CH_2CH_2CH_2CH_3$, —$CH_2CH_2CH_2F$, —$CH_2CH_2CHF_2$, or —$CH_2CH_2CF_3$. Even more preferably, $R_5$ is selected from —$CH_2CH_2CH_3$, —$CH_2CH_2CH_2CH_3$ or —$CH_2CH_2CHF_2$. Most preferably, $R_5$ is —$CH_2CH_2CH_3$ or —$CH_2CH_2CH_2CH_3$.

According to another preferred embodiment W is selected from: CHO, —C(O)—$R_6$, —$CO_2H$, —C(O)—C(O)—$R_6$, or —C(O)—C(O)—NH($R_6$), wherein $R_6$ is selected from hydrogen, aryl, heteroaryl, heterocyclyl, C3-C6 alkyl, C3-C6 cycloalkyl, hydroxy, —O—C1-C6 alkyl, wherein —NH($R_6$) is selected from —NH—(C3-C6 cycloalkyl), NH-aralkyl, —NH-alkylheteroaryl, —NH-alkylheterocyclyl, and wherein said aryl, heterocyclyl or heteroaryl is optionally substituted with up to 3 halogen atoms.

More preferably, $R_6$ or —NH($R_6$) is selected from:

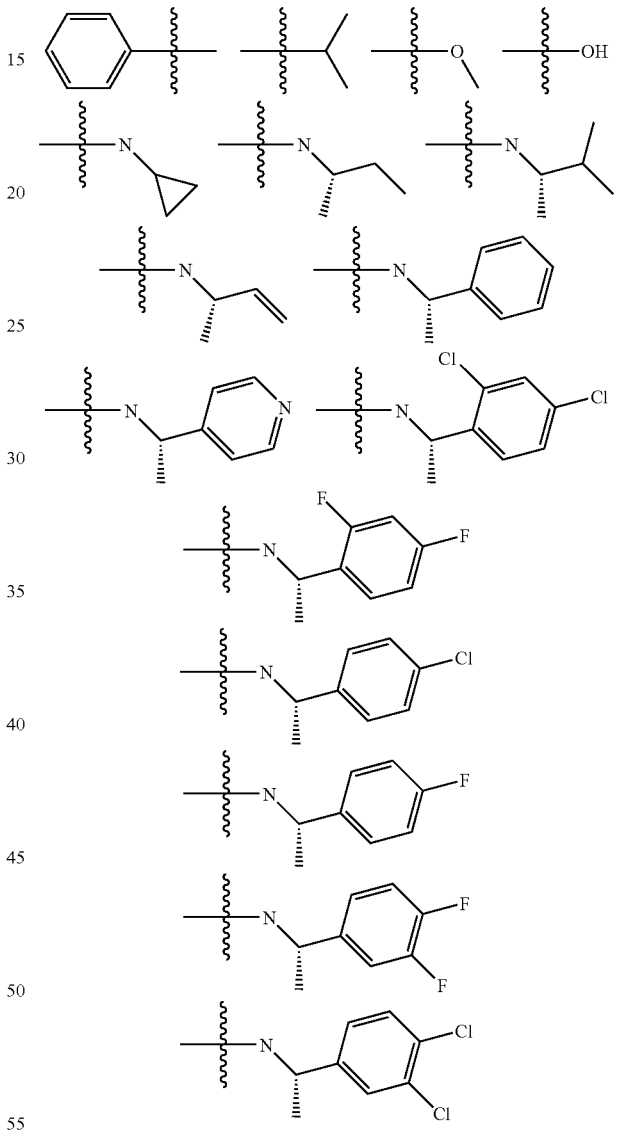

According to another preferred embodiment W is selected from —C(O)OH or —C(O)—C(O)—$R_6$. More preferably, W is —C(O)—C(O)—$R_6$. Preferably, $R_6$ is isopropyl.

According to a preferred embodiment, W is —C(O)—C(O)—$R_6$. Preferably, $R_6$ is isopropyl.

According to another preferred embodiment, W is —C(O)—C(O)—$OR_6$. Preferably, $R_6$ is hydrogen, (C1-C12)-aliphatic, (C6-C10)-aryl, (C3-C10)-cycloalkyl or -cycloalkenyl, (C3-C10)-heterocyclyl or (C5-C10)heteroaryl. More preferably, $R_6$ is H or methyl.

According to yet another preferred embodiment, W is —C(O)—C(O)—N(R₆)₂. Preferably, R₆ is hydrogen, (C3-C10)-cycloalkyl or -cycloalkenyl, or (C3-C10)-heterocyclyl.

In another preferred embodiment of compounds of formula (I) is where W is C(O)—C(O)—N(R₆)₂, the NR₆R₆ portion of the W moiety is —NH—(C3-C6)cycloalkyl, —NH—CH(CH₃)—(C6-C10)aryl or —NH—CH(CH₃)—(C3-C10)heterocyclyl, or —NH—CH(CH₃)—(C5-C10)heteroaryl, wherein said aryl, heterocyclyl, or heteroaryl is optionally substituted with halogen.

Alternatively, the NR₆R₆ portion is —NH—(C3-C6)cycloalkyl, —NH—CH(CH₃)—(C6-C10)aryl, or —NH—CH(CH₃)—(C5-C10)heteroaryl, wherein said aryl or said heterocyclyl is optionally substituted with halogen; or NR₆R₆ is —NH—(C3-C6) cycloalkyl, —NH—CH(CH₃)—(C6-C10)aryl, or —NH—CH(CH₃)—(C3-C10)heterocyclyl, wherein said aryl or said heterocyclyl is optionally substituted with halogen.

In other preferred embodiment of formula I, NR₆R₆ in W is:

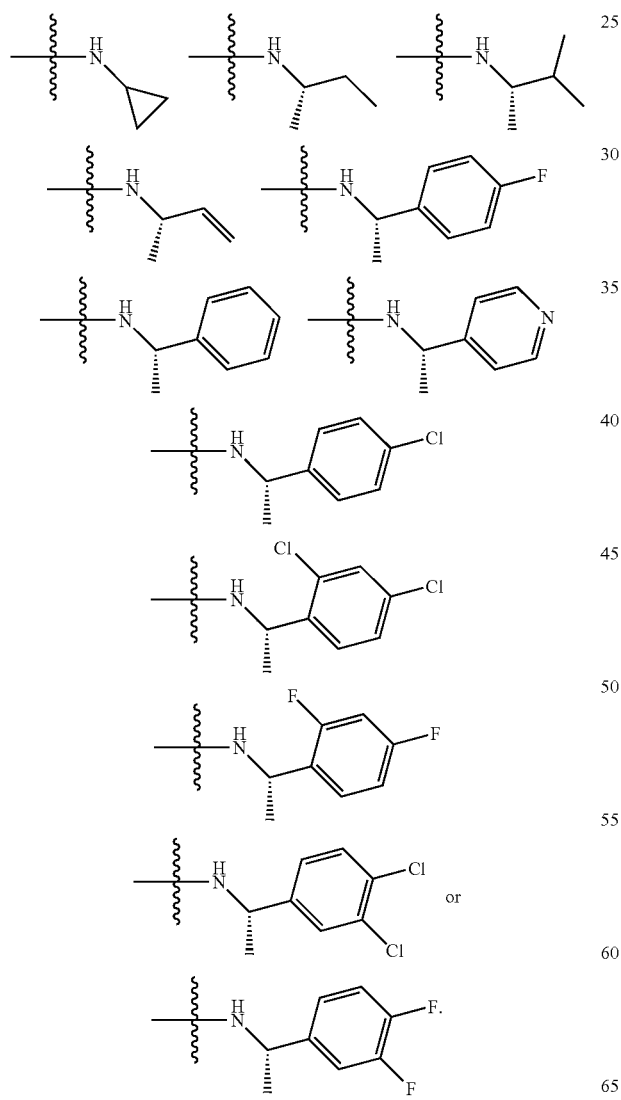

More preferably, NR₆R₆ is:

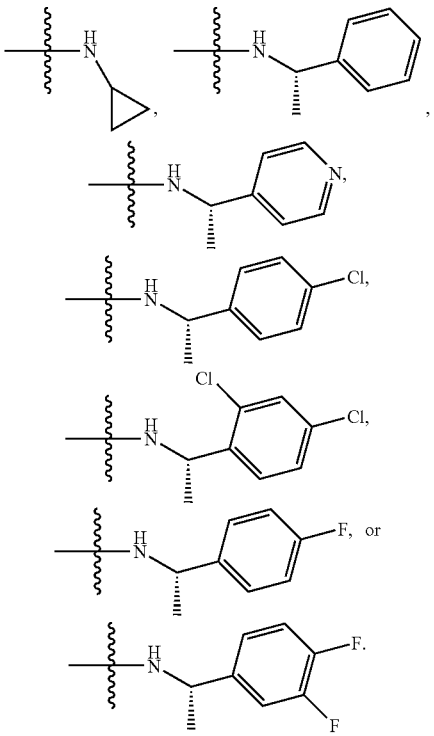

Even more preferably, NR₆R₆ is:

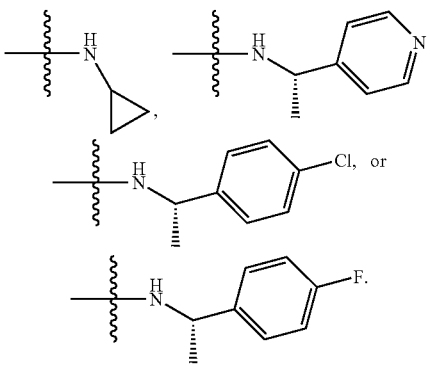

Most preferably, NR₆R₆ is:

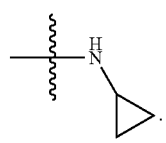 [SMILES: *NC1CC1]

According to another preferred embodiment, when W is —B(R₇)₂, each R₇ is selected from hydroxy, alkoxy, or aryloxy.

According to yet another preferred embodiment, when W is —B(R₇)₂, each R₇ is selected from an oxygen atom linked to an aliphatic group and, together with the boron to which they are each bound, the two R₇ groups form a 5-8 membered ring.

According to another preferred embodiment, V is a bond, —CH(R₈)—, —N(R₈)—, —O—, —O—CH(R₈), —S—, —S—CH(R₈), —C(O)—, —C(O)—O—, —C(O)—S—, —C(O)—CHR₈—, —C(O)N(R₈)—, —S(O)—, —S(O)—CH(R₈)—, —S(O)N(R₈)—, —S(O)—N(R₈)—CHR₈, —S(O)₂—, —S—(O)₂—CH(R₈)—, —S(O)₂N(R₈)—, or —S(O)₂—N(R₈)—CHR₈; wherein R₈ is hydrogen or —(C1-C3)alkyl;

According to another preferred embodiment, V is —NH—.

According to yet another preferred embodiment, V is —C(O)—.

According to yet another preferred embodiment, V is —C(O)—NR₈—. More preferably, V is —C(O)—NH—.

According to yet another preferred embodiment T is a heterocyclyl or heteroaryl, optionally having up to 3 substituents as defined above.

According to yet another preferred embodiment, T is a —(C5-C10)heteroaryl.

According to yet another preferred embodiment, T is selected from 3-1H-benzimidazol-2-one, 3-(1-alkyl)-benzimidazol-2-one, 2-tetrahydrofuranyl, 3-tetrahydrofuranyl, pyrazolinyl, 1,3-dihydro-imidazol-2-one, 2-imidazolyl, 4-imidazolyl, 5-imidazolyl, 2-oxazolyl, 4-oxazolyl, 5-oxazolyl, 2-pyrrolyl, 3-pyrrolyl, 2-pyrimidinyl, 4-pyrimidinyl, 5-pyrimidinyl, 5-tetrazolyl, pyrazolyl, pyrazinyl or 1,3,5-triazinyl.

Even more preferably, T is selected from 3-1H-benzimidazol-2-one, 3-(1-alkyl)-benzimidazol-2-one, pyrazolinyl, 1,3-dihydro-imidazol-2-one, 2-imidazolyl, 2-pyrrolyl, 2-pyrimidinyl, 5-pyrimidinyl, 5-tetrazolyl or pyrazinyl.

Most preferred is when T or R⁷ is selected from:

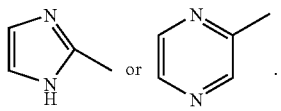

Preferred substituents on T in the above embodiments are halogen, —CF₃, —OCF₃, oxo, —COOR', or —CON(R')₂, wherein R' is as defined above.

According to another preferred embodiment of this invention, T contains at least one hydrogen bond donor moiety selected from —NH₂, —NH—, —OH, and —SH.

In a preferred embodiment, T is:

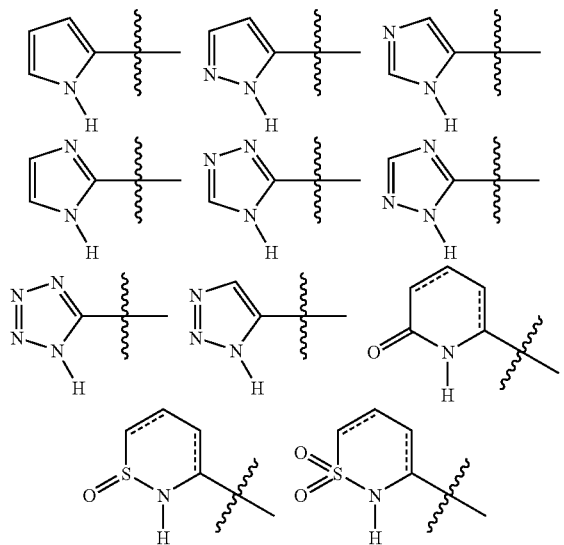

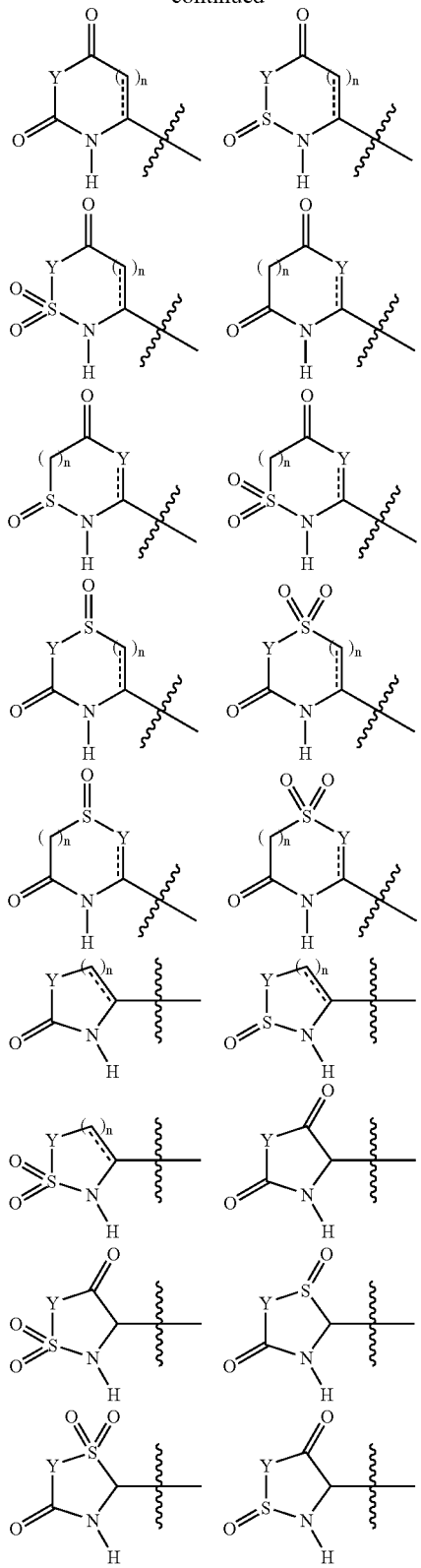

wherein:
T is optionally substituted with up to 3 J substituents, wherein J is as defined in claim 1;
Y is independently O, S, NR₁₀, or C(R₁₀)₂;
n is independently 1 or 2; and
===== is independently a single bond or a double bond.

In another preferred embodiment, T is:

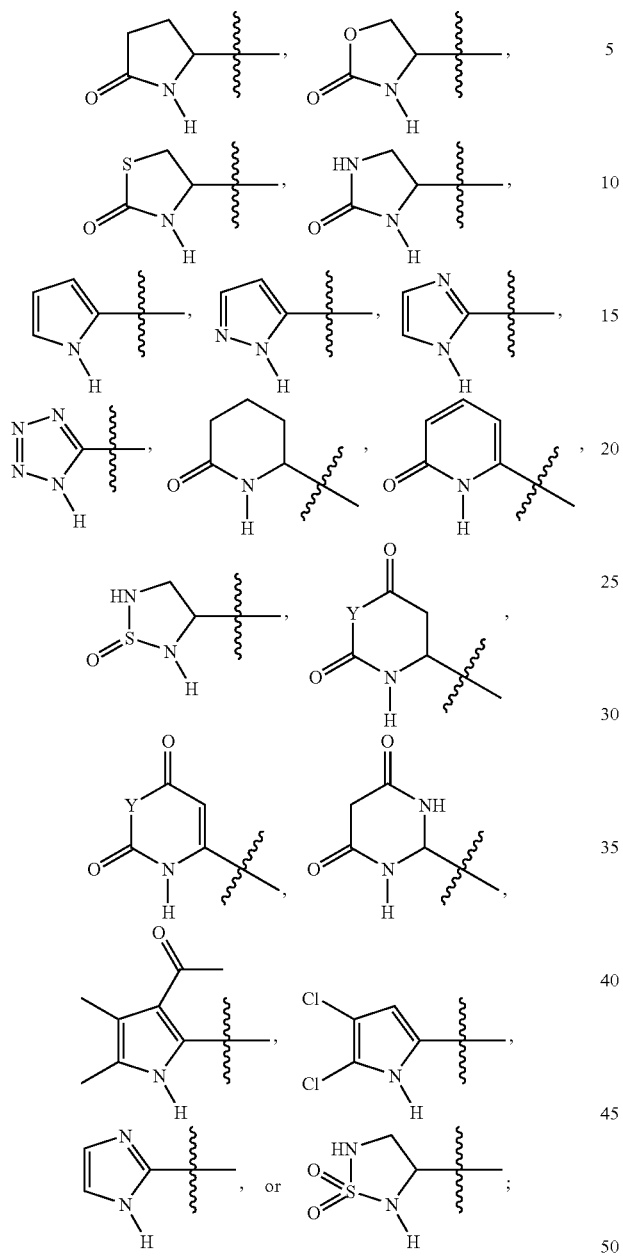

wherein Y is as defined above.
More preferably T is

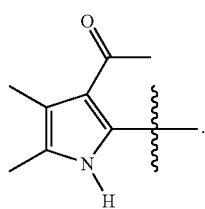 [SMILES: *c1[nH]c(C)c(C)c1C(C)=O]

According to yet another preferred embodiment, T is:
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic,
wherein each T is optionally substituted with up to 3 J substituents.

According to yet another preferred embodiment of this invention, T:

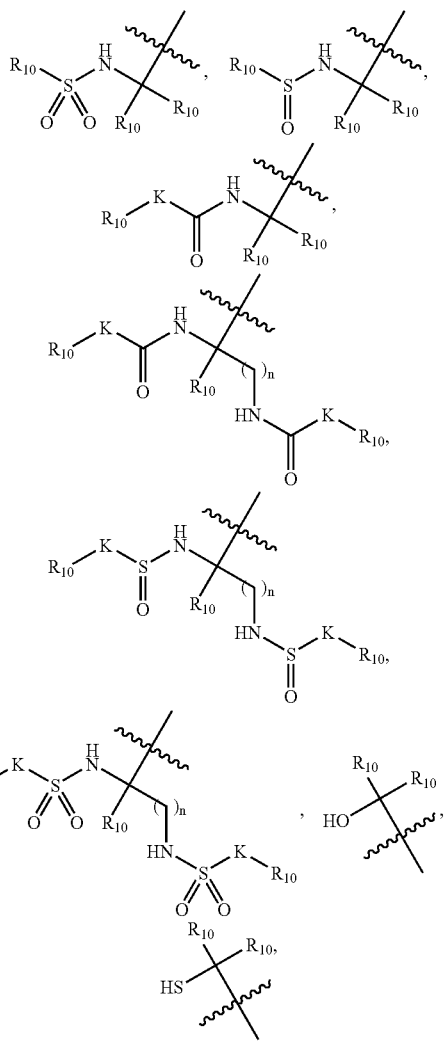

wherein:
$R_{10}$ is:
hydrogen,
(C1-C12)-aliphatic,
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic, (C5-C10)heteroaryl, or
(C5-C10)heteroaryl-(C1-C12)-aliphatic,
wherein each T is optionally substituted with up to 3 J substituents;

K is a bond, —O—, —S—, —NR$_9$—, —C(O)—, or —C(O)—NR$_9$—, wherein R$_9$ is hydrogen or C1-C12 aliphatic; and n is 1-3.

More preferably, T is:

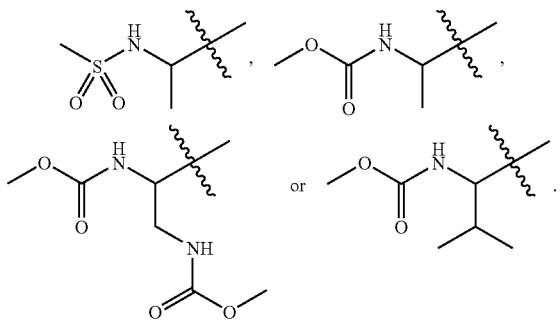

According to another embodiment, the present invention provides compounds of formula (II):

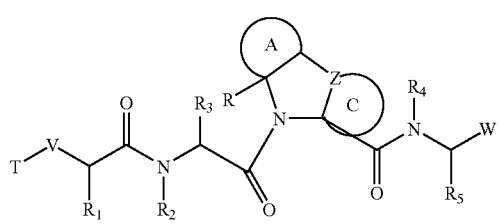

(II)

wherein:
ring A is a carbocyclic, heteroaryl or heterocyclic ring, wherein ring A is optionally fused to an carbocyclic, heterocyclic or heteroaryl ring;
wherein ring A has up to 4 substituents selected independently from J;
ring C is a cycloalkyl or heterocyclic ring;
wherein ring C has up to 3 substituents selected independently from J;
J is halogen, —OR', —NO$_2$, —CF$_3$, —OCF$_3$, —R', oxo, —O-benzyl, —O-phenyl, 1,2-methylenedioxy, 1,2-ethylenedioxy, —N(R')$_2$, —SR', —SOR', —SO$_2$R', —C(O)R', —OC(O)R', —COOR' or —CON(R')$_2$, wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
R$_1$ and R$_3$ are independently:
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic,
wherein each of R$_1$ and R$_3$ is independently and optionally substituted with up to 3 substituents independently selected from J;
wherein up to 3 aliphatic carbon atoms in R$_1$ and R$_3$ may be replaced by a heteroatom selected from O, NH, S, SO, or SO$_2$ in a chemically stable arrangement;
R$_2$ and R$_4$ are independently
hydrogen,
(C1-C12)-aliphatic,
(C3-C10)-cycloalkyl-(C1-C12)-aliphatic, or
(C6-C10)aryl-(C1-C12)-aliphatic,
wherein each of R$_2$ and R$_4$ is independently and optionally substituted with up to 3 substituents independently selected from J;
wherein up to two aliphatic carbon atoms in R$_2$ and R$_4$ may be replaced by a heteroatom selected from O, NH, S, SO, or SO$_2$ in a chemically stable arrangement;
Z is a carbon atom, —CHR—N—, —HN—CR— or —CHR—CHR—, —O—CHR—, —S—CHR—, —SO—CHR—, —SO$_2$—CHR—, or —N—;
wherein R is aliphatic, aryl, aralkyl or cycloalkyl;
R$_5$ is —(C1-C12) aliphatic, wherein any hydrogen is optionally substituted with halogen, and wherein any hydrogen or halogen atom bound to any terminal carbon atom of R$_5$ is optionally substituted with sulfhydryl or hydroxy;
W is selected from: —C(O)OH;

wherein each R$_6$ is independently:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)heteroaryl, or
(C5-C10)-heteroaryl-(C1-C12)-aliphatic, or
two R$_6$ groups, which are bound to the same nitrogen atom, form together with that nitrogen atom, a (C3-C10)-heterocyclic ring;

wherein $R_6$ is optionally substituted with up to 3 J substituents;

each $R_7$ is hydroxy, alkoxy, or aryloxy; or each $R_7$ is an oxygen atom linked to an aliphatic group and, together with the boron to which they are each bound, the two $R_7$ groups form a 3-6 membered ring;

V is a bond, —CH($R_8$)—, —N($R_8$)—, —O—, —O—CH($R_8$), —CH($R_8$)—O—, —S—, —S—CH($R_8$)—, —CH($R_8$)—S—, —C(O)—, —C(O)—O—, —O—C(O)—, —C(O)—S—, —C(O)—CHR$_8$—, —CHR$_8$—C(O)—, —N($R_8$)C(O)— —C(O)N($R_8$)—, —S(O)—, —S(O)—CH($R_8$), —CH($R_8$)—S(O)—, —S(O)N($R_8$)—, —N($R_8$)S(O)—, —S(O)—N($R_8$)—CHR$_8$, —N($R_8$)—S(O)—CHR$_8$—, —CHR$_8$—S(O)$_2$, —S(O)$_2$—CH($R_8$)—, —CH($R_8$)—S(O)$_2$—, —S(O)$_2$N($R_8$)—, —N($R_8$)—S(O)$_2$—, —S(O)$_2$—N($R_8$)—CHR$_8$ or —N($R_8$)—S(O)$_2$—CHR$_8$;

wherein $R_8$ is hydrogen or (C1-C12)-aliphatic;

T is selected from:
(C6-C10)-aryl,
(C6-C10)-aryl-(C1-C12)aliphatic,
(C3-C10)-cycloalkyl or -cycloalkenyl,
(C1-C12)-aliphatic-[(C3-C10)-cycloalkyl or -cycloalkenyl], (C3-C10)-heterocyclyl, (C3-C10)-heterocyclyl-(C1-C12)-aliphatic,
(C5-C10)heteroaryl, or
(C5-C10)heteroaryl-(C1-C12)-aliphatic; or T is selected from:

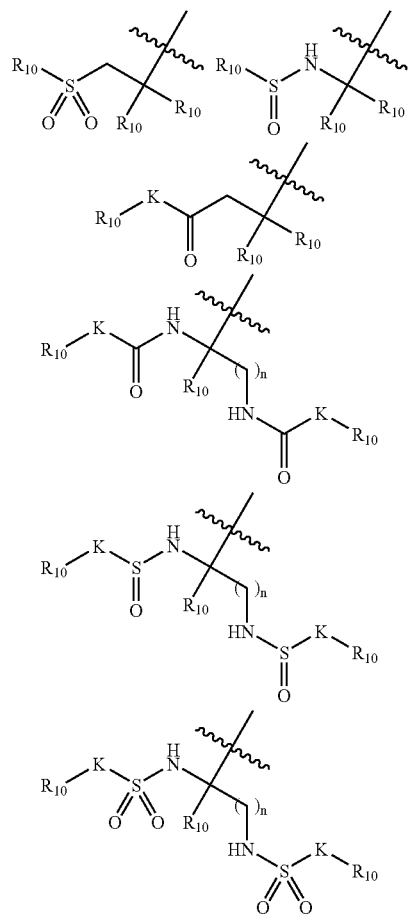

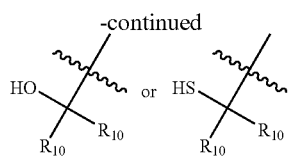

wherein:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic, wherein each T is optionally substituted with up to 3 J substituents;

K is a bond, (C1-C12)-aliphatic, —O—, —S—, —NR$_9$—, —C(O)—, or —C(O)—NR$_9$—, wherein $R_9$ is hydrogen or (C1-C12)-aliphatic; and n is 1-3.

In compounds of formula (II), ring C is preferably selected from:

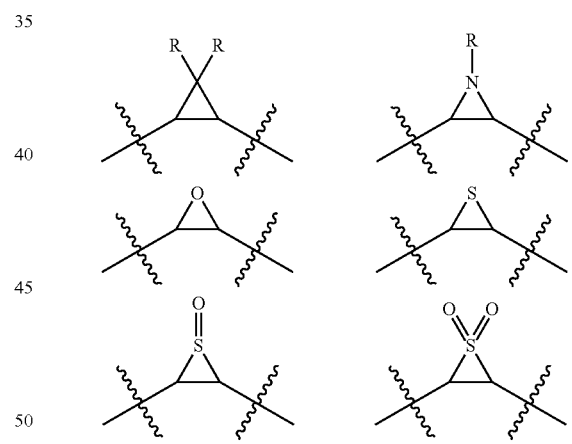

In compounds of formula (II), rings A and C, together with the ring that they are attached to, are preferably selected from:

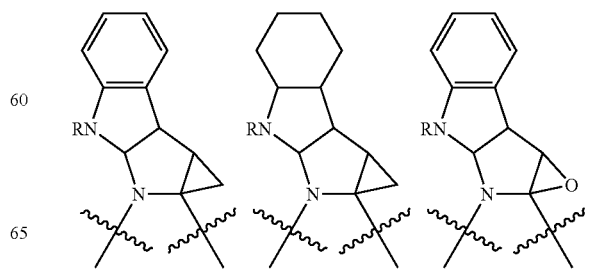

-continued

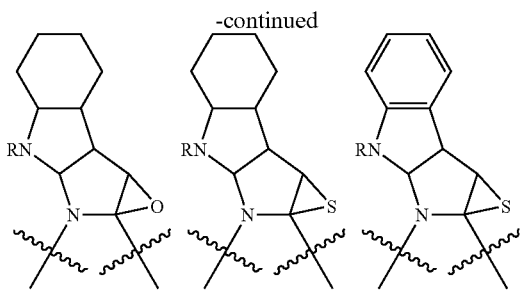

According to another preferred embodiment, $R_1$ is selected from —(C1-C10)alkyl, —(C3-C7)cycloalkyl, or —((C1-C6)alkyl)-((C3-C7)cycloalkyl). More preferably, $R_1$ is selected from:

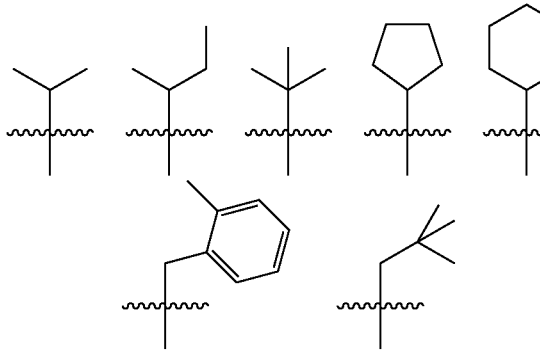

Even more preferably, $R_1$ is selected from —CH$_2$—C(CH$_3$)$_3$, —C(CH$_3$)$_3$, —CH(CH$_3$)$_2$, —CH(CH$_3$)—CH$_2$—CH$_3$, or cyclohexyl. Most preferably $R_1$ is cyclohexyl.

According to another preferred embodiment, $R_2$ is (C1-C12)-aliphatic. More preferably, $R_2$ is selected from hydrogen, methyl, ethyl or propyl. Even more preferably, $R_2$ is hydrogen or methyl. Most preferably, $R_2$ is hydrogen.

According to another preferred embodiment, $R_3$ is selected from —(C1-C10)alkyl, —(C3-C7)cycloalkyl, or —((C1-C6)alkyl)-((C3-C7)cycloalkyl).

More preferably, $R_3$ is selected from:

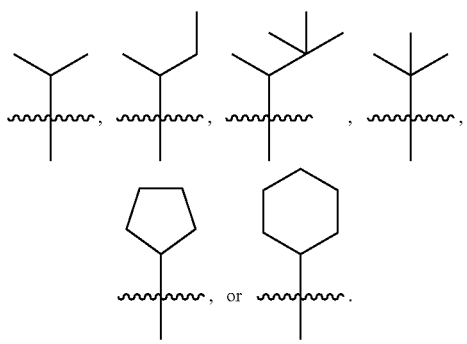

Even more preferably, $R_3$ is selected from —C(CH$_3$)$_2$, —CH(CH$_3$)$_2$, —CH(CH$_3$)—CH$_2$—CH$_3$, or cyclohexyl. Most preferably, $R_3$ is selected from —C(CH$_3$)$_3$ or —CH(CH$_3$)$_2$.

According to another preferred embodiment, $R_4$ is (C1-C12)-aliphatic. More preferably, $R_4$ is selected from hydrogen, methyl, ethyl or propyl. Even more preferably, $R_4$ is selected from hydrogen.

According to another preferred embodiment, $R_5$ is —(C2-C7)alkyl optionally substituted with halogen. Preferably, $R_5$ is selected from:

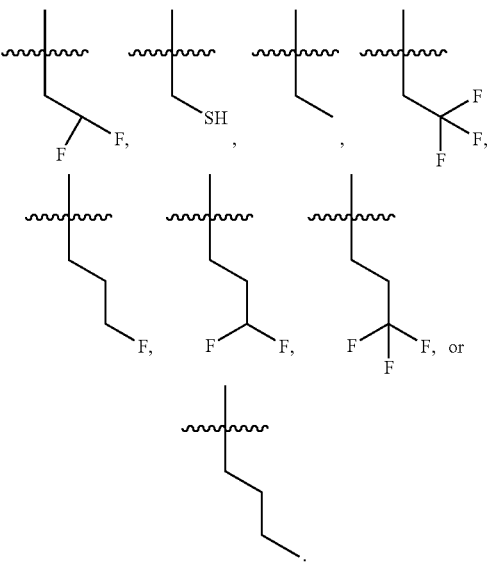

More preferably, $R_5$ is selected from —CH$_2$CH$_2$CH$_3$, —CH$_2$CH$_2$CH$_2$CH$_3$, —CH$_2$CH$_2$CH$_2$F, —CH$_2$CH$_2$CHF$_2$, or —CH$_2$CH$_2$CF$_3$. Even more preferably, $R_5$ is selected from —CH$_2$CH$_2$CH$_3$, —CH$_2$CH$_2$CH$_2$CH$_3$ or —CH$_2$CH$_2$CHF$_2$. Most preferably, $R_5$ is —CH$_2$CH$_2$CH$_3$ or —CH$_2$CH$_2$CH$_2$CH$_3$.

According to another preferred embodiment W is selected from: CHO, —C(O)—R$_6$, —CO$_2$H, —C(O)—C(O)—R$_6$, or —C(O)—C(O)—NH(R$_6$), wherein R$_6$ is selected from hydrogen, aryl, heteroaryl, heterocyclyl, C3-C6 alkyl, C3-C6 cycloalkyl, hydroxy, —O—C1-C6 alkyl, wherein —NH(R$_6$) is selected from —NH—(C3-C6 cycloalkyl), NH-aralkyl, —NH-alkylheteroaryl, —NH-alkylheterocyclyl, and wherein said aryl, heterocyclyl or heteroaryl is optionally substituted with up to 3 halogen atoms.

More preferably, $R_6$ or —NH(R$_6$) is selected from:

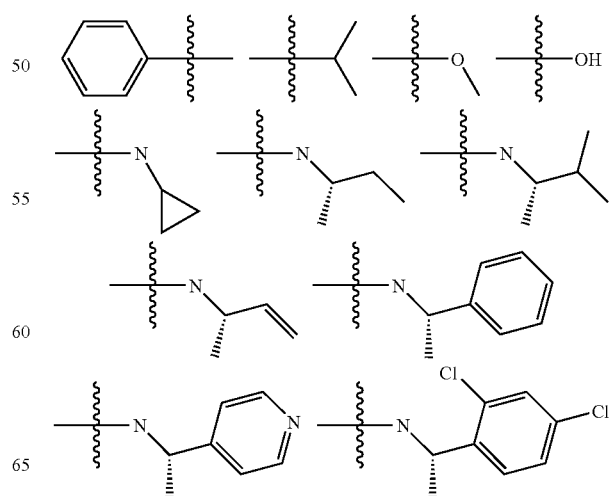

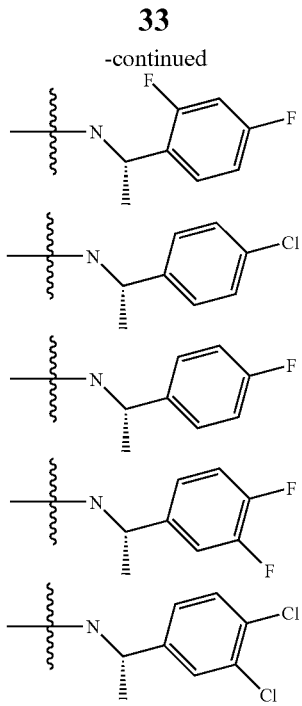

According to another preferred embodiment w is selected from —C(O)OH or —C(O)—C(O)—R$_6$. More preferably, W is —C(O)—C(O)—R$_6$. Preferably, R$_6$ is isopropyl.

According to a preferred embodiment, W is —C(O)—C(O)—R$_6$. Preferably, R$_6$ is isopropyl.

According to another preferred embodiment, W is —C(O)—C(O)—OR$_6$. Preferably, R$_6$ is hydrogen, (C1-C12)-aliphatic, (C6-C10)-aryl, (C3-C10)-cycloalkyl or -cycloalkenyl, (C3-C10)-heterocyclyl or (C5-C10)heteroaryl. More preferably, R$_6$ is H or methyl.

According to yet another preferred embodiment, W is —C(O)—C(O)—N(R$_6$)$_2$. Preferably, R$_6$ is hydrogen, (C3-C10)-cycloalkyl or -cycloalkenyl, or (C3-C10)-heterocyclyl.

In another preferred embodiment of compounds of formula (II) is where W is C(O)—C(O)—N(R$_6$)$_2$, the NR$_6$R$_6$ portion of the W moiety is —NH—(C3-C6)cycloalkyl, —NH—CH(CH$_3$)—(C6-C10)aryl or —NH—CH(CH$_3$)—(C3-C10)heterocyclyl, or —NH—CH(CH$_3$)—(C5-C10)heteroaryl, wherein said aryl, heterocyclyl, or heteroaryl is optionally substituted with halogen.

Alternatively, the NR$_6$R$_6$ portion is —NH—(C3-C6)cycloalkyl, —NH—CH(CH$_3$)—(C6-C10)aryl, or —NH—CH(CH$_3$)—(C5-C10)heteroaryl, wherein said aryl or said heterocyclyl is optionally substituted with halogen; or NR$_6$R$_6$ is —NH—(C3-C6) cycloalkyl, —NH—CH(CH$_3$)—(C6-C10)aryl, or —NH—CH(CH$_3$)—(C3-C10)heterocyclyl, wherein said aryl or said heterocyclyl is optionally substituted with halogen.

In other preferred embodiment of formula (II), NR$_6$R$_6$ in W is:

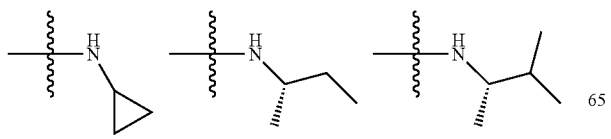

More preferably, NR$_6$R$_6$ is:

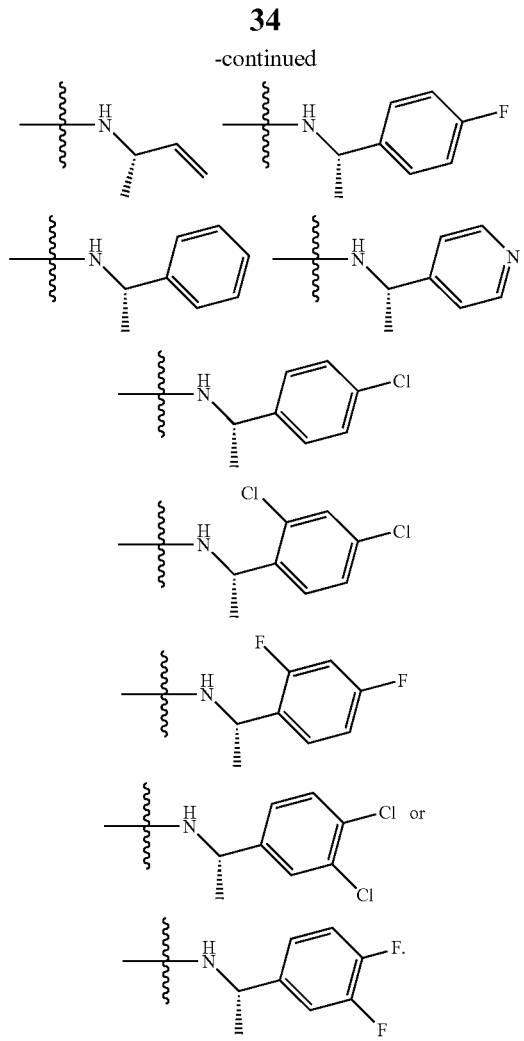

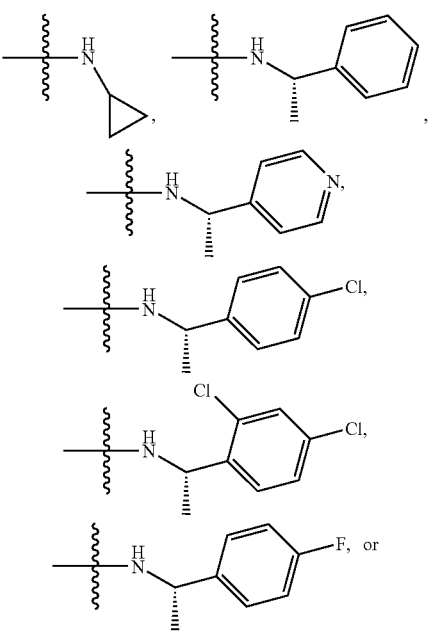

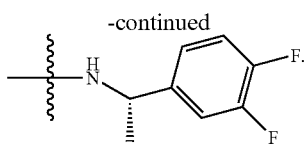

Even more preferably, $NR_6R_6$ is:

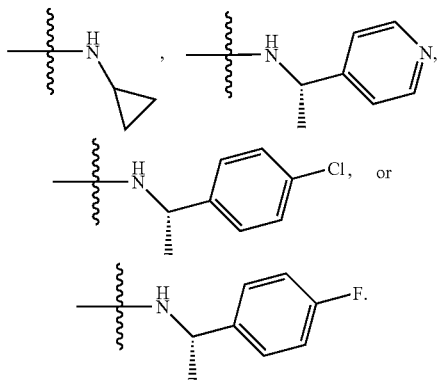

Most preferably, $NR_6R_6$ is:

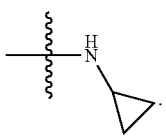

According to another preferred embodiment, when W is —$B(R_7)_2$, each $R_7$ is selected from hydroxy, alkoxy, or aryloxy.

According to yet another preferred embodiment, when W is —$B(R_7)_2$, each $R_7$ is selected from an oxygen atom linked to an aliphatic group and, together with the boron to which they are each bound, the two $R_7$ groups form a 5-8 membered ring.

According to another preferred embodiment, V is a bond, —$CH(R_8)$—, —$N(R_8)$—, —O—, —O—$CH(R_8)$, —S—, —S—$CH(R_8)$, —C(O)—, —C(O)—O—, —C(O)—S—, —C(O)—$CHR_8$—, —$C(O)N(R_8)$—, —S(O)—, —S(O)—$CH(R_8)$—, —$S(O)N(R_8)$—, —S(O)—$N(R_8)$—$CHR_8$, —$S(O)_2$—, —S—$(O)_2$—$CH(R_8)$—, —$S(O)_2N(R_8)$—, or —$S(O)_2$—$N(R_8)$—$CHR_8$; wherein $R_8$ is hydrogen or —(C1-C3)alkyl;

According to another preferred embodiment, V is —NH—.

According to yet another preferred embodiment, V is —C(O)—.

According to yet another preferred embodiment, V is —C(O)—$NR_8$—. More preferably, V is —C(O)—NH—.

According to yet another preferred embodiment T is a heterocyclyl or heteroaryl, optionally having up to 3 substituents as defined above.

According to yet another preferred embodiment, T is a —(C5-C10)heteroaryl.

According to yet another preferred embodiment, T is selected from 3-1H-benzimidazol-2-one, 3-(1-alkyl)-benzimidazol-2-one, 2-tetrahydrofuranyl, 3-tetrahydrofuranyl, pyrazolinyl, 1,3-dihydro-imidazol-2-one, 2-imidazolyl, 4-imidazolyl, 5-imidazolyl, 2-oxazolyl, 4-oxazolyl, 5-oxazolyl, 2-pyrrolyl, 3-pyrrolyl, 2-pyrimidinyl, 4-pyrimidinyl, 5-pyrimidinyl, 5-tetrazolyl, pyrazolyl, pyrazinyl or 1,3,5-triazinyl.

Even more preferably, T is selected from 3-1H-benzimidazol-2-one, 3-(1-alkyl)-benzimidazol-2-one, pyrazolinyl, 1,3-dihydro-imidazol-2-one, 2-imidazolyl, 2-pyrrolyl, 2-pyrimidinyl, 5-pyrimidinyl, 5-tetrazolyl or pyrazinyl.

Most preferred is when T or $R^7$ is selected from:

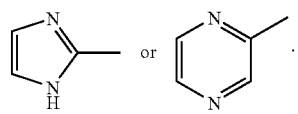

Preferred substituents on T in the above embodiments are halogen, —$CF_3$, —$OCF_3$, oxo, —COOR', or —CON(R')$_2$, wherein R' is as defined above.

According to another preferred embodiment of 5 this invention, T contains at least one hydrogen bond donor moiety selected from —$NH_2$, —NH—, —OH, and —SH.

In a preferred embodiment, T is:

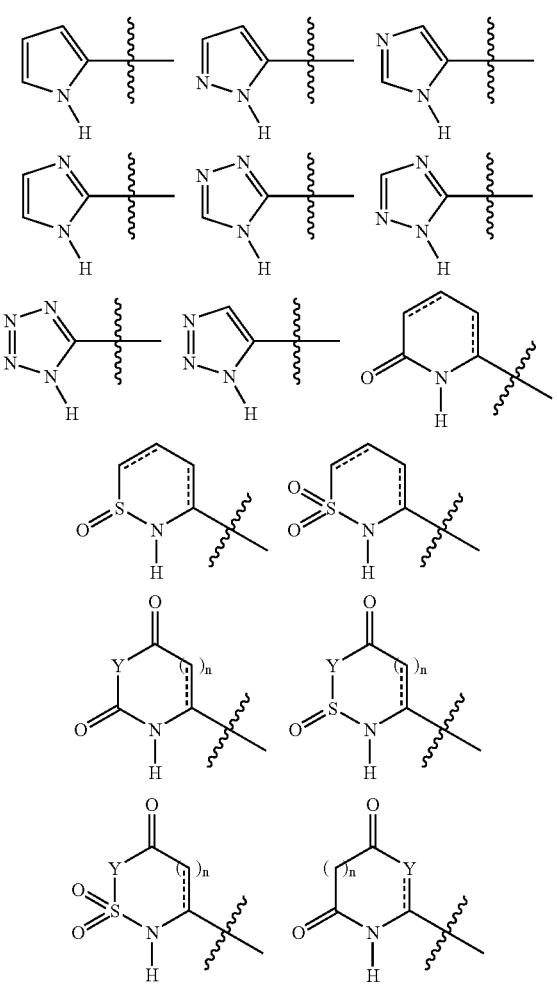

-continued

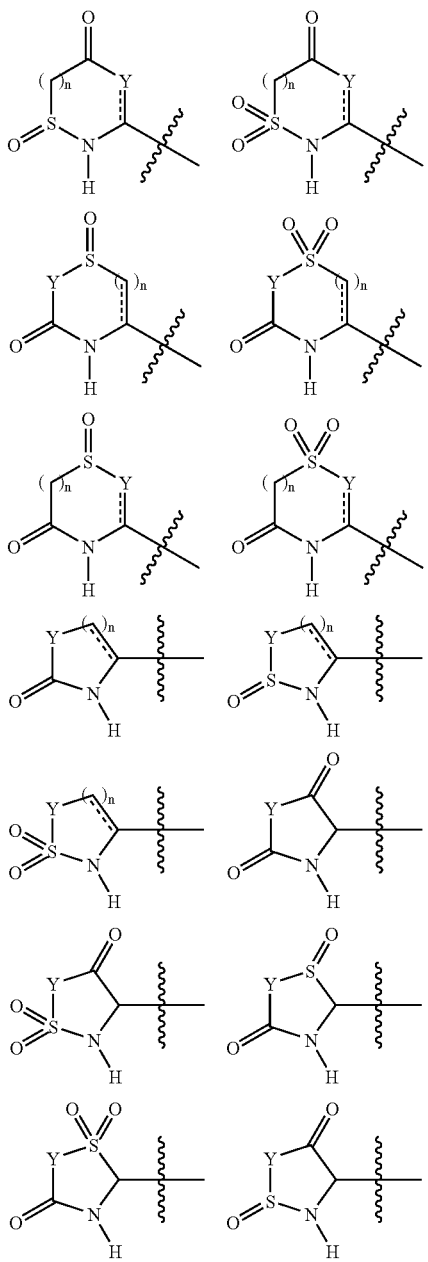

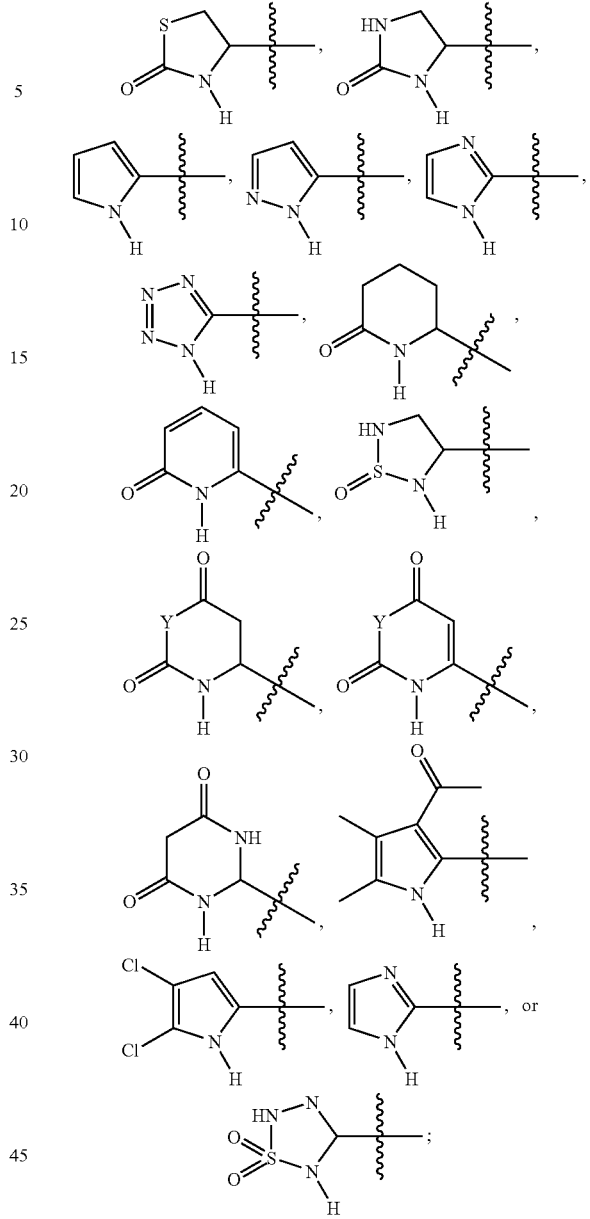

wherein Y is as defined above.

More preferably T is

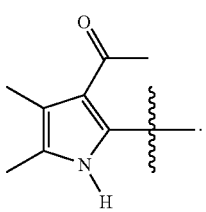

wherein:

T is optionally substituted with up to 3 J substituents, wherein J is as defined in claim 1;

Y is independently O, S, NR$_{10}$, or C(R$_{10}$)$_2$;

n is independently 1 or 2; and

----- independently a single bond or a double bond.

In another preferred embodiment, T is:

According to yet another preferred embodiment, T is:
(C6-C10)-aryl,
(C6-C10)-aryl-(C1-C12)aliphatic,
(C3-C10)-cycloalkyl or -cycloalkenyl,

[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic, wherein each T is optionally substituted with up to 3 J substituents.

According to yet another preferred embodiment of this invention, T:

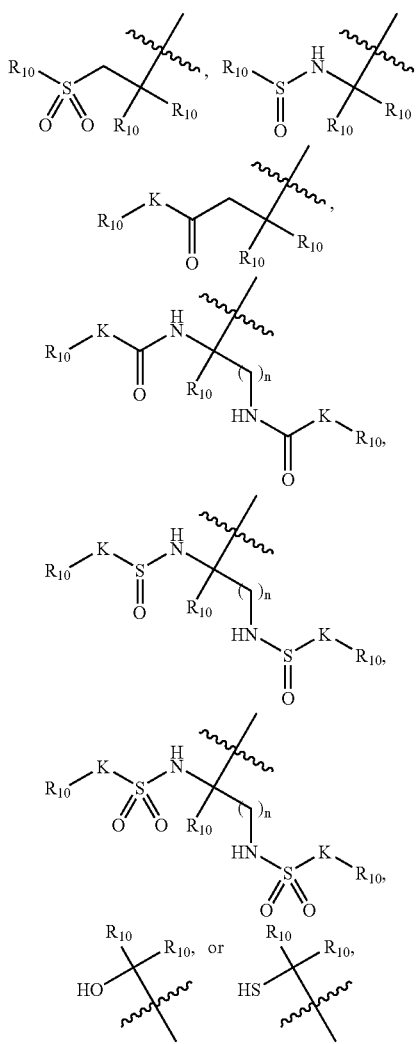

wherein:
$R_{10}$ is:
hydrogen,
(C1-C12)-aliphatic,
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic, wherein each T is optionally substituted with up to 3 J substituents;.
K is a bond, —O—, —S—, —$NR_9$—, —C(O)—, or —C(O)—$NR_9$—, wherein $R_9$ is hydrogen or C1-C12 aliphatic; and
n is 1-3.

More preferably, T is:

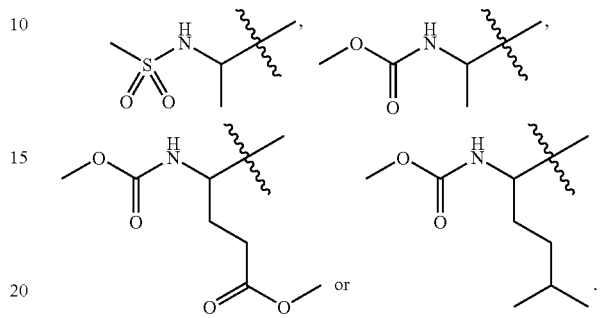

According to another embodiment, the present invention provides compounds of formula (III):

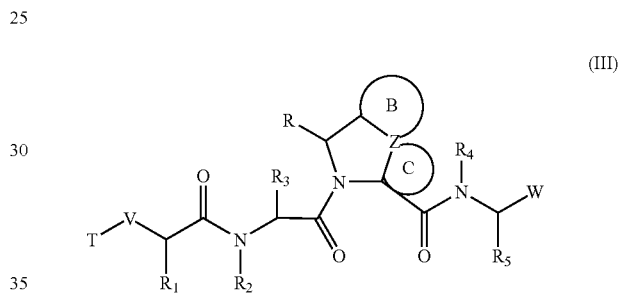

(III)

wherein:
ring B is a carbocyclic or heterocyclic ring, wherein ring B is optionally fused to a carbocyclic, heterocyclic or heteroaryl ring;
wherein ring B has up to 3 substituents selected independently from J;
ring C is a cycloalkyl or heterocyclic ring;
wherein ring C has up to 3 substituents selected independently from J;
z is a carbon atom, —CHR—N—, —HN—CR— or —CHR—CHR—;
wherein, rings B and C are attached to the same carbon atom in Z; or
rings B and C are attached vicinally to Z when Z is —CHR—N—, —HN—CR— or —CHR—CHR—;
wherein R is aliphatic, aryl, aralkyl or cycloalkyl;
J is halogen, —OR', —$NO_2$, —$CF_3$, —$OCF_3$, —R', oxo, —O-benzyl, —O-phenyl, 1,2-methylenedioxy, 1,2-ethylenedioxy, —N(R')$_2$, —SR', —SOR', —$SO_2$R', —C(O)R', —OC(O)R', —COOR' or —CON(R')$_2$, wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;

$R_1$ and $R_3$ are independently:

(C1-C12)-aliphatic, (C3-C10)-cycloalkyl or -cycloalkenyl, (C1-C12)-aliphatic-[(C3-C10)-cycloalkyl or -cycloalkenyl], (C6-C10)-aryl, (C6-C10)-aryl-(C1-C12)aliphatic, (C3-C10)-heterocyclyl, (C6-C10)-heterocyclyl-(C1-C12)aliphatic, (C5-C10)-heteroaryl, or (C5-C10)-heteroaryl-(C1-C12)-aliphatic, wherein each of $R_1$ and $R_3$ is independently and optionally substituted with up to 3 substituents independently selected from J;

wherein up to 3 aliphatic carbon atoms in $R_1$ and $R_3$ may be replaced by a heteroatom selected from O, NH, S, SO, or $SO_2$ in a chemically stable arrangement;

$R_2$ and $R_4$ are independently hydrogen, (C1-C12)-aliphatic, (C3-C10)-cycloalkyl-(C1-C12)-aliphatic, or (C6-C10)aryl-(C1-C12)-aliphatic, wherein each of $R_2$ and $R_4$ is independently and optionally substituted with up to 3 substituents independently selected from J;

wherein up to two aliphatic carbon atoms in $R_2$ and $R_4$ may be replaced by a heteroatom selected from O, NH, S, SO, or $SO_2$ in a chemically stable arrangement;

$R_5$ is —(C1-C12) aliphatic, wherein any hydrogen is optionally substituted with halogen, and wherein any hydrogen or halogen atom bound to any terminal carbon atom of $R_5$ is optionally substituted with sulfhydryl or hydroxy;

W is selected from: —C(O)OH;

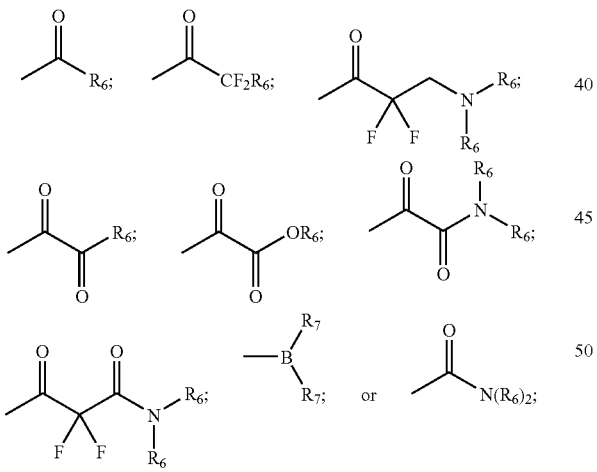

wherein each $R_6$ is independently:

hydrogen, (C1-C12)-aliphatic, (C1-C12)-aliphatic-[(C3-C10)-cycloalkyl or -cycloalkenyl], (C6-C10)-aryl, (C6-C10)-aryl-(C1-C12)aliphatic, (C3-C10)-cycloalkyl or -cycloalkenyl, (C3-C10)-heterocyclyl, (C3-C10)-heterocyclyl-(C1-C12)-aliphatic, (C5-C10)heteroaryl, or (C5-C10)heteroaryl-(C1-C12)-aliphatic, or two $R_6$ groups, which are bound to the same nitrogen atom, form together with that nitrogen atom, a (C3-C10)-heterocyclic ring;

wherein $R_6$ is optionally substituted with up to 3 J substituents;

each $R_7$ is hydroxy, alkoxy, or aryloxy; or each $R_7$ is an oxygen atom linked to an aliphatic group and, together with the boron to which they are each bound, the two $R_7$ groups form a 3-6 membered ring;

V is a bond, —CH($R_8$)—, —N($R_8$)—, —O—, —O—CH($R_8$), —CH($R_8$)—O—, —S—, —S—CH($R_8$)—, —CH($R_8$)—S—, —C(O)—, —C(O)—O—, —O—C(O)—, —C(O)—S—, —C(O)—CH$R_8$—, —CH$R_8$—C(O)—N($R_8$)C(O)—, —C(O)N($R_8$)—, —S(O)—, —S(O)—CH($R_8$), —CH($R_8$)—S(O)—, —S(O)N($R_8$)—, —N($R_8$)S(O)—, —S(O)—N($R_8$)—CH$R_8$, —N($R_8$)—S(O)—CH$R_8$—, —CH$R_8$—S(O)$_2$, —S(O)$_2$—CH($R_8$)—, —CH($R_8$)—S(O)$_2$—, —S(O)$_2$N($R_8$)—, —N($R_8$)—S(O)$_2$—, —S(O)$_2$—N($R_8$)—CH$R_8$ or —N($R_8$)—S(O)$_2$—CH$R_8$;

wherein $R_8$ is hydrogen or (C1-C12)-aliphatic;

T is selected from:

(C6-C10)-aryl, (C6-C10)-aryl-(C1-C12)aliphatic, (C3-C10)-cycloalkyl or -cycloalkenyl, (C1-C12)-aliphatic-[(C3-C10)-cycloalkyl or -cycloalkenyl], (C3-C10)-heterocyclyl, (C3-C10)-heterocyclyl-(C1-C12)-aliphatic, (C5-C10)heteroaryl, or (C5-C10)heteroaryl-(C1-C12)-aliphatic; or T is selected from:

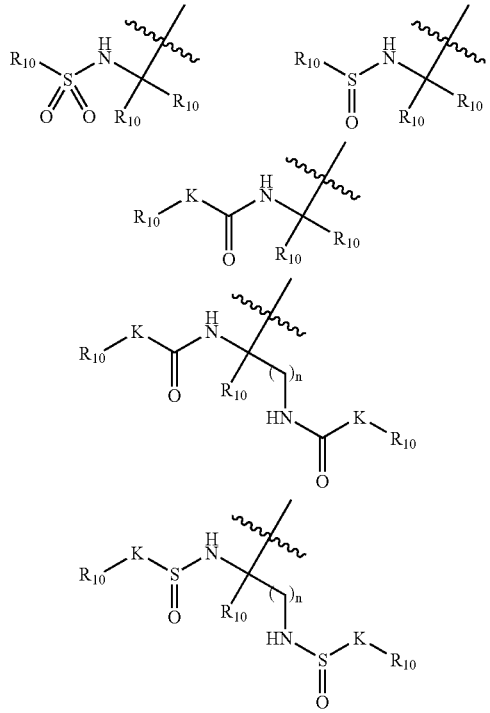

-continued

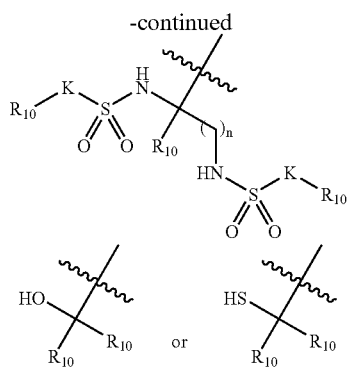

wherein:
R$_{10}$ is:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic,
wherein each T is optionally substituted with up to 3 J substituents;
K is a bond, (C1-C12)-aliphatic, —O—, —S—, —NR$_9$—, —C(O)—, or —C(O)—NR$_9$—, wherein R$_9$ is hydrogen or (C1-C12)-aliphatic; and
n is 1-3.

According to a preferred embodiment, R$_1$ is selected from —(C1-C10)alkyl, —(C3-C7)cycloalkyl, or —((C1-C6)alkyl)-((C3-C7)cycloalkyl). More preferably, R$_1$ is selected from:

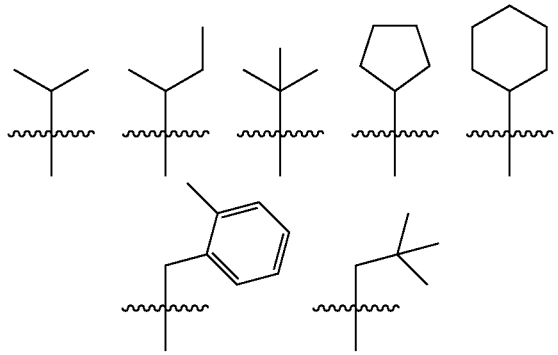

Even more preferably, R$_1$ is selected from —CH$_2$—C C(CH$_3$)$_3$, —C(CH$_3$)$_3$, —CH(CH$_3$)$_2$, —CH(CH$_3$)—CH$_2$—CH$_3$, or cyclohexyl. Most preferably R$_1$ is cyclohexyl.

According to another preferred embodiment, R$_2$ is (C1-C12)-aliphatic. More preferably, R$_2$ is selected from hydrogen, methyl, ethyl or propyl. Even more preferably, R$_2$ is hydrogen or methyl. Most preferably, R$_2$ is hydrogen.

According to another preferred embodiment, R$_3$ is selected from —(C1-C10)alkyl, —(C3-C7)cycloalkyl, or —((C1-C6)alkyl)-((C3-C7)cycloalkyl).

More preferably, R$_3$ is selected from:

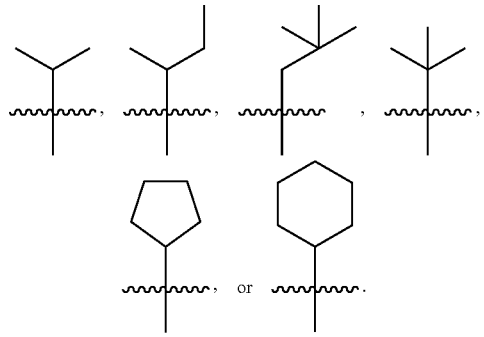

Even more preferably, R$_3$ is selected from —C(CH$_3$)$_2$, —CH(CH$_3$)$_2$, —CH (CH$_3$)—CH$_2$—CH$_3$, or cyclohexyl. Most preferably, R$_3$ is selected from —C(CH$_3$)$_3$ or —CH (CH$_3$)$_2$.

According to another preferred embodiment, R$_4$ is (C1-C12)-aliphatic. More preferably, R$_4$ is selected from hydrogen, methyl, ethyl or propyl. Even more preferably, R$_4$ is selected from hydrogen.

According to another preferred embodiment, R$_5$ is —(C2-C7)alkyl optionally substituted with halogen. Preferably, R$_5$ is selected from:

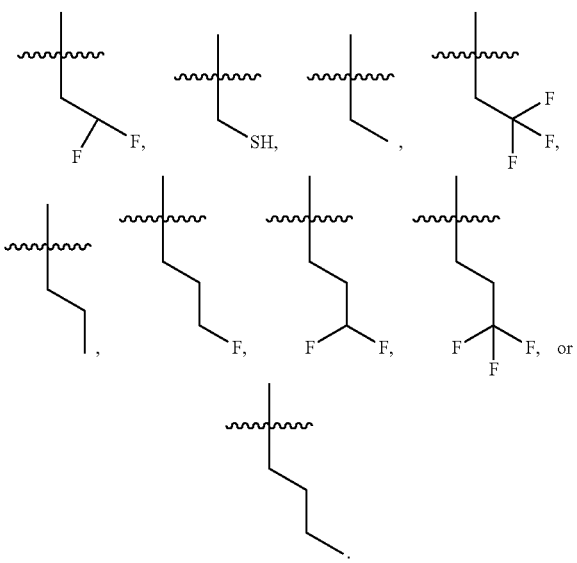

More preferably, R$_5$ is selected from —CH$_2$CH$_2$CH$_3$, —CH$_2$CH$_2$CH$_2$CH$_3$, —CH$_2$CH$_2$CH$_2$F, —CH$_2$CH$_2$CHF$_2$, or —CH$_2$CH$_2$CF$_3$. Even more preferably, R$_5$ is selected from —CH$_2$CH$_2$CH$_3$, —CH$_2$CH$_2$CH$_2$CH$_3$ or —CH$_2$CH$_2$CHF$_2$. Most preferably, R$_5$ is —CH$_2$CH$_2$CH$_3$ or —CH$_2$CH$_2$CH$_2$CH$_3$.

According to another preferred embodiment W is selected from: CHO, —C(O)—R$_6$, —CO$_2$H, —C(O)—C(O)—R$_6$, or —C(O)—C(O)—NH(R$_6$), wherein R$_6$ is selected from hydrogen, aryl, heteroaryl, heterocyclyl, C3-C6 alkyl, C3-C6 cycloalkyl, hydroxy, —O—C1-C6 alkyl, wherein —NH(R$_6$) is selected from —NH—(C3-C6 cycloalkyl), NH-aralkyl, —NH-alkylheteroaryl, —NH-alkylheterocyclyl, and wherein said aryl, heterocyclyl or heteroaryl is optionally substituted with up to 3 halogen atoms.

More preferably, R$_6$ or —NH(R$_6$) is selected from:

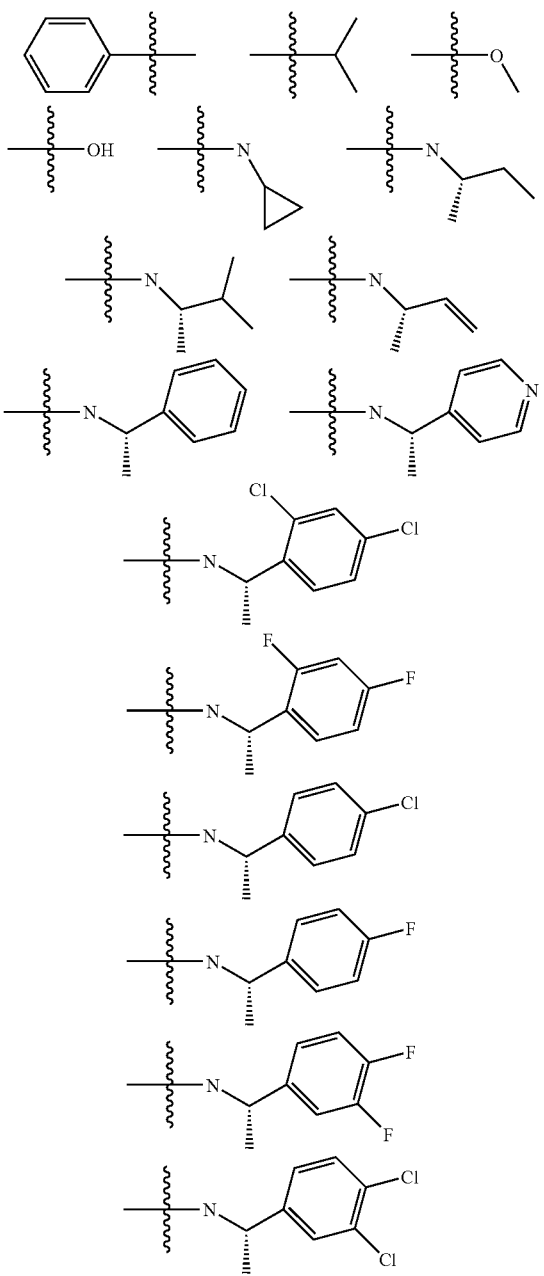

According to another preferred embodiment w is selected from —C(O)OH or —C(O)—C(O)—R$_6$. More preferably, W is —C(O)—C(O)—R$_6$. Preferably, R$_6$ is isopropyl.

According to a preferred embodiment, W is —C(O)—C(O)—R$_6$. Preferably, R$_6$ is isopropyl.

According to another preferred embodiment, W is —C(O)—C(O)—OR$_6$. Preferably, R$_6$ is hydrogen, (C1-C12)-aliphatic, (C6-C10)-aryl, (C3-C10)-cycloalkyl or -cycloalkenyl, (C3-C10)-heterocyclyl or (C5-C10)heteroaryl. More preferably, R$_6$ is H or methyl.

According to yet another preferred embodiment, W is —C(O)—C(O)—N(R$_6$)$_2$. Preferably, R$_6$ is hydrogen, (C3-C10)-cycloalkyl or -cycloalkenyl, or (C3-C10)-heterocyclyl.

In another preferred embodiment of compounds of formula (III) is where W is C(O)—C(O)—N(R$_6$)$_2$, the NR$_6$R$_6$ portion of the W moiety is —NH—(C3-C6)cycloalkyl, —NH—CH(CH$_3$)—(C6-C10)aryl or —NH—CH(CH$_3$)—(C3-C10)heterocyclyl, or —NH—CH(CH$_3$)—(C5-C10)heteroaryl, wherein said aryl, heterocyclyl, or heteroaryl is optionally substituted with halogen.

Alternatively, the NR$_6$R$_6$ portion is —NH—(C3-C6)cycloalkyl, —NH—CH(CH$_3$)—(C6-C10)aryl, or —NH—CH(CH$_3$)—(C5-C10)heteroaryl, wherein said aryl or said heterocyclyl is optionally substituted with halogen; or NR$_6$R$_6$ is —NH—(C3-C6) cycloalkyl, —NH—CH(CH$_3$)—(C6-C10) aryl, or —NH—CH(CH$_3$)—(C3-C10)heterocyclyl, wherein said aryl or said heterocyclyl is optionally substituted with halogen.

In other preferred embodiment of formula (III), NR$_6$R$_6$ in W is:

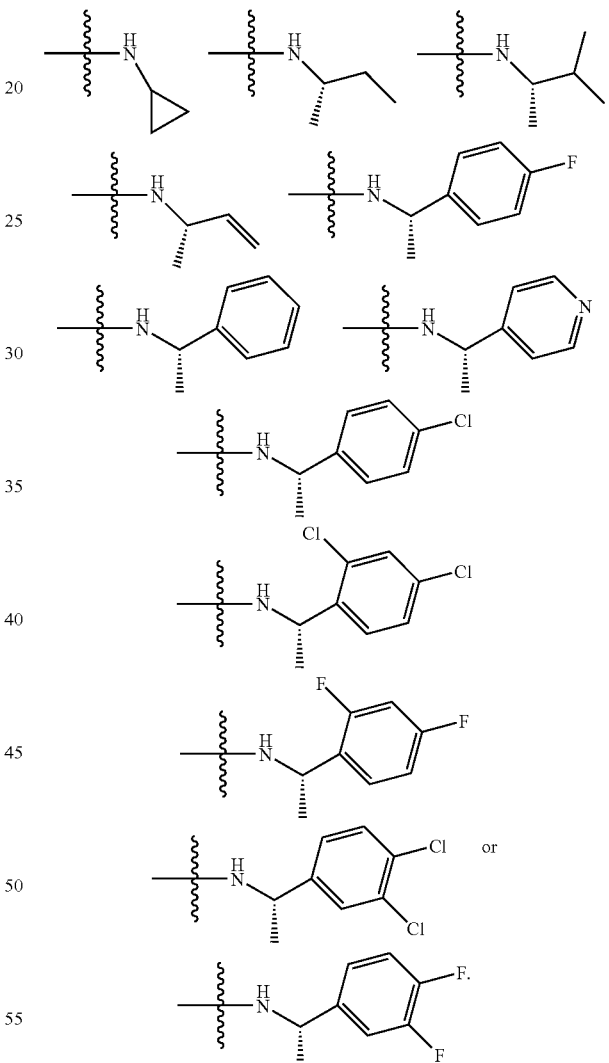

More preferably, NR$_6$R$_6$ is:

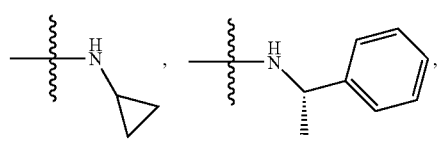

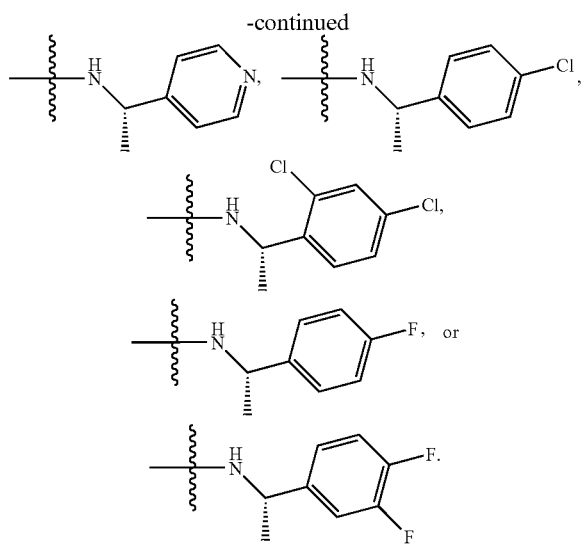

Even more preferably, NR$_6$R$_6$ is:

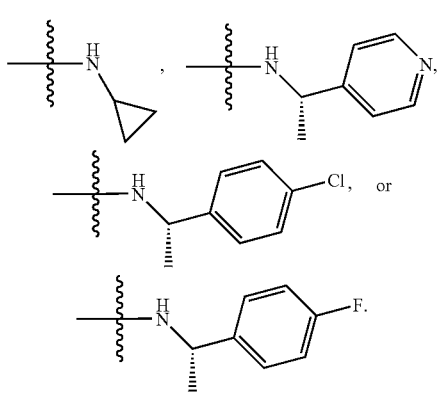

Most preferably, NR$_6$R$_6$ is:

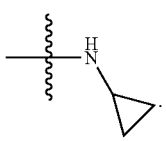 [SMILES: *NC1CC1]

According to another preferred embodiment, when W is —B(R$_7$)$_2$, each R$_7$ is selected from hydroxy, alkoxy, or aryloxy.

According to yet another preferred embodiment, when W is —B(R$_7$)$_2$, each R$_7$ is selected from an oxygen atom linked to an aliphatic group and, together with the boron to which they are each bound, the two R$_7$ groups form a 5-8 membered ring.

According to another preferred embodiment, V is a bond, —CH(R$_8$)—, —N(R$_8$)—, —O—, —O—CH(R$_8$), —S—, —S—CH(R$_8$), —C(O)—, —C(O)—O—, —C(O)—S—, —C(O)—CHR$_8$—, —C(O)N(R$_8$)—, —S(O)—, —S(O)—CH(R$_8$)—, —S(O)N(R$_8$)—, —S(O)—N(R$_8$)—CHR$_8$, —S(O)$_2$, —S—(O)$_2$—CH(R$_8$)—, —S(O)$_2$N(R$_8$)—, or —S(O)$_2$—N(R$_8$)—CHR$_8$; wherein R$_8$ is hydrogen or —(C1-C3)alkyl;

According to another preferred embodiment, V is —NH—.

According to yet another preferred embodiment, V is —C(O)—.

According to yet another preferred embodiment, V is —C(O)—NR$_8$—. More preferably, V is —C(O)—NH—.

According to yet another preferred embodiment T is a heterocyclyl or heteroaryl, optionally having up to 3 substituents as defined above.

According to yet another preferred embodiment, T is a —(C5-C10)heteroaryl.

According to yet another preferred embodiment, T is selected from 3-1H-benzimidazol-2-one, 3-(1-alkyl)-benzimidazol-2-one, 2-tetrahydrofuranyl, 3-tetrahydrofuranyl, pyrazolinyl, 1,3-dihydro-imidazol-2-one, 2-imidazolyl, 4-imidazolyl, 5-imidazolyl, 2-oxazolyl, 4-oxazolyl, 5-oxazolyl, 2-pyrrolyl, 3-pyrrolyl, 2-pyrimidinyl, 4-pyrimidinyl, 5-pyrimidinyl, 5-tetrazolyl, pyrazolyl, pyrazinyl or 1,3,5-triazinyl.

Even more preferably, T is selected from 3-1H-benzimidazol-2-one, 3-(1-alkyl)-benzimidazol-2-one, pyrazolinyl, 1,3-dihydro-imidazol-2-one, 2-imidazolyl, 2-pyrrolyl, 2-pyrimidinyl, 5-pyrimidinyl, 5-tetrazolyl or pyrazinyl.

Most preferred is when T or R$^7$ is selected from:

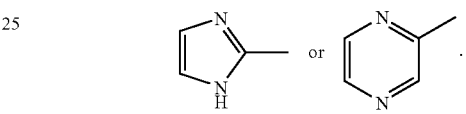

Preferred substituents on T in the above embodiments are halogen, —CF$_3$, —OCF$_3$, oxo, —COOR', or —CON(R')$_2$, wherein R' is as defined above.

According to another preferred embodiment of this invention, T contains at least one hydrogen bond donor moiety selected from —NH$_2$, —NH—, —OH, and —SH.

In a preferred embodiment, T is:

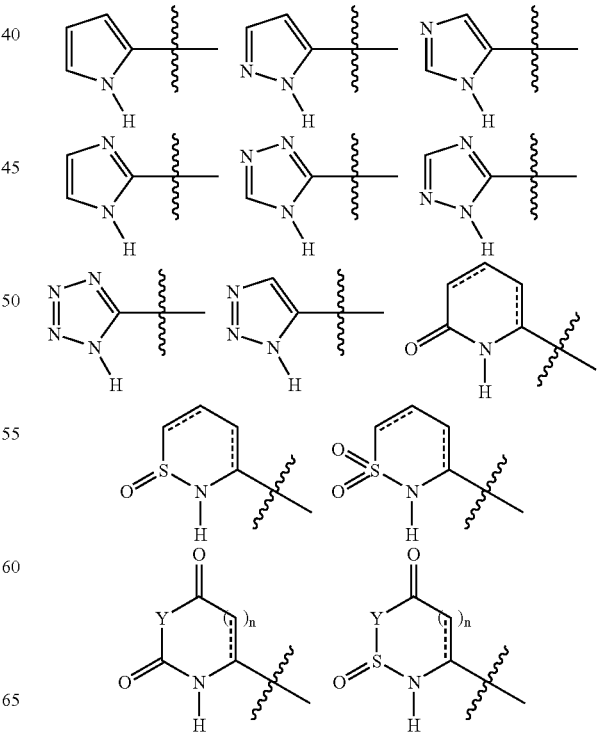

-continued
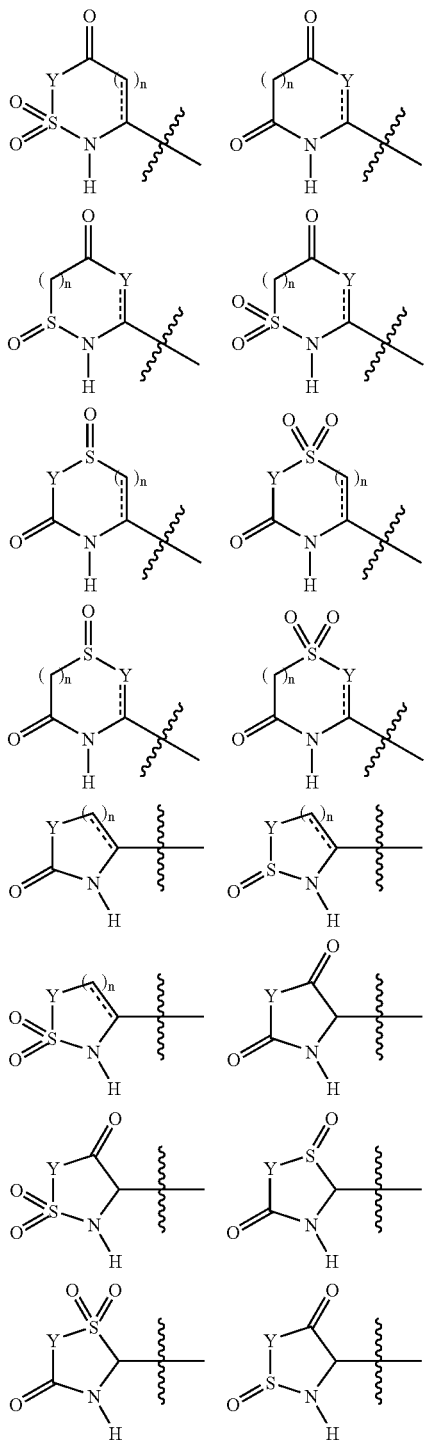
wherein:
T is optionally substituted with up to 3 J substituents, wherein J is as defined in claim 1;
Y is independently O, S, NR$_{10}$, or C(R$_{10}$)$_2$;
n is independently 1 or 2; and
------ is independently a single bond or a double bond.
In another preferred embodiment, T is:
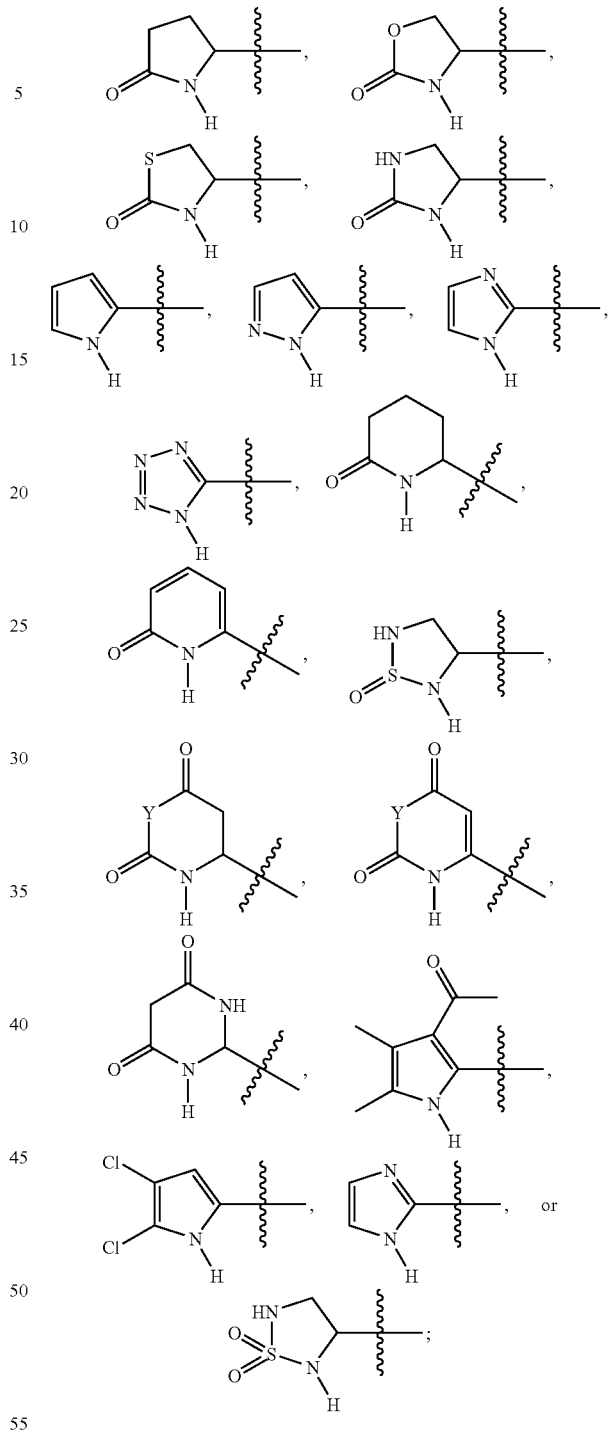
wherein Y is as defined above.
More preferably T is
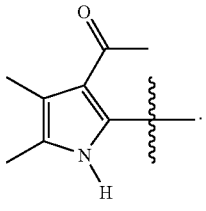

According to yet another preferred embodiment, T is:
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic, (C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic,
wherein each T is optionally substituted with up to 3 J substituents.

According to yet another preferred embodiment of this invention, T:

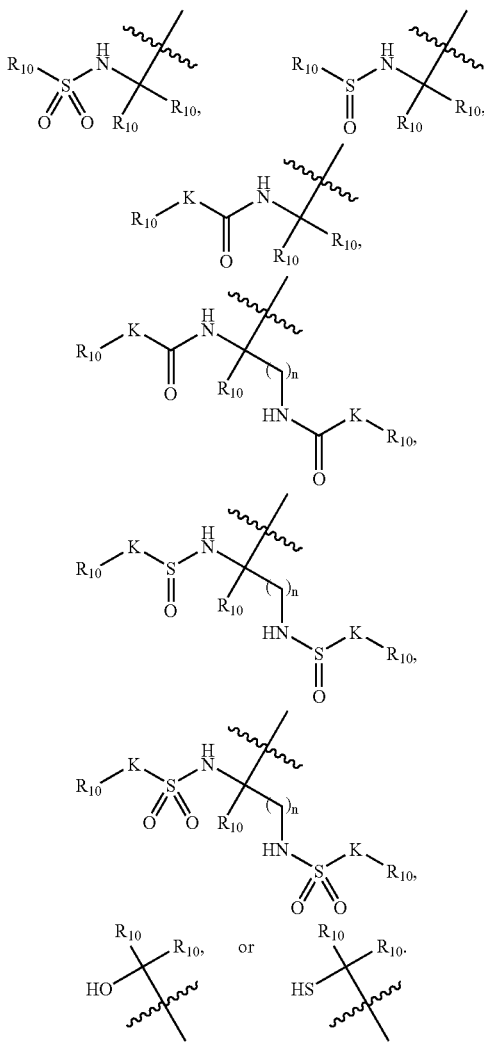

wherein:
R$_{10}$ is:
hydrogen,
(C1-C12)-aliphatic,
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic,
wherein each T is optionally substituted with up to 3 J substituents;
K is a bond, —O—, —S—, —NR$_9$—, —C(O)—, or —C(O)—NR$_9$—, wherein R$_9$ is hydrogen or C1-C12 aliphatic; and
n is 1-3.
More preferably, T is:

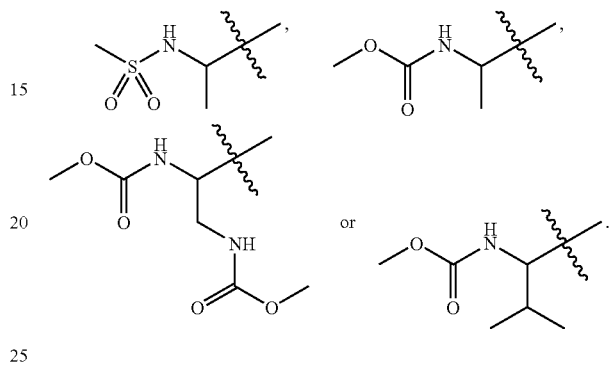

In compounds of formula (III), the preferred embodiments of ring B are as defined for compounds of formula (I).
In compounds of formula (III), the preferred embodiments of ring C are as defined for compounds of formula (II).
According to another embodiment, the present invention provides compounds of formula (IV):

(IV)

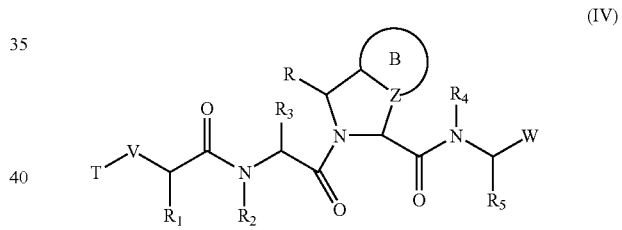

wherein:
ring B is a bridged bicyclic ring system containing 6-12 carbon atoms, wherein ring B is saturated or partially unsaturated; or
the ring system comprising ring B, together with the ring containing Z and the nitrogen atom, contains more than ten ring atoms;
wherein ring B has up to 3 substituents selected independently from J;
J is halogen, —OR', —NO$_2$, —CF$_3$, —OCF$_3$, —R', oxo, —OR', —O-benzyl, —O-phenyl, 1,2-methylenedioxy, 1,2-ethylenedioxy, —N(R')$_2$, —SR', —SOR', —SO$_2$R', —C(O)R', —COOR' or —CON(R')$_2$, wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or (C5-C10)-heteroaryl-(C1-C12)-aliphatic;
$R_1$ and $R_3$ are independently:
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic,
wherein each of $R_1$ and $R_3$ is independently and optionally substituted with up to 3 substituents independently selected from J;
wherein up to 3 aliphatic carbon atoms in $R_1$ and $R_3$ may be replaced by a heteroatom selected from O, NH, S, SO, or $SO_2$ in a chemically stable arrangement;
$R_2$ and $R_4$ are independently hydrogen,
(C1-C12)-aliphatic,
(C3-C10)-cycloalkyl-(C1-C12)-aliphatic, or
(C6-C10)aryl-(C1-C12)-aliphatic,
wherein each of $R_2$ and $R_4$ is independently and optionally substituted with up to 3 substituents independently selected from J;
wherein up to two aliphatic carbon atoms in $R_2$ and $R_4$ may be replaced by a heteroatom selected from O, NH, S, SO, or $SO_2$ in a chemically stable arrangement;
Z is a carbon atom, —CHR—N—, —HN—CR— or —CHR—CHR—, —O—CHR—, —S—CHR—, —SO—CHR—, —$SO_2$—CHR—, or —N—;
wherein R is aliphatic, aryl, aralkyl or cycloalkyl;
$R_5$ is —(C1-C12) aliphatic, wherein any hydrogen is optionally substituted with halogen, and wherein any hydrogen or halogen atom bound to any terminal carbon atom of $R_5$ is optionally substituted with sulfhydryl or hydroxy;
W is selected from: —C(O)OH;

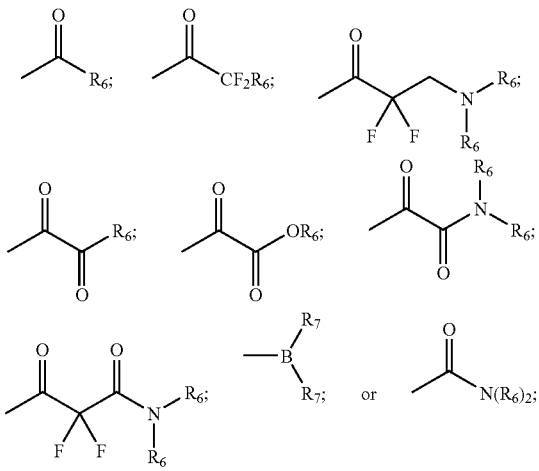

wherein each $R_6$ is independently:
hydrogen,
(C1-C12)-aliphatic, (C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic, or
two $R_6$ groups, which are bound to the same nitrogen atom, form together with that nitrogen atom, a (C3-C10)-heterocyclic ring;
wherein $R_6$ is optionally substituted with up to 3 J substituents;
each $R_7$ is hydroxy, alkoxy, or aryloxy; or
each $R_7$ is an oxygen atom linked to an aliphatic group and, together with the boron to which they are each bound, the two $R_7$ groups form a 3-6 membered ring;
V is a bond, —CH($R_8$)—, —N($R_8$)—, —O—, —O—CH($R_8$), —CH($R_8$)—O—, —S—, —S—CH($R_8$)—, —CH($R_8$)—S—, —C(O)—, —C(O)—O—, —O—C(O)—, —C(O)—S—, —C(O)—CHR$_8$—, —CHR$_8$—C(O)—, —N($R_8$)C(O)—, —C(O)N($R_8$)—, —S(O)—, —S(O)—CH($R_8$), —CH($R_8$)—S(O)—, —S(O)N($R_8$)—, —N($R_8$)S(O)—, —S(O)—N($R_8$)—CHR$_8$, —N($R_8$)—S(O)—CHR$_8$—, —CHR$_8$—S(O)$_2$, —S(O)$_2$—CH($R_8$)—, —CH($R_8$)—S(O)$_2$—, —S(O)$_2$N($R_8$)—, —N($R_8$)—S(O)$_2$—, —S(O)$_2$—N($R_8$)—CHR$_8$ or —N($R_8$)—S(O)$_2$—CHR$_8$;
wherein $R_8$ is hydrogen or (C1-C12)-aliphatic;
T is selected from:
(C6-C10)-aryl,
(C6-C10)-aryl-(C1-C12)aliphatic,
(C3-C10)-cycloalkyl or -cycloalkenyl,
(C1-C12)-aliphatic-[(C3-C10)-cycloalkyl or -cycloalkenyl],
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic; or
T is selected from:

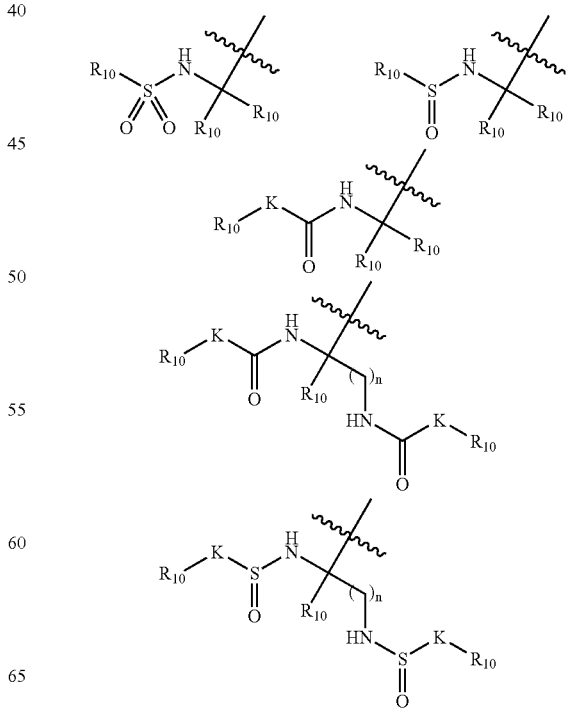

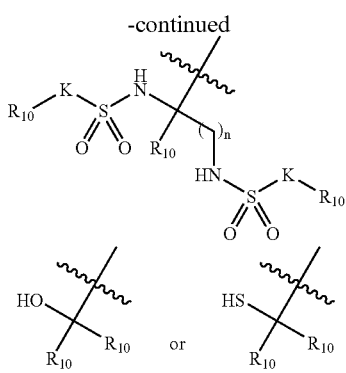

wherein:
R$_{10}$ is:
hydrogen,
(C1-C12)-aliphatic,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-cycloalkyl or -cycloalkenyl,
(C3-C10)-heterocyclyl,
(C3-C10)-heterocyclyl-(C1-C12)-aliphatic,
(C5-C10)-heteroaryl, or
(C5-C10)-heteroaryl-(C1-C12)-aliphatic,
wherein each T is optionally substituted with up to 3 J substituents;
K is a bond, (C1-C12)-aliphatic, —O—, —S—, —NR$_9$—, —C(O)—, or —C(O)—NR$_9$—, wherein R$_9$ is hydrogen or (C1-C12)-aliphatic; and
n is 1-3.

According to a preferred embodiment of compounds of formula (IV), ring B is a bridged bicyclic ring system containing 6-12 carbon atoms, wherein ring B is saturated or partially unsaturated, and ring B has up to 3 substituents selected independently from J.

Preferred embodiments of ring B in compound of formula (IV) include:

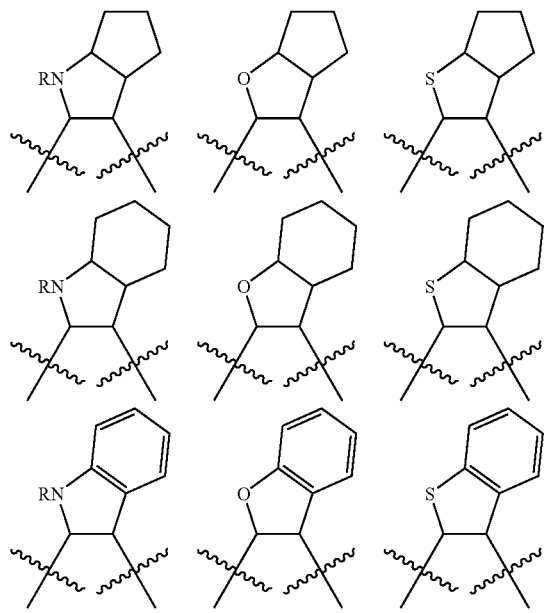

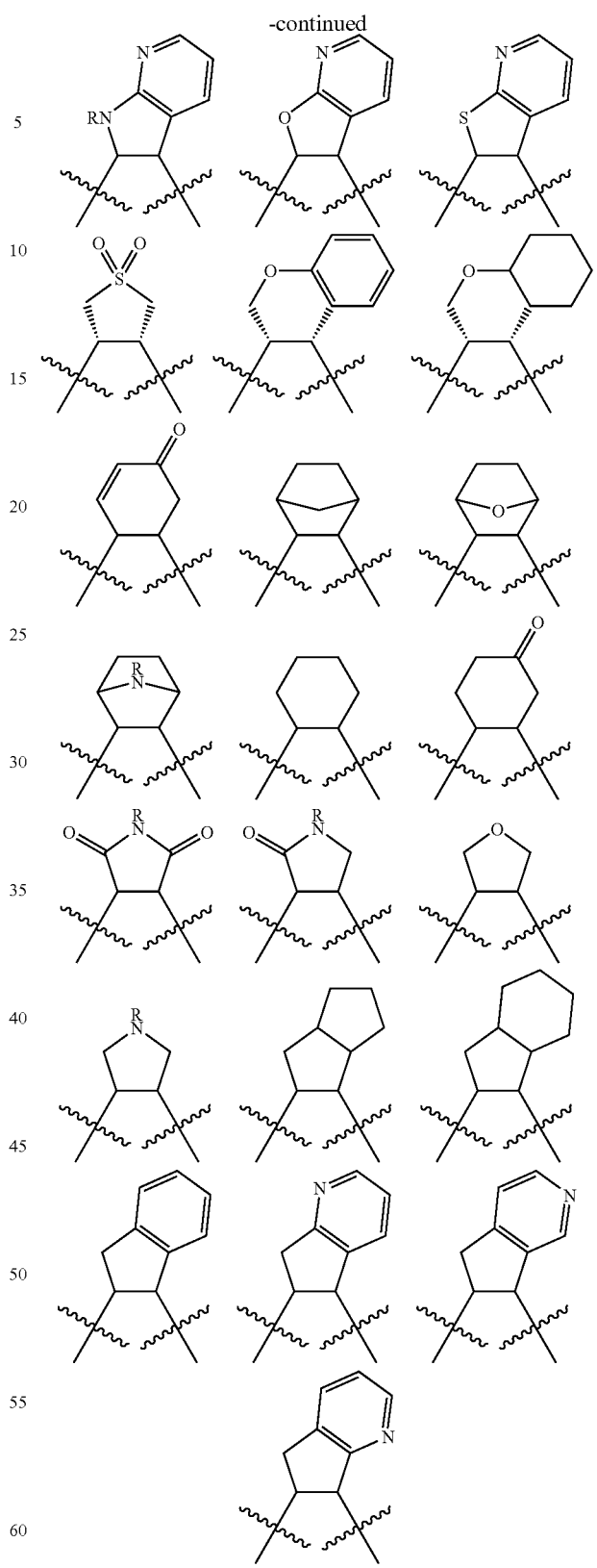

According to a preferred embodiment, R$_1$ is selected from —(C1-C10)alkyl, —(C3-C7)cycloalkyl, or —((C1-C6)alkyl)-((C3-C7)cycloalkyl). More preferably, R$_1$ is selected from:

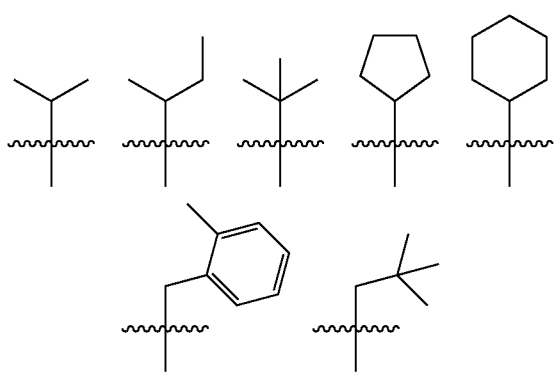

Even more preferably, $R_1$ is selected from —$CH_2$—C$C(CH_3)_3$, —$C(CH_3)_3$, —$CH(CH_3)_2$, —$CH(CH_3)$—$CH_2$—$CH_3$, or cyclohexyl. Most preferably $R_1$ is cyclohexyl.

According to another preferred embodiment, $R_2$ is (C1-C12)-aliphatic. More preferably, $R_2$ is selected from hydrogen, methyl, ethyl or propyl. Even more preferably, $R_2$ is hydrogen or methyl. Most preferably, $R_2$ is hydrogen.

According to another preferred embodiment, $R_3$ is selected from —(C1-C10)alkyl, —(C3-C7)cycloalkyl, or —((C1-C6)alkyl)-((C3-C7)cycloalkyl).

More preferably, $R_3$ is selected from:

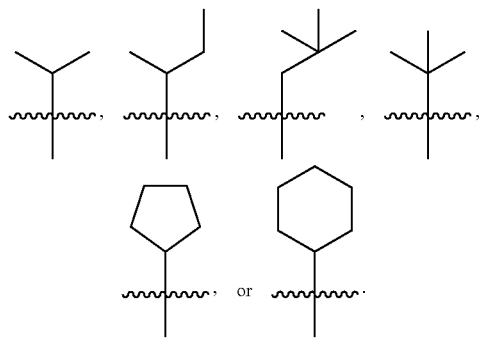

Even more preferably, $R_3$ is selected from —$C(CH_3)_2$, —$CH(CH_3)_2$, —$CH(CH_3)$—$CH_2$—$CH_3$, or cyclohexyl. Most preferably, $R_3$ is selected from —$C(CH_3)_3$ or —$CH(CH_3)_2$.

According to another preferred embodiment, $R_4$ is (C1-C12)-aliphatic. More preferably, $R_4$ is selected from hydrogen, methyl, ethyl or propyl. Even more preferably, $R_4$ is selected from hydrogen.

According to another preferred embodiment, $R_5$ is —(C2-C7)alkyl optionally substituted with halogen. Preferably, $R_5$ is selected from:

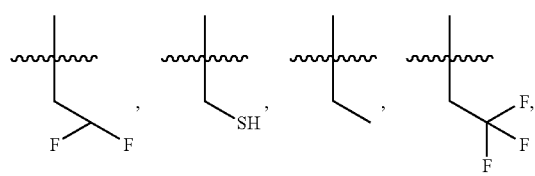

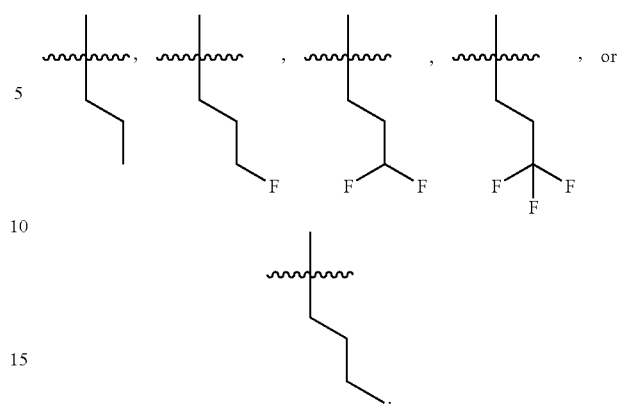

More preferably, $R_5$ is selected from —$CH_2CH_2CH_3$, —$CH_2CH_2CH_2CH_3$, —$CH_2CH_2CH_2F$. —$CH_2CH_2CHF_2$, or —$CH_2CH_2CF_3$. Even more preferably, $R_5$ is selected from —$CH_2CH_2CH_3$, —$CH_2CH_2CH_2CH_3$ or —$CH_2CH_2CHF_2$. Most preferably, $R_5$ is —$CH_2CH_2CH_3$ or —$CH_2CH_2CH_2CH_3$.

According to another preferred embodiment W is selected from: CHO, —C(O)—$R_6$, —$CO_2H$, —C(O)—C(O)—$R_6$, or —C(O)—C(O)—NH($R_6$), wherein $R_6$ is selected from hydrogen, aryl, heteroaryl, heterocyclyl, C3-C6 alkyl, C3-C6 cycloalkyl, hydroxy, —O—C1-C6 alkyl, wherein —NH($R_6$) is selected from —NH—(C3-C6 cycloalkyl), NH-aralkyl, —NH-alkylheteroaryl, —NH-alkylheterocyclyl, and wherein said aryl, heterocyclyl or heteroaryl is optionally substituted with up to 3 halogen atoms.

More preferably, $R_6$ or —NH($R_6$) is selected from:

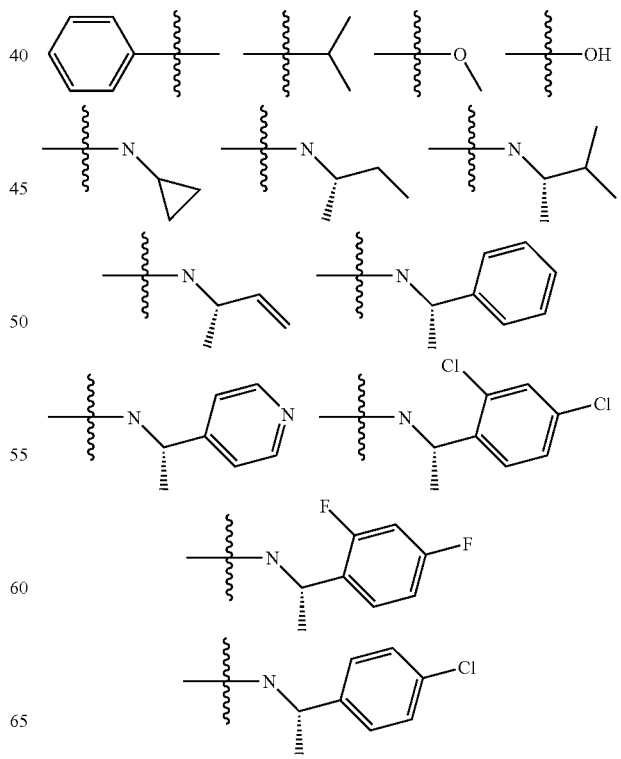

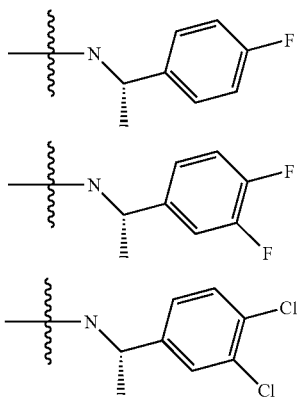

According to another preferred embodiment w is selected from —C(O)OH or —C(O)—C(O)—R₆. More preferably, W is —C(O)—C(O)—R₆. Preferably, R₆ is isopropyl.

According to a preferred embodiment, W is —C(O)—C(O)—R₆. Preferably, R₆ is isopropyl.

According to another preferred embodiment, W is —C(O)—C(O)—OR₆. Preferably, R₆ is hydrogen, (C1-C12)-aliphatic, (C6-C10)-aryl, (C3-C10)-cycloalkyl or -cycloalkenyl, (C3-C10)-heterocyclyl or (C5-C10)heteroaryl. More preferably, R₆ is H or methyl.

According to yet another preferred embodiment, W is —C(O)—C(O)—N(R₆)₂. Preferably, R₆ is hydrogen, (C3-C10)-cycloalkyl or -cycloalkenyl, or (C3-C10)-heterocyclyl.

In another preferred embodiment of compounds of formula (IV) is where W is C(O)—C(O)—N(R₆)₂, the NR₆R₆ portion of the W moiety is —NH—(C3-C6)cycloalkyl, —NH—CH(CH₃)—(C6-C10)aryl or —NH—CH(CH₃)—(C3-C10)heterocyclyl, or —NH—CH(CH₃)—(C5-C10)heteroaryl, wherein said aryl, heterocyclyl, or heteroaryl is optionally substituted with halogen.

Alternatively, the NR₆R₆ portion is —NH—(C3-C6)cycloalkyl, —NH—CH(CH₃)—(C6-C10)aryl, or —NH—CH(CH₃)—(C5-C10)heteroaryl, wherein said aryl or said heterocyclyl is optionally substituted with halogen; or NR₆R₆ is —NH—(C3-C6) cycloalkyl, —NH—CH(CH₃)—(C6-C10)aryl, or —NH—CH(CH₃)—(C3-C10)heterocyclyl, wherein said aryl or said heterocyclyl is optionally substituted with halogen.

In other preferred embodiment of formula I, NR₆R₆ in w is:

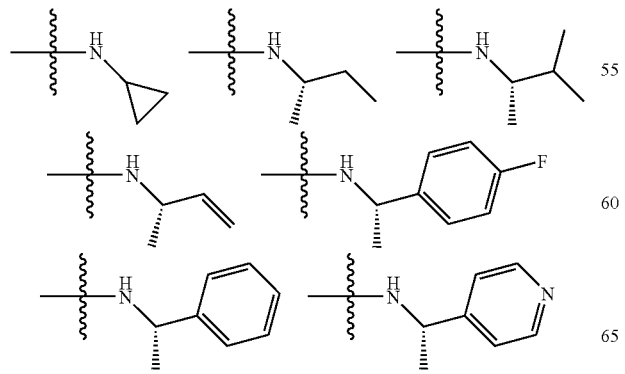

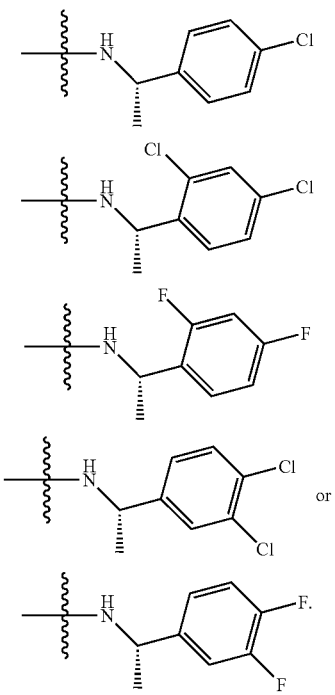

More preferably, NR₆R₆ is:

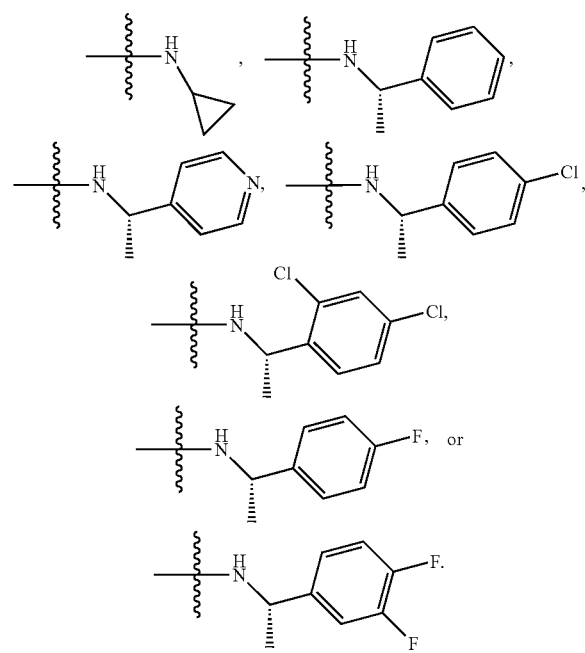

Even more preferably, NR₆R₆ is:

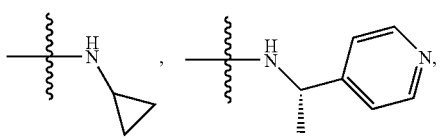

-continued

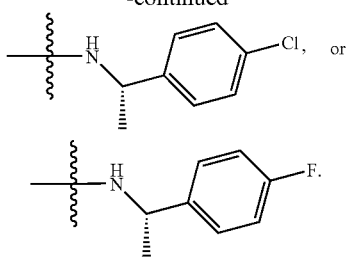

Most preferably, NR$_6$R$_6$ is:

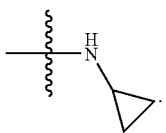 [SMILES: *NC1CC1]

According to another preferred embodiment, when W is —B(R$_7$)$_2$, each R$_7$ is selected from hydroxy, alkoxy, or aryloxy.

According to yet another preferred embodiment, when W is —B(R$_7$)$_2$, each R$_7$ is selected from an oxygen atom linked to an aliphatic group and, together with the boron to which they are each bound, the two R$_7$ groups form a 5-8 membered ring.

According to another preferred embodiment, V is a bond, —CH(R$_8$)—, —N(R$_8$)—, —O—, —O—CH(R$_8$), —S—, —S—CH(R$_8$), —C(O)—, —C(O)—O—, —C(O)—S—, —C(O)—CHR$_8$—, —C(O)N(R$_8$)—, —S(O)—, —S(O)—CH(R$_8$)—, —S(O)N(R$_8$)—, —S(O)—N(R$_8$)—CHR$_8$, —S(O)$_2$—, —S—(O)$_2$—CH(R$_8$)—, —S(O)$_2$N(R$_8$)—, or —S(O)$_2$—N(R$_8$)—CHR$_8$; wherein R$_8$ is hydrogen or —(C1-C3)alkyl;

According to another preferred embodiment, V is —NH—.

According to yet another preferred embodiment, V is —C(O)—.

According to yet another preferred embodiment, V is —C(O)—NR$_8$—. More preferably, V is —C(O)—NH—.

According to yet another preferred embodiment T is a heterocyclyl or heteroaryl, optionally having up to 3 substituents as defined above.

According to yet another preferred embodiment, T is a —(C5-C10)heteroaryl.

According to yet another preferred embodiment, T is selected from 3-1H-benzimidazol-2-one, 3-(1-alkyl)-benzimidazol-2-one, 2-tetrahydrofuranyl, 3-tetrahydrofuranyl, pyrazolinyl, 1,3-dihydro-imidazol-2-one, 2-imidazolyl, 4-imidazolyl, 5-imidazolyl, 2-oxazolyl, 4-oxazolyl, 5-oxazolyl, 2-pyrrolyl, 3-pyrrolyl, 2-pyrimidinyl, 4-pyrimidinyl, 5-pyrimidinyl, 5-tetrazolyl, pyrazolyl, pyrazinyl or 1,3,5-triazinyl.

Even more preferably, T is selected from 3-1H-benzimidazol-2-one, 3-(1-alkyl)-benzimidazol-2-one, pyrazolinyl, 1,3-dihydro-imidazol-2-one, 2-imidazolyl, 2-pyrrolyl, 2-pyrimidinyl, 5-pyrimidinyl, 5-tetrazolyl or pyrazinyl.

Most preferred is when T or R$^7$ is selected from:

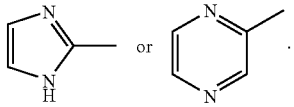

Preferred substituents on T in the above embodiments are halogen, —CF$_3$, —OCF$_3$, oxo, —COOR', or —CON(R')$_2$, wherein R' is as defined above.

According to another preferred embodiment of 5 this invention, T contains at least one hydrogen bond donor moiety selected from —NH$_2$, —NH—, —OH, and —SH.

In a preferred embodiment, T is:

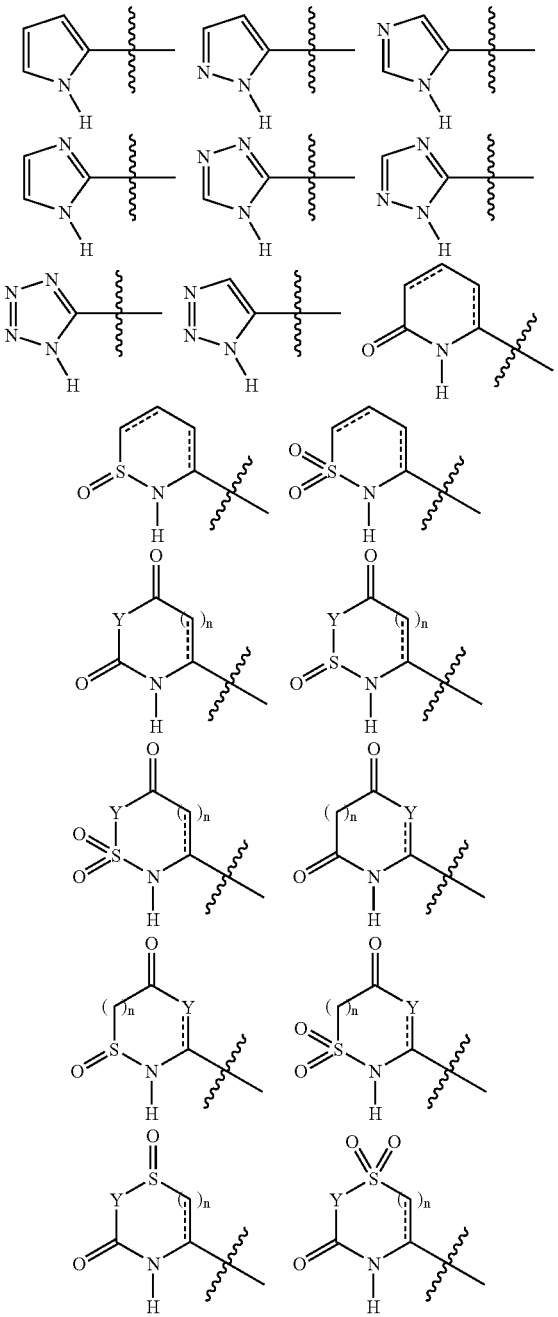

-continued

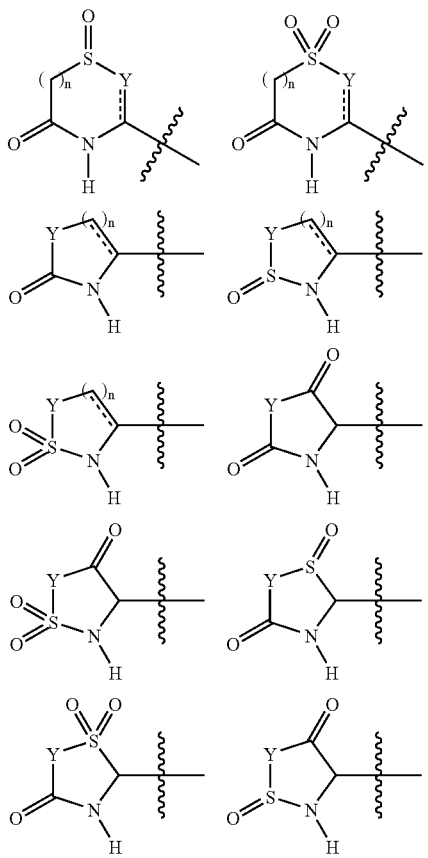

wherein:

T is optionally substituted with up to 3 J substituents, wherein J is as defined in claim 1;

Y is independently O, S, $NR_{10}$, or $C(R_{10})_2$;

n is independently 1 or 2; and

----- is independently a single bond or a double bond.

In another preferred embodiment, T is:

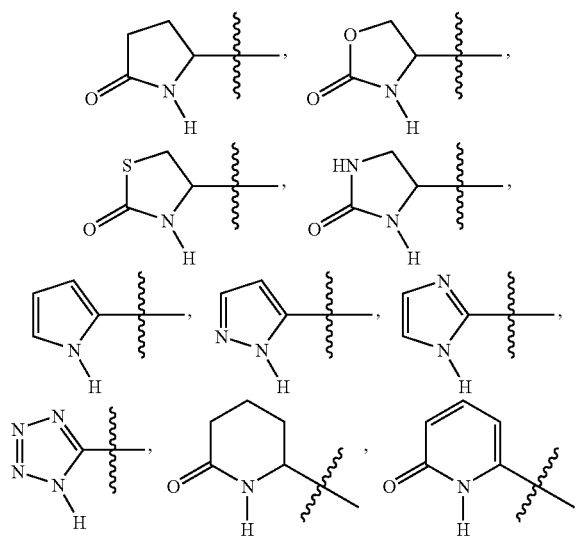

-continued

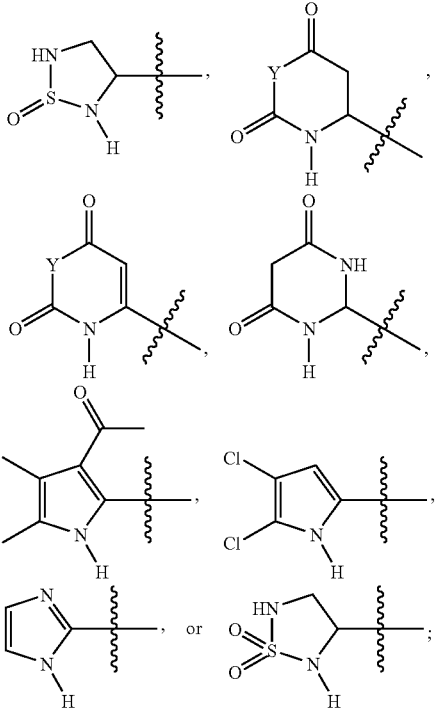

wherein Y is as defined above.

More Preferably T is

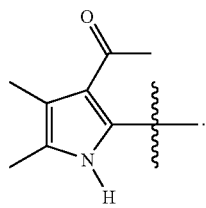 [SMILES: *c1[nH]c(C)c(C)c1C(C)=O]

According to yet another preferred embodiment, T is:

(C6-C10)-aryl, (C6-C10)-aryl-(C1-C12)aliphatic, (C3-C10)-cycloalkyl or -cycloalkenyl,

[(C3-C10)-cycloalkyl or -cycloalkenyl]-(C1-C12)-aliphatic, (C3-C10)-heterocyclyl, (C3-C10)-heterocyclyl-(C1-C12)-aliphatic, (C5-C10)heteroaryl, or (C5-C10)heteroaryl-(C1-C12)-aliphatic, wherein each T is optionally substituted with up to 3 J substituents.

According to yet another preferred embodiment of this invention, T:

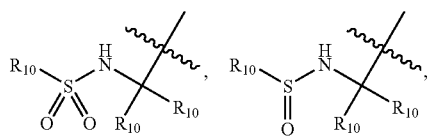

More preferably, T is:

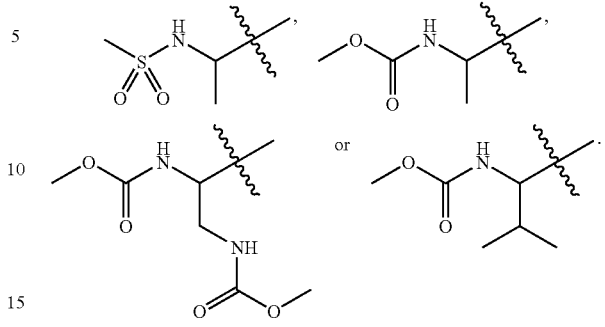

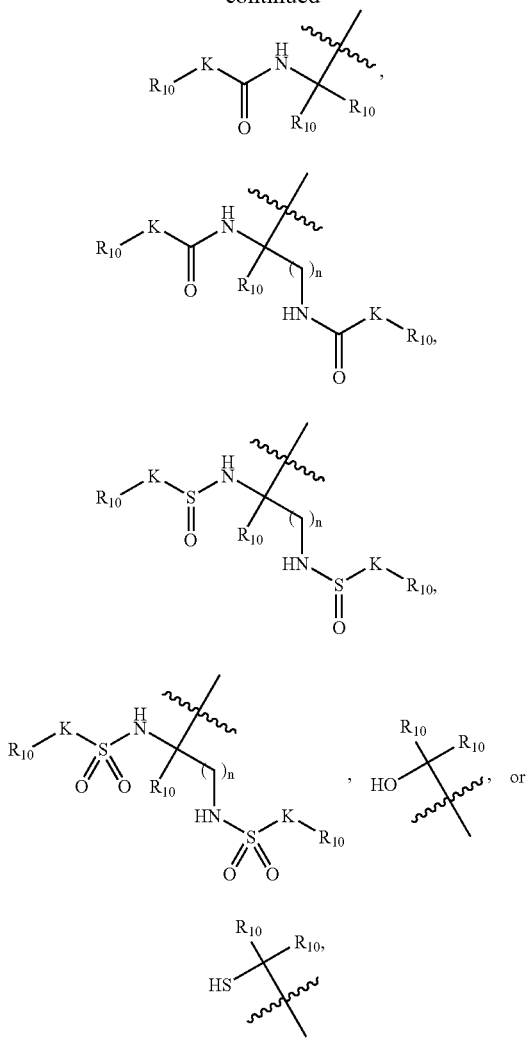

wherein:

R$_{10}$ is:

hydrogen, (C1-C12)-aliphatic, (C6-C10)-aryl, (C6-C10)-aryl-(C1-C12)aliphatic, (C3-C10)-cycloalkyl or -cycloalkenyl, [(C3-C10)-cycloalkyl or -cycloalkenyl]-(C1-C12)-aliphatic, (C3-C10)-heterocyclyl, (C3-C10)-heterocyclyl-(C1-C12)-aliphatic, (C5-C10)heteroaryl, or (C5-C10)heteroaryl-(C1-C12)-aliphatic, wherein each T is optionally substituted with up to 3 J substituents;

K is a bond, —O—, —S—, —NR$_9$—, —C(O)—, or —C(O)—NR$_9$—, wherein R$_9$ is hydrogen or C1-C12 aliphatic; and n is 1-3.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

More preferably, the compounds of this invention have the structure and stereochemistry depicted below in generalized formula (V):

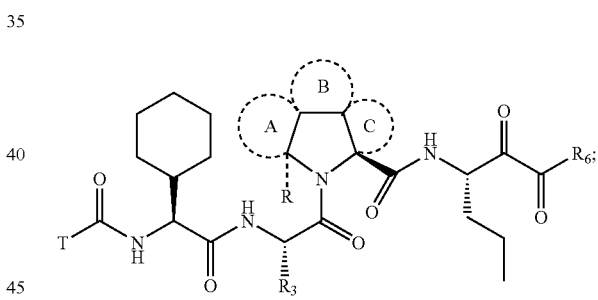

wherein T, R, R$_3$ and R$_6$ represent the embodiments set forth above and rings A, B, and C, if present, represent the embodiments set forth for compounds of formulas (I), (II), (III), and (IV).

Any of the preferred embodiments recited above may be combined to produce a preferred embodiment of this invention.

The compounds of this invention may be synthesized by standard chemical schemes well-known in the art. Schemes 1-22 below illustrate synthetic routes to the compounds of the present invention. Other equivalent schemes, which will be readily apparent to the ordinary skilled organic chemist, may alternatively be used to synthesize various portions of the molecule. A more specific synthetic scheme for compound 1A within applicants' invention is set forth in the examples.

Preparation of Compounds of Formula (I):
Scheme 1
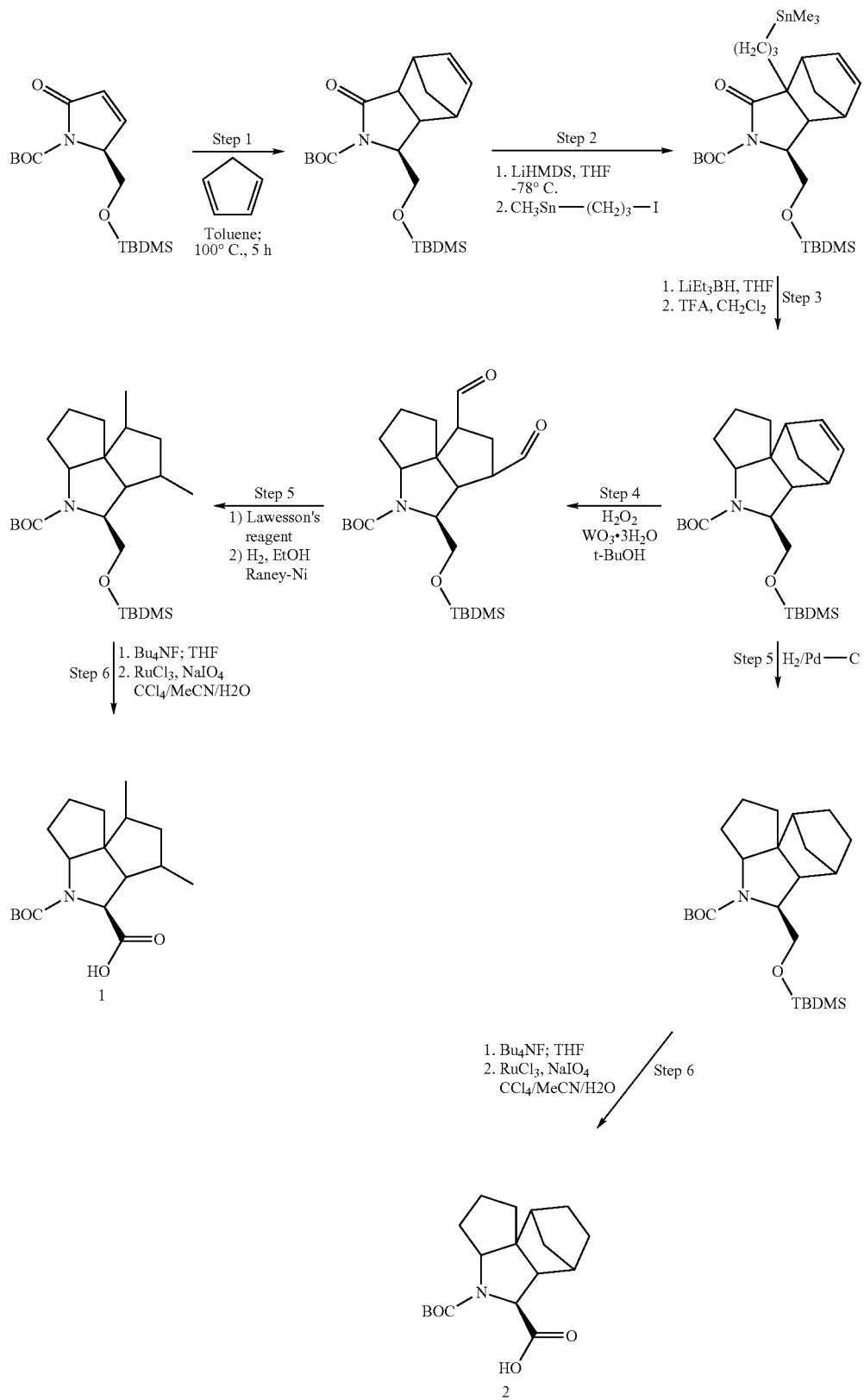

Preparation of Compounds of Formula (I):
Scheme 2
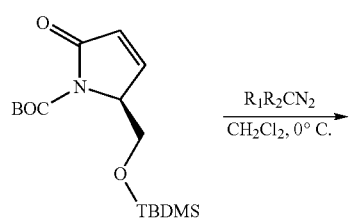
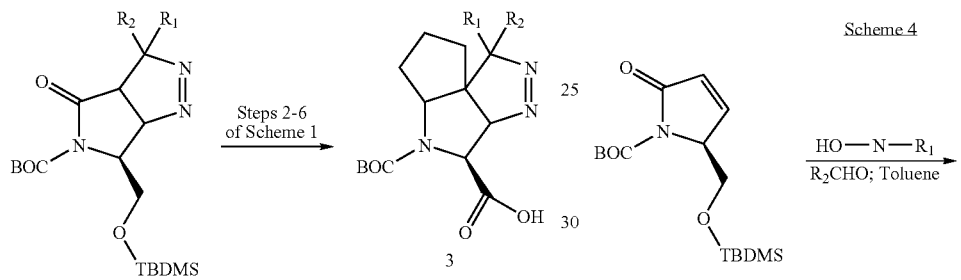
Scheme 3
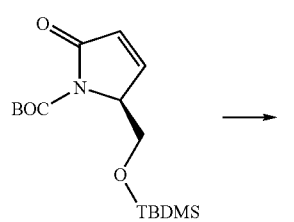
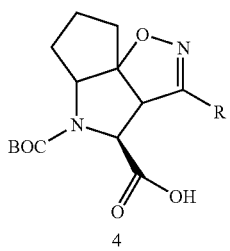
4
Preparation of Compounds of Formula (I):
Scheme 4
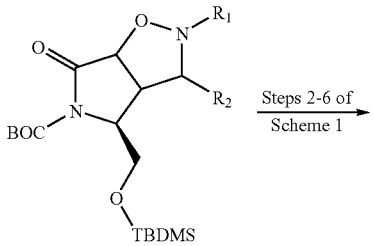
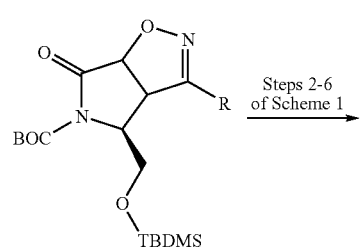
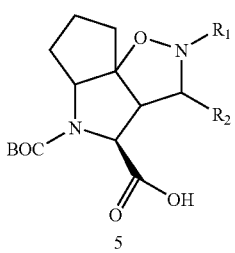
5

Scheme 5
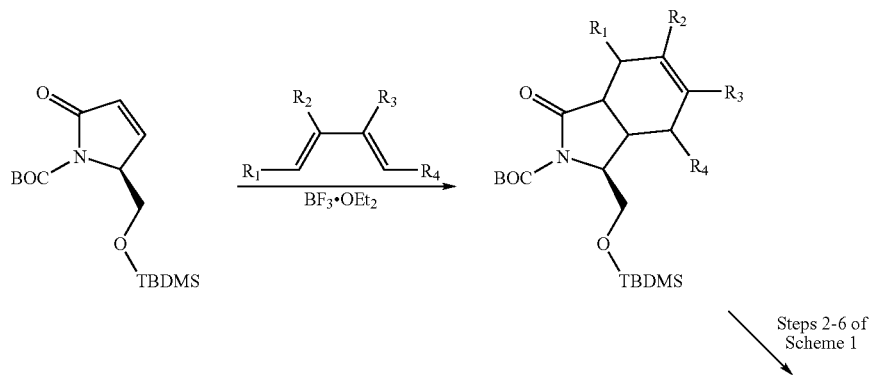
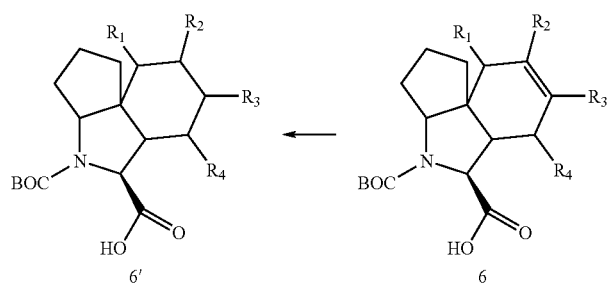
Preparation of Compounds of Formula (I):
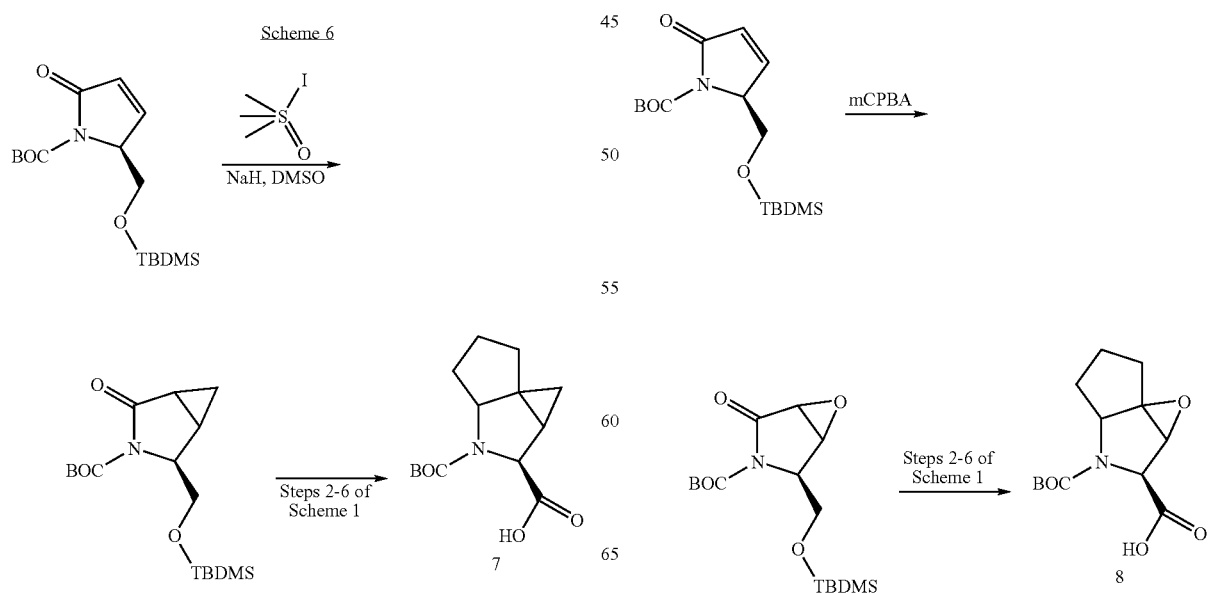

Preparation of Compounds of Formula (II):
Scheme 8
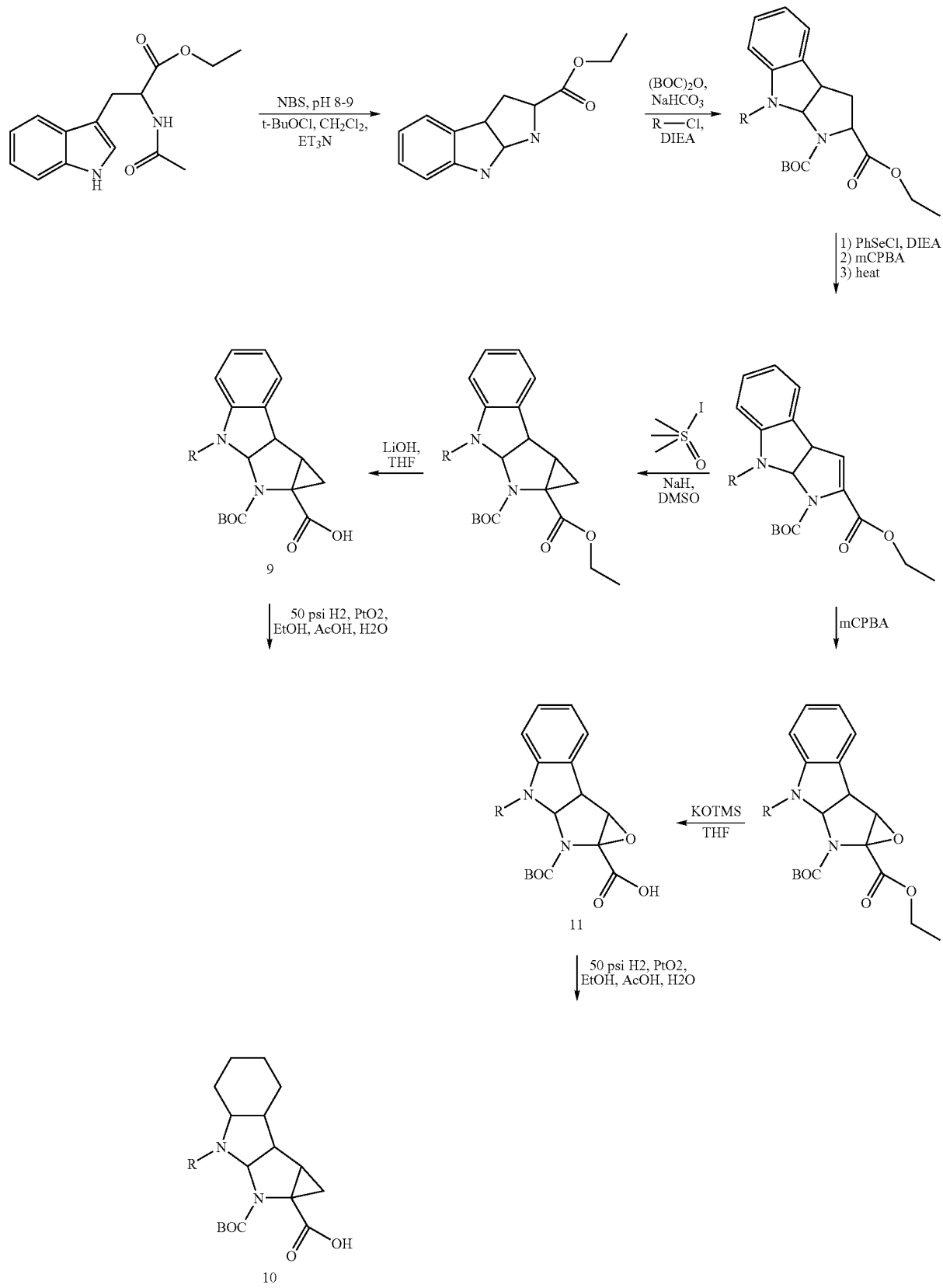

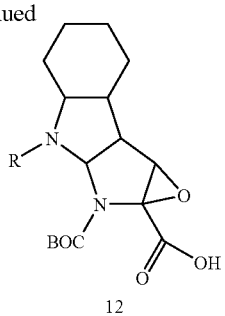
12
Preparation of Compounds of Formula (IV):
Scheme 9
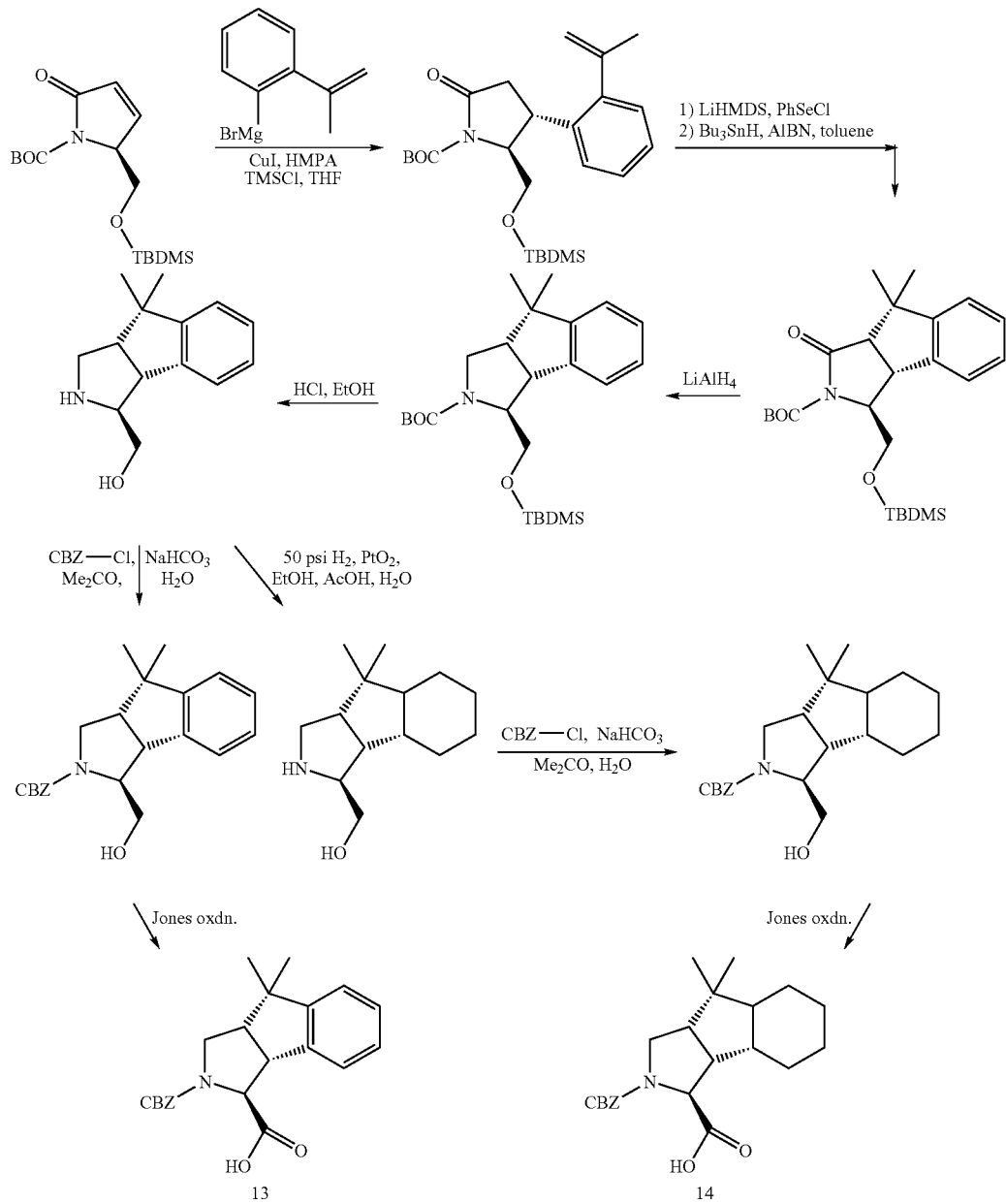
13
14

Preparation of Compounds of Formula (IV):
Scheme 10
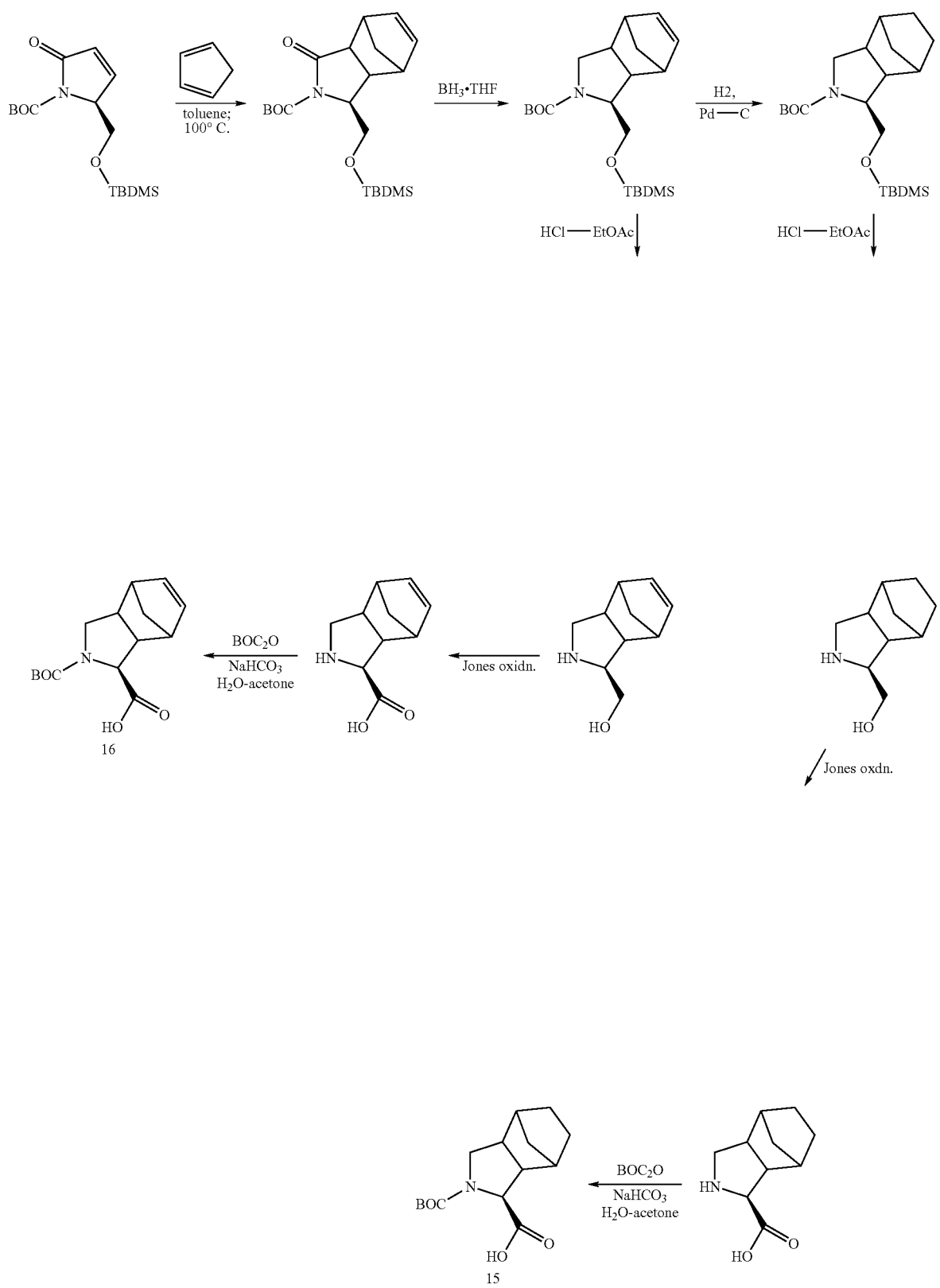

Scheme 11
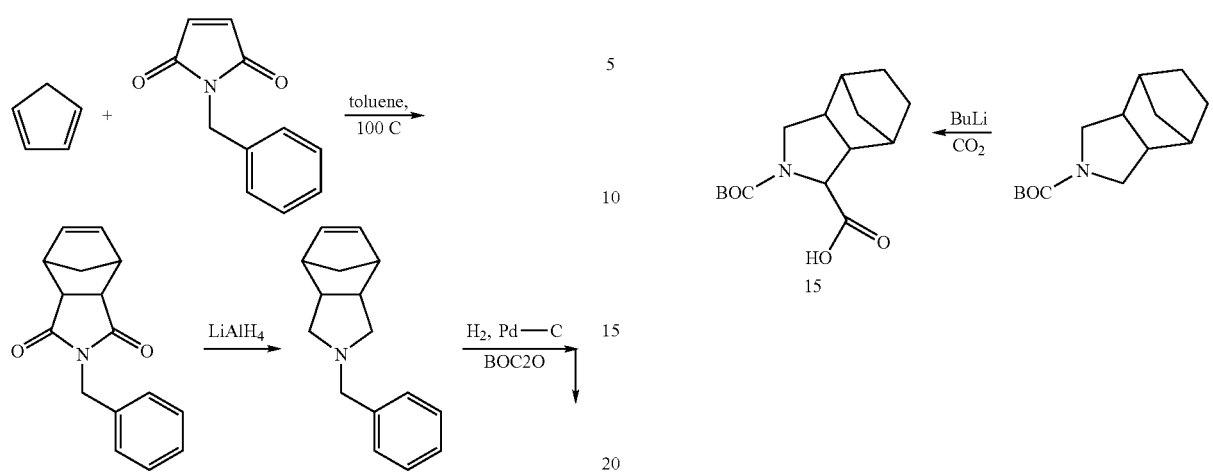
Preparation of Compounds of Formula (IV):
Scheme 12
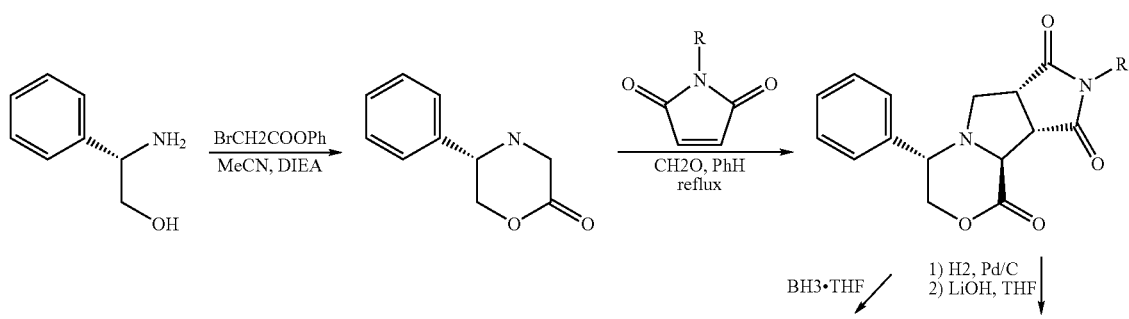
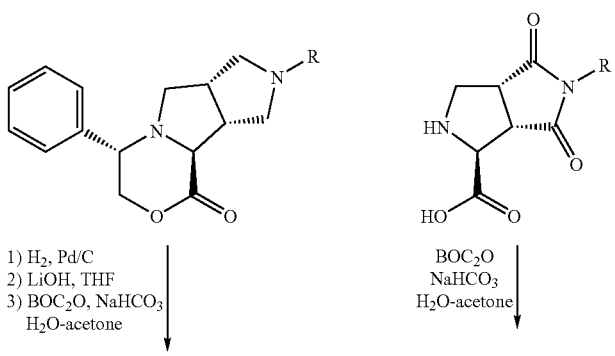
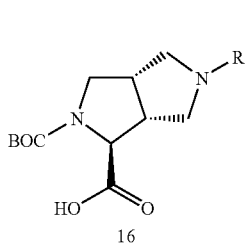
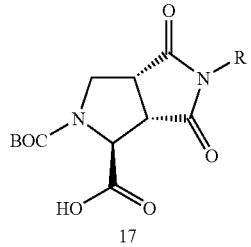

Preparation of Compounds of Formula (IV):
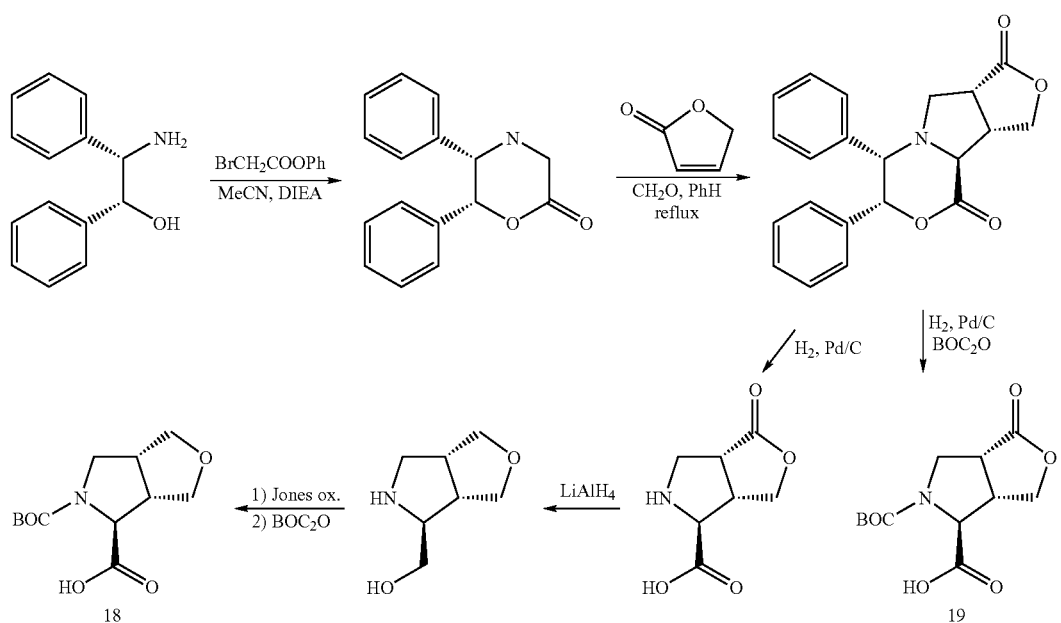
Preparation of Compounds of Formula (IV):
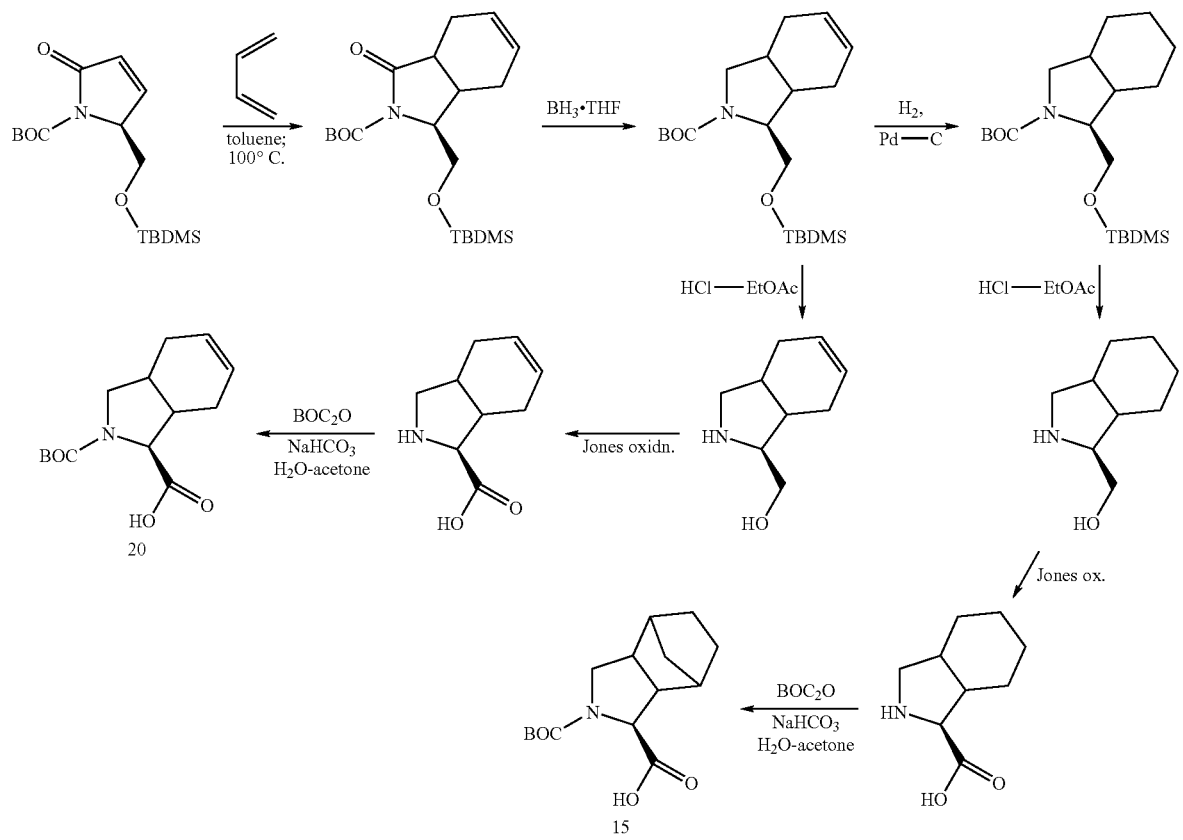

Preparation of compounds of Formula (IV):
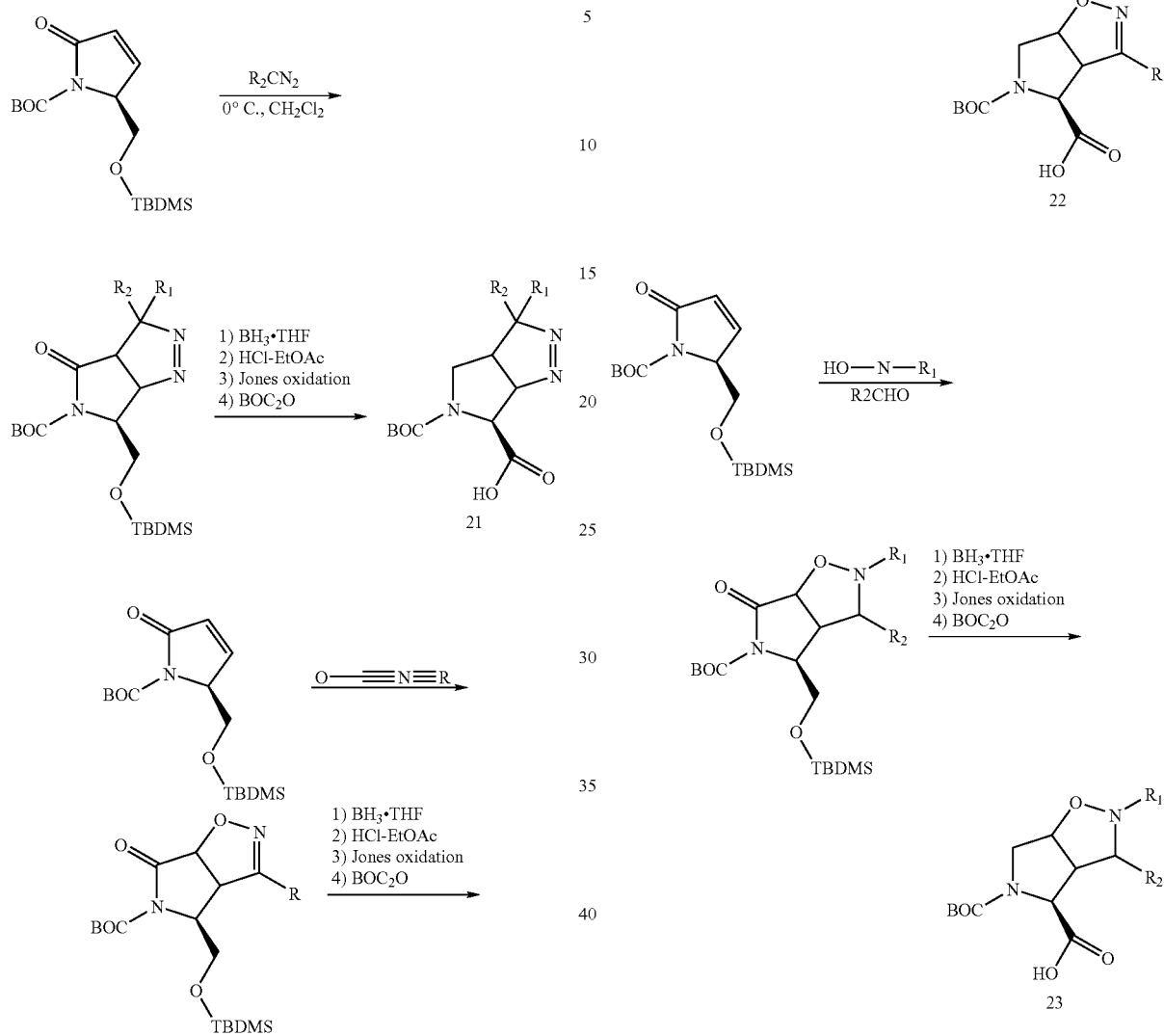
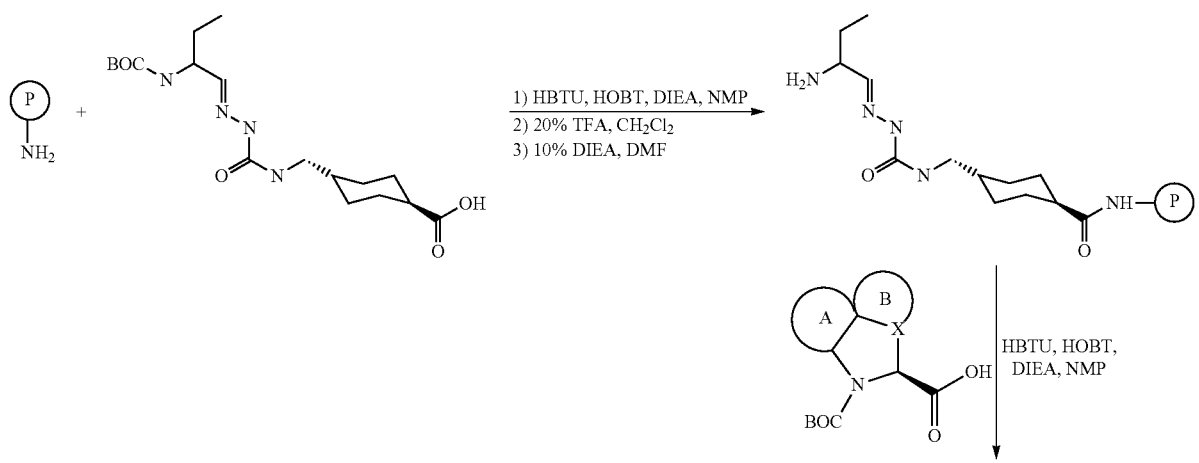

-continued
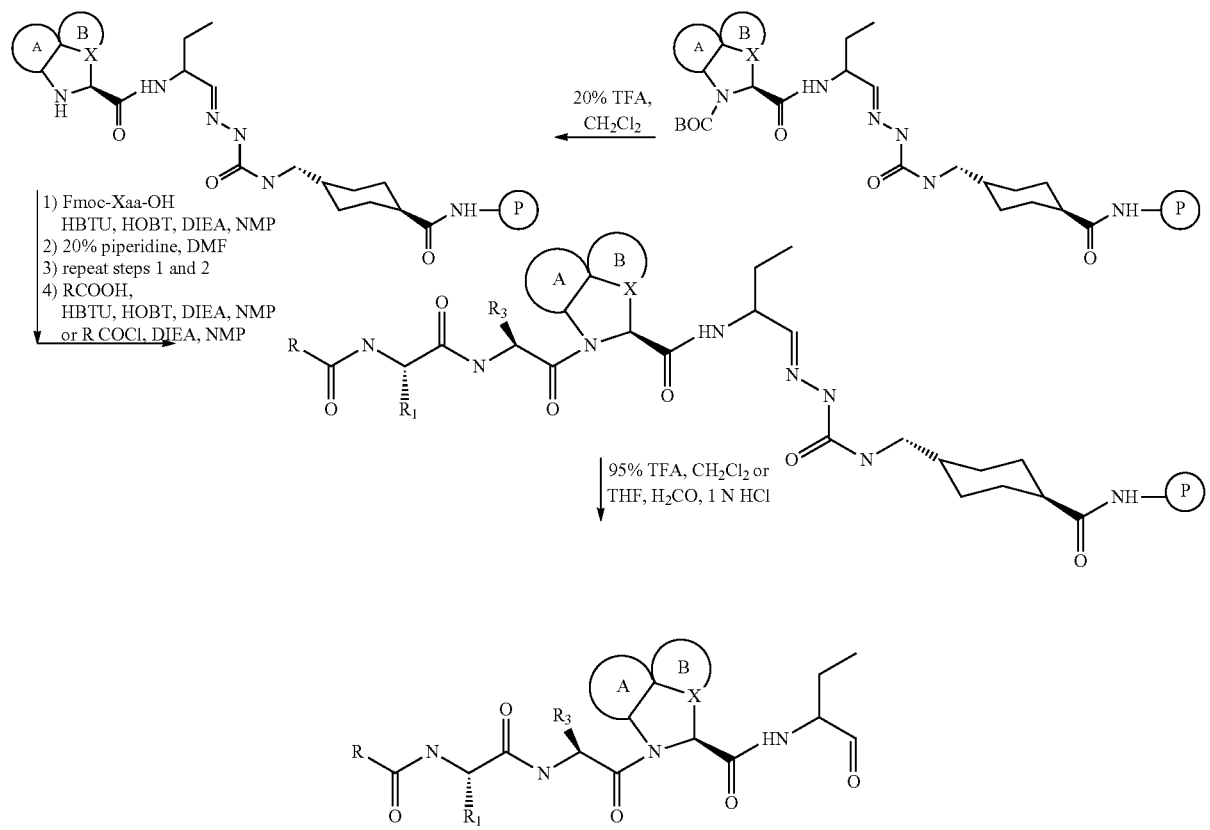
Scheme 17
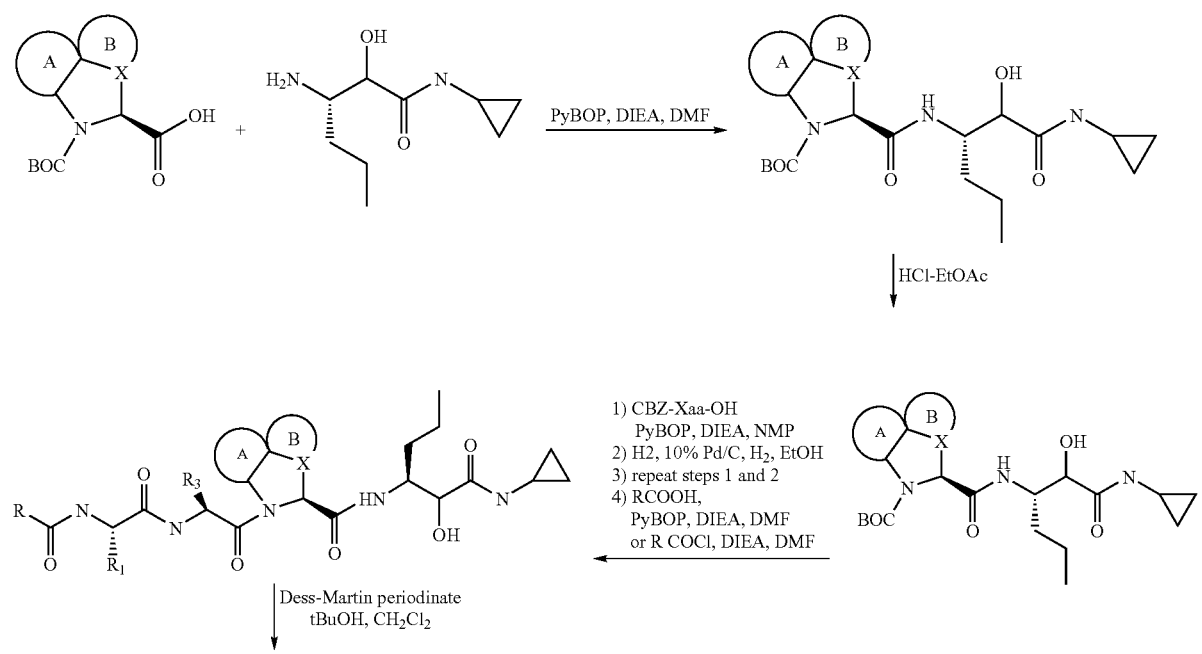

-continued
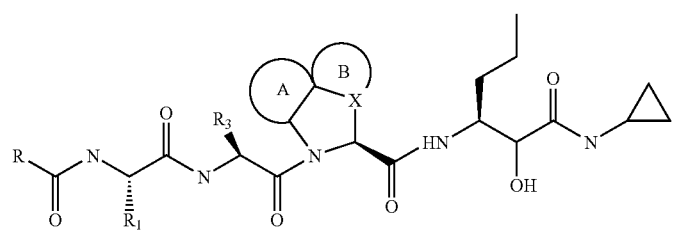
Scheme 18
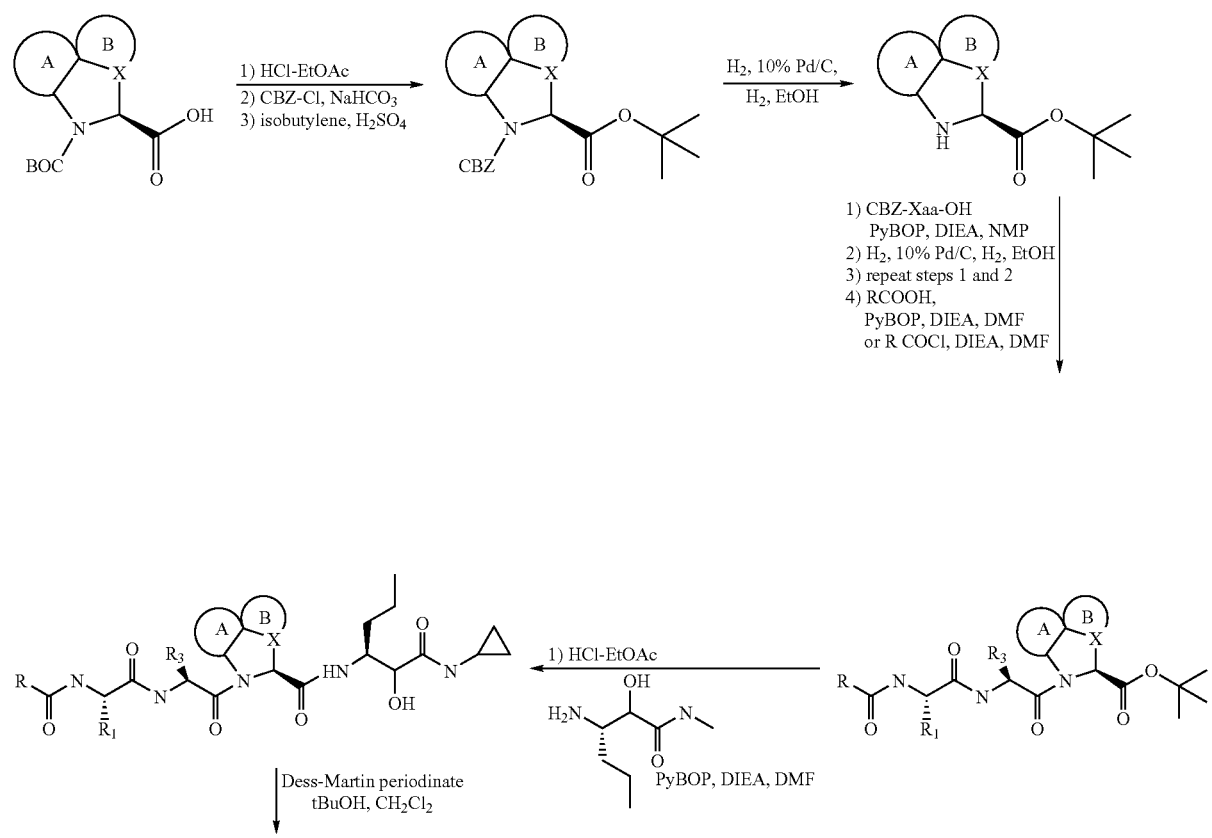
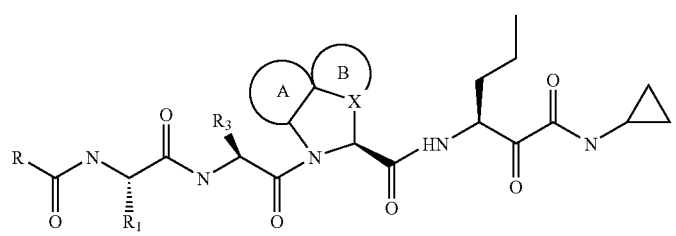
I-2

Preparation of Compounds of Formula (IV):
Scheme 19
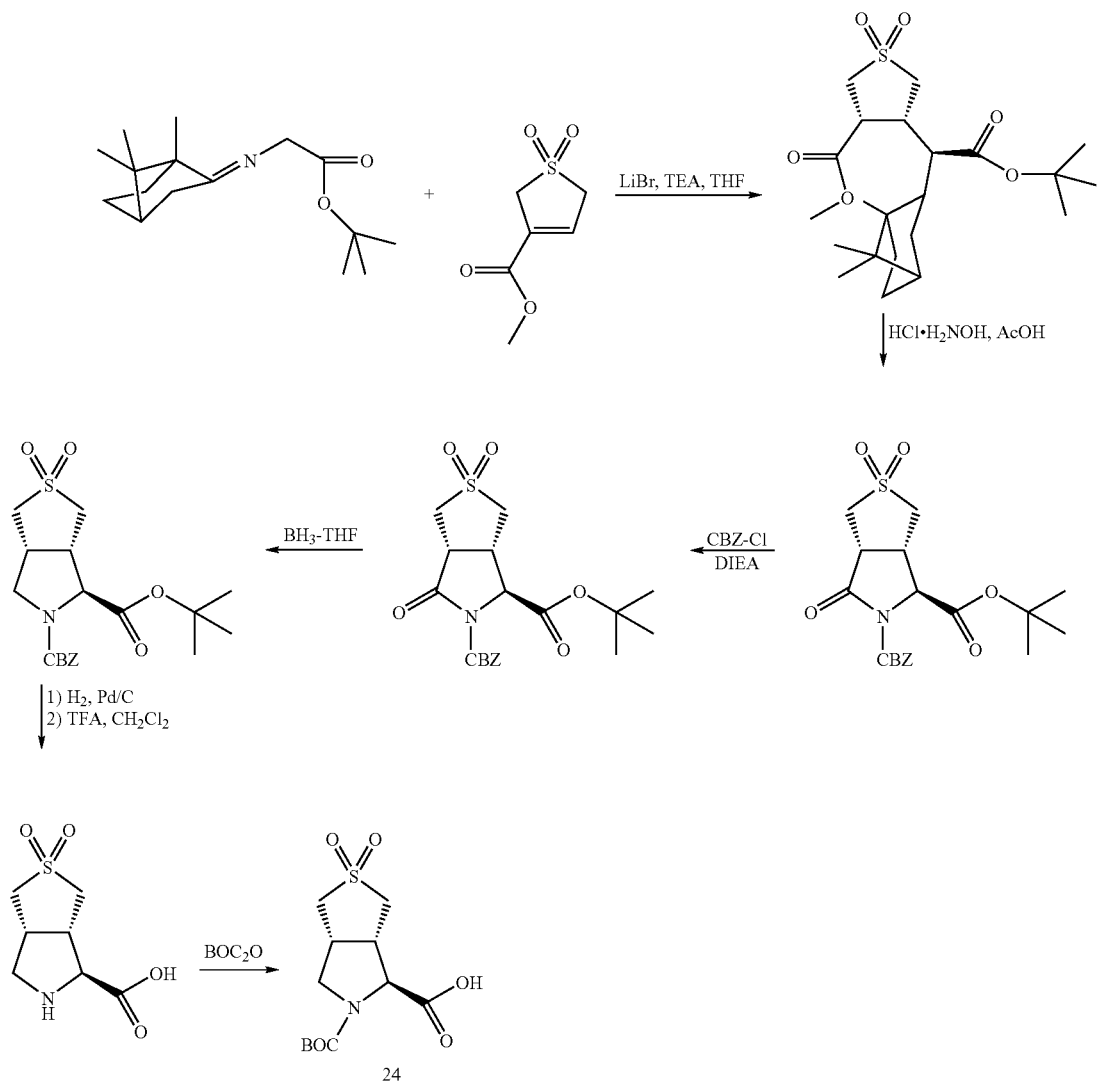
Preparation of Compounds of Formula (IV):
Scheme 20
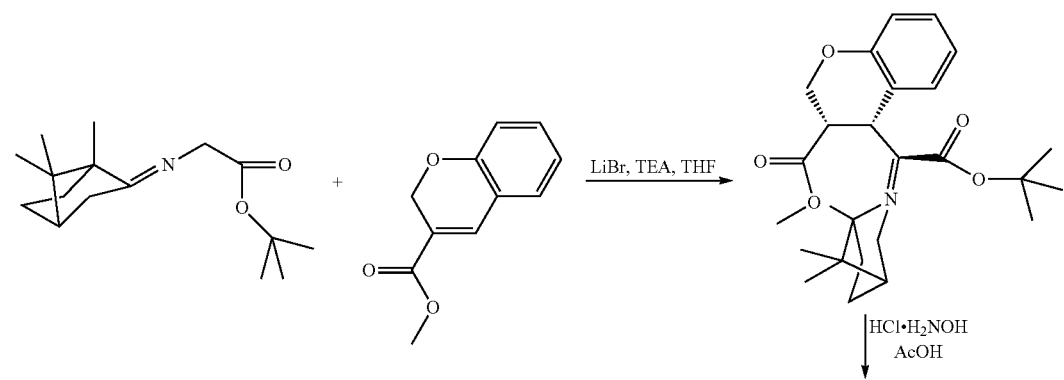

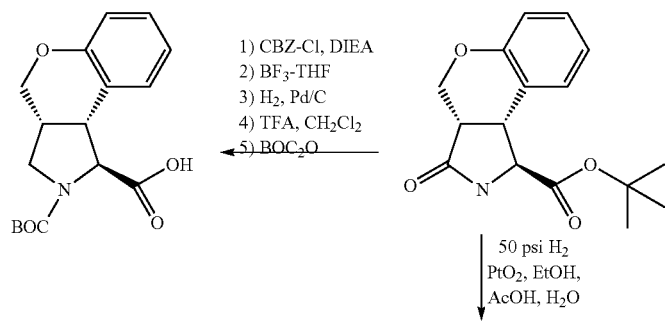
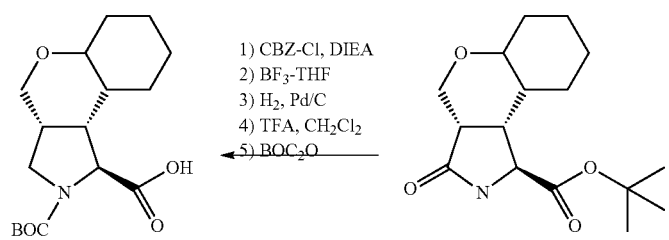
Preparation of Compounds of Formula (III):
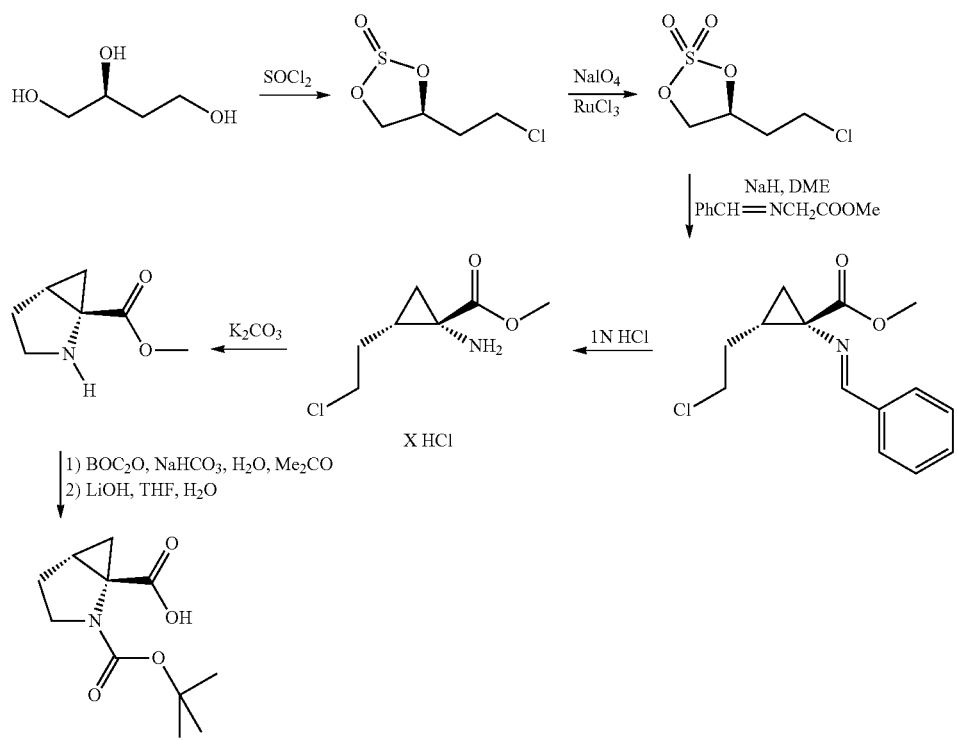
Scheme 21

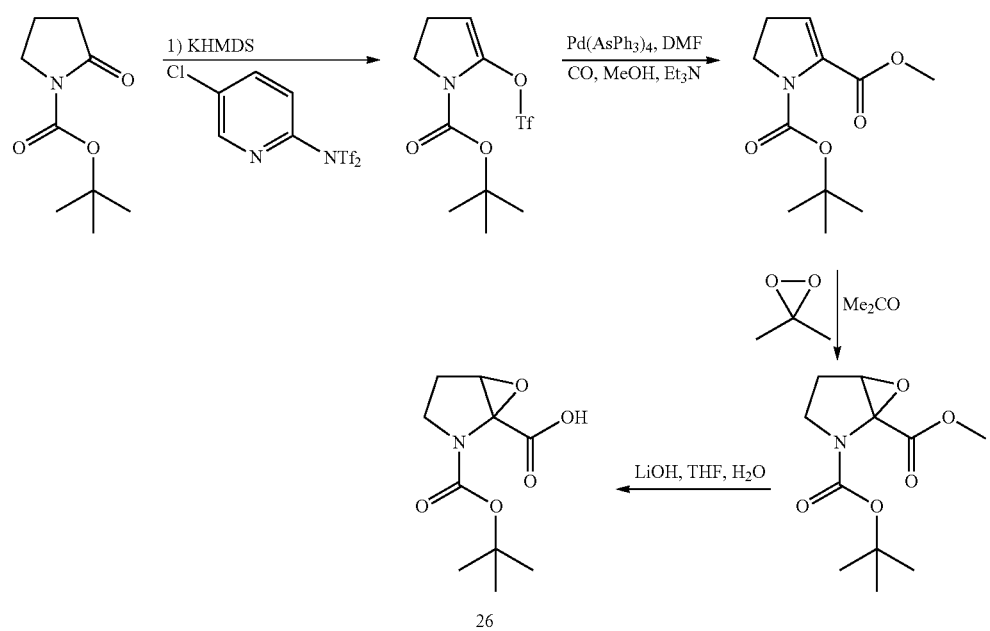
Scheme 22
Preparation of Compound 1A:
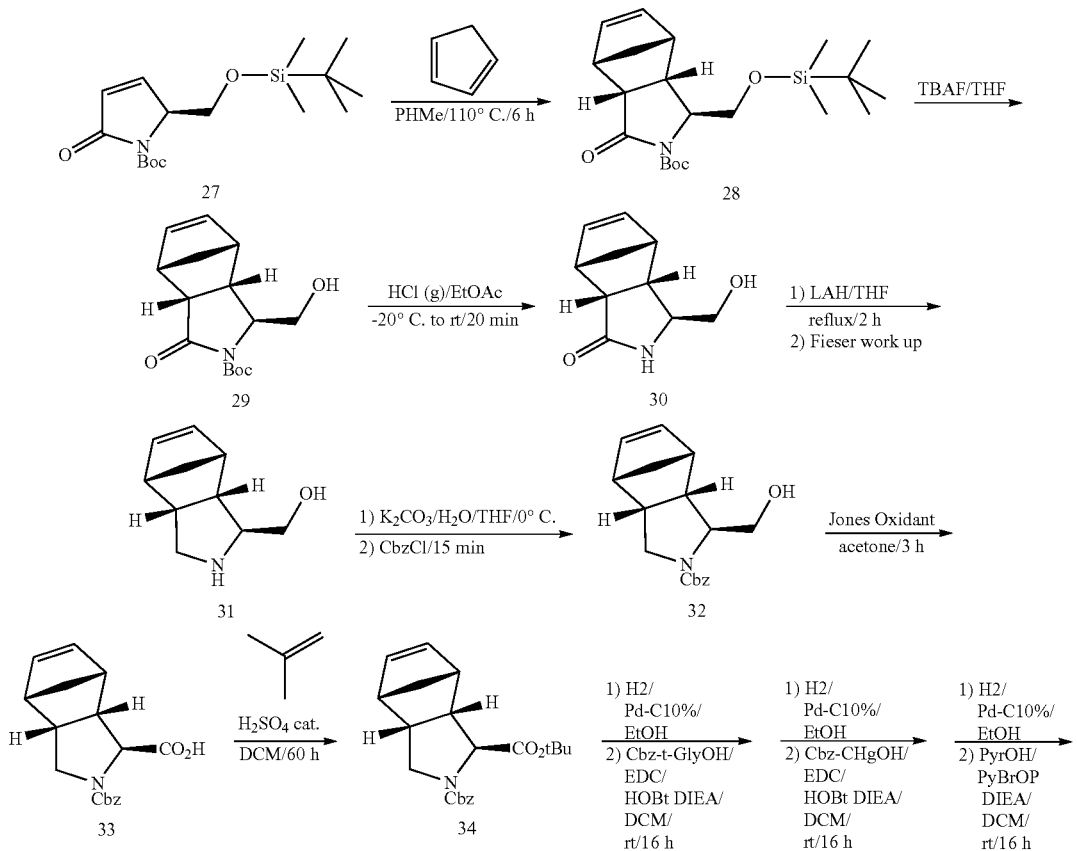

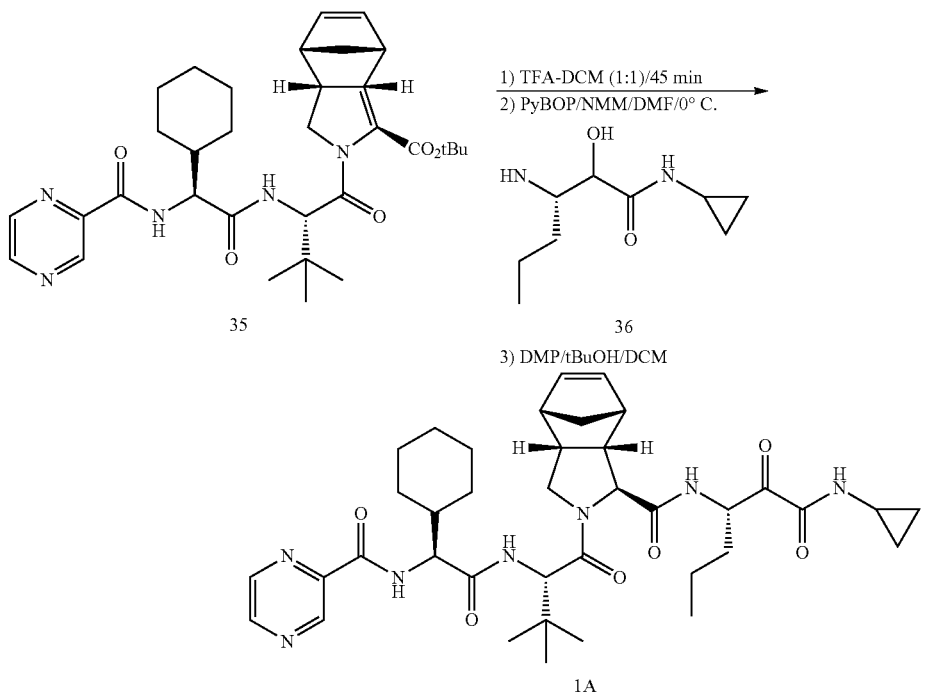

Compounds 1 to 26 and compound 1A in Schemes 1-15, 19-22 illustrate the multicyclic core of the peptidomimetic compounds of the present invention. These cores are readily converted into the compounds of the present invention by methods well known in the art.

For example, compounds 1 to 8 in Schemes 1-7 illustrate the core in compounds of formula (I). Compound 1, e.g., can be converted into a compound of formula (I) using the methods of, e.g., Schemes 16-18.

Compounds 9-12 in Scheme 8 illustrate the cores in compounds of formula (II). Compounds 9 to 12 can be readily converted into compounds of formula (II) using the methods of, e.g., Schemes 16-18.

Compounds 13 and 14 in Scheme 9 illustrate the cores in compounds of formula (IV). Compounds 13 and 14 can be readily converted into compounds of formula (IV) using the methods of, e.g., Schemes 16-18.

Compound 26 in Scheme 21 illustrates the core in compounds of formula (III). Compound 26 can be readily converted into a compound of formula (III) using the methods of, e.g., Schemes 16-18.

One of skill in the art will readily appreciate that the methods of Schemes 1-22 can be readily applied to any other ring or ring system within the scope of the present invention. Thus, Schemes 1-22 provide a facile synthetic route to the compounds of the present invention.

As set forth above, the compounds of this invention are capable of inhibiting the activity of HCV NS3-NS4A protease. In order to quantitate the activity of the compounds of this invention, cells containing HCV replicon were incubated with the compounds of this invention, and a Taqman Real Time PCR assay was conducted to determine the percentage inhibition of HCV RNA level and the $IC_{50}$ were calculated therefrom. The results are shown below in Table 1:

TABLE 1

| Cmpd. No. | Structure | Ki (nM) | $IC_{50}$ (nM) |
|---|---|---|---|
| IA | 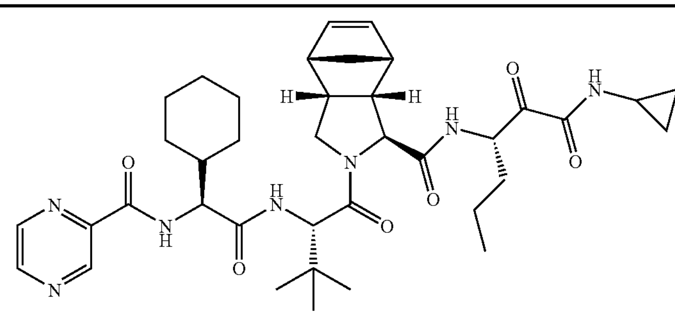 | 39 | 202 |

Another embodiment of this invention provides a composition comprising a compound of formula (I), formula (II), formula (III), or formula (IV) or a pharmaceutically acceptable salt thereof in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I, II, III or IV, and one or more additional therapeutic or prophylactic agents, both the compound and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferred are pharmaceutical compositions formulated for oral administration.

In a related embodiment, the compositions of this invention additionally comprise another anti-viral agent, preferably an anti-HCV agent. Such anti-viral agents include, but are not limited to, immunomodulatory agents, such as $\alpha$-, $\beta$-, and $\gamma$-interferons and pegylated derivatized interferon-$\alpha$ compounds; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. More preferably, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as $\alpha$-, $\beta$-, and $\gamma$-interferons and pegylated derivatized interferon-$\alpha$ compounds; other anti-viral agents, such as ribavirin and amantadine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. No. 5,807,876, mycophenolic acid and derivatives thereof); or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments; laboratory instruments and garments; blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In order that this invention be more fully understood, the following examples are set forth. These examples are for the purpose of illustration only and are not to be construed as limiting the scope of the invention in any way.

EXAMPLE 1

3-(tert-Butyl-dimethyl-silanyloxymethyl)-5-oxo-4-aza-tricyclo[5.2.1.0$^{2,6}$]dec-8-ene-4-carboxylic acid tert-butyl ester (28)

2-(tert-Butyl-dimethyl-silanyloxymethyl)-5-oxo-2,5-dihydro-pyrrole-1-carboxylic acid tert-butyl ester (27) (4 g; 12.2 mmol) and freshly distilled cyclopentadiene (8 mL; 12 eq.) were heated in a sealed tube in toluene for 6 h at 110° C. Concentration and purification by flash chromatography (10% EtOAc/90% hexanes) afforded 3.23 g (67%) of the desired product 28. $^1$H NMR (CDCl$_3$) □ 6.1 (bs, 1H), 6.0 (bs, 1H), 3.8 (dd, 1H), 3.6 (d, 1H), 3.5 (s, 1H), 3.3 (s, 1H), 3.1 (dd, 1H), 2.9 (s, 1H), 2.6 (bs, 1H), 1.6 (d, 2H), 1.5 (s, 9H), 1.3 (d, 1H), 0.9 (s, 9H), 0.15 (s, 3H), 0.1 (s, 3H) ppm.

EXAMPLE 2

3-Hydroxymethyl-5-oxo-4-aza-tricyclo[5.2.1.0$^{2,6}$]dec-8-ene-4-carboxylic acid tert-butyl ester (29)

A solution of 28 (3.2 g; 8.1 mmol) in 60 mL of THF and acetic acid (1.16 mL; 20.3 mmol) was treated with TBAF 1M in THF. The reaction mixture was stirred for 16 h then was diluted with CH$_2$Cl$_2$ (120 mL) and washed with water (75 mL). The organic layer was dried with sodium sulfate and concentrated in vacuo to a yellow oil. Flash chromatography (60% EtOAc/40% hexanes) afforded 1.81 g (81%) of the desired product 29. $^1$H NMR (CDCl$_3$) δ 6.2 (bs, 1H), 6.1 (bs, 1H), 3.8 (d, 1H), 3.6 (m, 2H), 3.3 (s, 1H), 3.15 (dd, 1H), 3.1 (s, 1H), 2.5 (dd, 1H), 1.5 (app.t, 3H), 1.35 (s, 9H) ppm.

EXAMPLE 3

3-Hydroxymethyl-4-aza-tricycloc-4-carboxylic acid benzyl ester (32)

To a solution of 29 (1.81 g, 6.5 mmol) in 50 mL of dry ethyl acetate at 0° C. was bubbled dry HCl gas for 5 minutes. Stirring was continued while warming up to room temperature over a period of 10 minutes. Concentration to dryness afforded a solid residue that was subjected to lithium aluminium hydride reduction (2.5 equivalents) in refluxing THF for 2 h. Fieser work up afforded 1.07 g of the reduced product 31 that was used directly for the next step. A solution of 31 (1.07 g, 6.5 mmol) in 10 mL of dry THF was added to a vigorously stirred solution of potassium carbonate in 4 mL of water at −2° C. to 0° C. Cbz-Cl was added dropwise maintaining the temperature around 0° C. After the addition was completed (10 minutes), the reaction was further stirred for an additional 15 minutes at 0° C. and poured onto crushed ice and water (14 mL). Sodium chloride was added to saturate the aqueous phase. The organic phase was separated and the aqueous further extracted (3×50 mL) with ethyl acetate. The combined organic phase was washed with 5% aqueous HCl, water and brine, dried (Na$_2$SO$_4$) and concentrated in vacuo to give, after flash chromatography (50% EtOAc/50% hexanes) 960 mg (50%) of desired product 32. $^1$H NMR (CDCl$_3$) δ 7.3 (m, 5H), 6.2 (M, 2H), 5.1 (m, 2H), 3.8 (m, 2H), 3.4 (m, 2H), 3.0 (m, 3H), 2.5 (m, 2H), 1.3 (m, 2H) ppm.

EXAMPLE 4

4-Aza-tricyclo[5.2.1.0$^{2,6}$]dec-8-ene-3,4-dicarboxylic acid 4-benzyl ester 3-tert-butyl ester (34)

Compound 32 (410 mg, 1.37 mmol) was dissolved in 5 mL of acetone and added dropwise to a stirred solution of Jones reagent (1.1 mL) in 1 mL of acetone at 0° C. The reaction mixture was stirred at 5° C. for 3 h and was concentrated in vacuo to a dark residue. Residue was re-dissolved in ethyl acetate (50 mL) and washed (5×10 mL). The organic phase dried (Na$_2$SO$_4$) and concentrated in vacuo to give 400 mg (93%) of compound 33 that was used directly for the next step. To a solution of 33 (400 mg, 1.28 mmol) in 10 mL of CH$_2$Cl$_2$ containing a catalytic amount of concentrated sulfuric acid at −20° C. was condensed 2 mL of isobutylene. The tube was sealed and stirred at room temperature for 60 h. The excess isobutylene was released and the CH$_2$Cl$_2$ removed in vacuo to a residue that was subjected to after flash chromatography (20% EtOAc/80% hexanes) which gave 378 mg (80%) of the desired ester 34. $^1$H NMR (CDCl$_3$) δ 7.3 (m, 5H), 6.2 (m, 2H), 5.0 (m, 2H), 3.8 (m, 1H), 3.5 (m, 1H), 3.2 (m, 1H), 3.1 (m, 1H), 2.8 (m, 3H), 1.5 (m, 2H), 1.2 (m, 9H) ppm.

EXAMPLE 5

4-(2-{2-Cyclohexyl-2-[(pyrazine-2-carbonyl)-amino]-acetylamino}-3,3-dimethyl-butyryl)-4-aza-tricyclo[5.2.1.0$^{2,6}$]dec-8-ene-3-carboxylic acid tert-butyl ester (35)

Removal of the Cbz group of 34 (378 mg, 1.02 mmol) with hydrogenation under 1 atm of hydrogen using Pd—C10% in ethanol gave, after 5 h, the desired aminoester intermediate in quantitative yield.

The crude compound was coupled to tert-butylglycine shown in the next step. To a solution of Cbz-tert-butyl glycine (271 mg, 1.02 mmol) in 2 mL of CH$_2$Cl$_2$ at 0° C. was added EDC (235 mg, 1.23 mmol), HOBt (203 mg, 1.33 mmol) and DIEA (0.534 mL, 3.07 mmol). The resulting mixture was stirred at 0° C. for 15 min. after which, the above amino ester was slowly added in 2 mL of CH$_2$Cl$_2$. The resulting reaction mixture was stirred at room temp. for 16 h. Concentration gave a residue that was re-dissolved in EtOAc. Successive washes with 0.5N HCL, saturated aqueous NaHCO$_3$ and brine gave after drying (Na$_2$SO$_4$) and concentration in vacuo the desired product. Flash chromatography (20% EtOAc/80% hexanes) provided 480 mg (100%) of pure dipeptide. The Cbz group of the dipeptide was removed as described above and the resulting aminoester dipeptide was coupled to Cbz-cyclohexyl glycine shown in the next step.

To a solution of Cbz-cyclohexyl glycine (289 mg, 1 mmol) in 2 mL of CH$_2$Cl$_2$ at 0° C. was added EDC (228 mg, 1.19 mmol), HOBt (190 mg, 1.29 mmol) and DIEA (0.517 mL, 2.97 mmol). The resulting mixture was stirred at 0° C. for 15 min. after which, the above amino ester was slowly added in 2 mL of CH$_2$Cl$_2$. The resulting reaction mixture was stirred at room temp. for 16 h. Concentration gave a residue that was re-dissolved in EtOAc. Successive washes with 0.5N HCL, satd' aqueous NaHCO$_3$ and brine gave after drying (Na$_2$SO$_4$) and concentration in vacuo the desired product which was subjected to flash chromatography (20% EtOAc/80% hexanes) to provide 556 mg (90%) of pure tripeptide. The Cbz group of the tripeptide was removed as described above and the resulting aminoester tripeptide was coupled to 1,4-pyrazine carboxylic acid shown in the next step.

To a solution of 1,4-pyrazine carboxylic acid (110 mg, 0.891 mmol) in 2 mL of $CH_2Cl_2$ was added PyBrOP (457 mg, 0.98 mmol and DIEA (0.465 mL, 2.67 mmol). The resulting mixture was stirred at room temp. for 15 min. after which, the above amino ester was slowly added in 2 mL of $CH_2Cl_2$. The resulting reaction mixture was stirred at room temp. for 16 h. Concentration gave a residue that was re-dissolved in EtOAc. Successive washes with 0.5N HCL, satd' aqueous $NaHCO_3$ and brine gave after drying ($Na_2SO_4$) and concentration in vacuo the desired product which was subjected to flash chromatography (50% EtOAc/50% hexanes) to provide 410 mg (79%) of pure capped tripeptide 35. $^1H$ NMR ($CDCl_3$) δ 9.3 (s, 1H), 8.8 (s, 1H), 8.5 (s, 1H), 8.3 (d, 1H), 6.7 (d, 1H), 4.9 (d, 1H), 4.7 (s, 1H), 4.5 (tr, 1H), 3.95 (d, 1H), 3.6 (app. dd, 1H), 2.6 (m, 2H), 2.3 (d, 2H), 1.75 (m, 5H), 1.5 to 0.9 (m, 12H), 1.4 (s, 9H), 1.0 (s, 9H) ppm.

EXAMPLE 6

4-(2-{2-Cyclohexyl-2-[(pyrazine-2-carbonyl)-amino]-acetylamino}-3,3-dimethyl-butyryl)-4-aza-tricyclo[5.2.-1.0$^{2,6}$]dec-8-ene-3-carboxylic acid (1-cyclproylaminooxalyl-butyl)-amide (1A)

The t-butyl ester group of the capped tripeptide 35 (410 mg, 0.688 mmol) was cleaved with a 1:1 mixture of TFA-$CH_2Cl_2$ at room temp. for 45 minutes and concentrated in vacuo. The resulting aminoester dipeptide was coupled to hydroxyamide 36 shown in the next step.

To a stirring solution of the capped tripeptide acid in 6 mL of dry DMF at 0C was added, PyBOP (376 mg, 0.722 mmol) followed by NMM (0.226 mL, 2.06 mmol). The reaction mixture was stirred for 1 h at room temp. after which a solution of 36 (168 mg, 0.758 mmol) and 0.226 mL of NMM was slowly added. The coupling reaction was stirred for 16 hours, diluted with ethyl acetate and was successively washed with; water (3×), citric acid 10%, water and brine. The organic layer was dried ($Na_2SO_4$) and concentrated in vacuo. Flash chromatography (2.5% MeOH/97.5% ethyl acetate) provided 362 mg of hydroxy amide tetrapeptide that was oxidized with Dess-Martin periodinane reagent (650 mg, 1.53 mmol) and t-butanol (0.65 mL) in 5 mL of $CH_2Cl_2$ at room temp. for 3 hours. The reaction mixture was quenched with sodium thiosulfate 1M solution (2 mL) and stirred until the two phases were clearly separated. The organic layer was diluted with 5 more mL of $CH_2Cl_2$ and washed (3×) with 10% potassium carbonate aqueous solution (5 mL), dried ($Na_2SO_4$) and concentrated in vacuo. Flash chromatography (2.5% MeOH/97.5% ethyl acetate) provided 270 mg of ketoamide tetrapeptide 1A. LCMS M+H=706.42, M−H=704.42. Retention Time (10-90% MeCN-$H_2O$ with 0.1% TFA over 6 minutes)=3.94 min.

EXAMPLE 7

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then diluted media A into a final concentration of 100,000 cells per ml with. 10,000 cells in 100 ul are plated into each well of a 96-well tissue culture plate, and culture overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

The media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C.

At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells were added to the PCR reactions for quantification of both HCV and BVDV RNA in the same PCR well. Experimental failure was flagged and rejected based on the level of BVDV RNA in each well. The level of HCV RNA in each well was calculated according to a standard curve that is run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

The IC50 values inhibitory activity of some of the compounds of the present invention is shown in Table 1 above.

EXAMPLE 8

The Ki determinations were performed as follows. The Ki values for some compounds of the present invention are recited above in Table 1.
HPLC Microbore Method for Separation of 5AB Substrate and Products Substrate $NH_2$-Glu-Asp-Val-Val-(alpha)Abu-Cys-Ser-Met-Ser-Tyr-COOH Stock solution of 20 mM 5AB was made in DMSO w/0.2M DTT. This was stored in aliquots at −20 C.

Buffer: 50 mM HEPES, pH 7.8; 20% glycerol; 100 mM NaCl Total assay volume was 200 µL

|  | X1 (µL) | Conc. in assay |
|---|---|---|
| Buffer | 155 | see above |
| 5 mM KK4A | 1 | 25 µM |
| 1 M DTT | 1 | 5 mM |
| DMSO or inhibitor | 3 | 1.5% v/v |
| 0.25 µM tNS3 | 20 | 25 nM |
| 200 µM 5AB (initiate) | 20 | 20 µM |

The buffer was combined with KK4A, DTT, and tNS3; 177 µL of this solution was distributed each into wells of 96 well plate and incubated at 30° C. for ~5-10 min. 3 µL of appropriate concentration of test compound dissolved in DMSO (DMSO only for control) was added to each well and incubate at 30° C. for 15 min.

Reaction was initiated by addition of 20 µL of 200 µM 5AB substrate (20 µM concentration is equivalent or slightly lower than the Km for 5AB) and incubated for 20 min at 30° C. The reaction was terminated by addition of 50 µL of 10% TFA 200 µL aliquots were transferred to HPLC vials The SMSY product was isolated from substrate and KK4A by the method which follows.

Microbore Separation Method
Instrumentation:
Hewlett Packard 1100
Degasser G1322A
Binary pump G1312A
Autosampler G1313A
Column themostated chamber G1316A
Diode array detector G1315A
Column: Phenomenex Jupiter; 5 micron C18; 300 angstroms; 150×2 mm; P/O 00F-4053-B0
Column thermostat: 40° C.
Injection volume: 100 µL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min

What is claimed is:
1. A compound of formula (I):

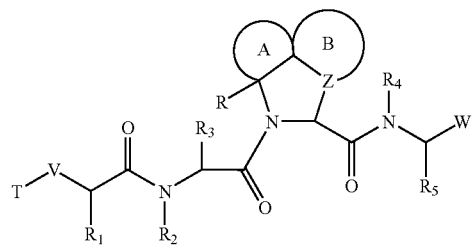

(I)

wherein:
ring A is a carbocyclic or heterocyclic ring, wherein ring A is optionally fused to a carbocyclic, heterocyclic or heteroaryl ring;
wherein ring A has up to 3 substituents selected independently from J;
ring B is a carbocyclic or heterocyclic ring, wherein ring B is optionally fused to a carbocyclic, heterocyclic or heteroaryl ring;
wherein ring B has up to 3 substituents selected independently from J;
J is halogen, —OR', —NO$_2$, —CF$_3$, —OCF$_3$, —R', oxo, —OR', —O-benzyl, —O-phenyl, 1,2-methylenedioxy, 1,2-ethylenedioxy, —N(R')$_2$, —SR', —SOR', —SO$_2$R', —C(O)R', —COOR' or —CON(R')$_2$, wherein R' is independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
R$_1$ and R$_3$ are independently:
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic,
wherein each of R$_1$ and R$_3$ is independently and optionally substituted with up to 3 substituents independently selected from J;
wherein up to 3 aliphatic carbon atoms in R$_1$ and R$_3$ may be replaced by a heteroatom selected from O, NH, S, SO, or SO$_2$ in a chemically stable arrangement;
R$_2$ and R$_4$ are independently
hydrogen,
(C1-C12)-aliphatic,
(C3-C10)-cycloalkyl-(C1-C12)-aliphatic, or
(C6-C10)aryl-(C1-C12)-aliphatic,
wherein each of R$_2$ and R$_4$ is independently and optionally substituted with up to 3 substituents independently selected from J;
wherein up to two aliphatic carbon atoms in R$_2$ and R$_4$ may be replaced by a heteroatom selected from O, NH, S, SO, or SO$_2$ in a chemically stable arrangement;
Z is a carbon atom, —CHR—N—, —HN—CR— or —CHR—CHR—, —O—CHR, —S—CHR, —SO—CHR, —SO$_2$—CHR, or —N—;
wherein R is aliphatic, aryl, aralkyl or cycloalkyl;
R$_5$ is —(C1-C12) aliphatic, wherein any hydrogen is optionally substituted with halogen, and wherein any hydrogen or halogen atom bound to any terminal carbon atom of R$_5$ is optionally substituted with sulfhydryl or hydroxy;
W is selected from: —C(O)OH;

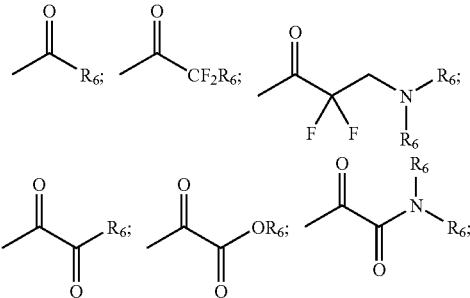

-continued

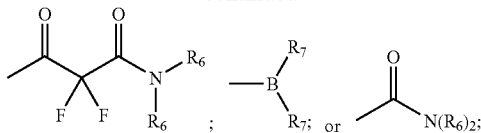

wherein each $R_6$ is independently:
  hydrogen,
  (C1-C12)-aliphatic,
  (C1-C12)-aliphatic-[(C3-C10)-cycloalkyl or -cycloalkenyl],
  (C6-C10)-aryl,
  (C6-C10)-aryl-(C1-C12)aliphatic,
  (C3-C10)-cycloalkyl or -cycloalkenyl,
  (C3-C10)-heterocyclyl,
  (C3-C10)-heterocyclyl-(C1-C12)-aliphatic,
  (C5-C10)hetero aryl, or
  (C5-C10)heteroaryl-(C1-C12)-aliphatic, or
two $R_6$ groups, which are bound to the same nitrogen atom, form together with that nitrogen atom, a (C3-C10)-heterocyclic ring;
wherein $R_6$ is optionally substituted with up to 3 J substituents;
each $R_7$ is hydroxy, alkoxy, or aryloxy; or
each $R_7$ is an oxygen atom linked to an aliphatic group and, together with the boron to which they are each bound, the two $R_7$ groups form a 3-6 membered ring;
V is a bond, —CH($R_8$)—, —N($R_8$)—, —O—, —O—CH($R_8$), —CH($R_8$)—O—, —S—, —S—CH($R_8$)—, —CH($R_8$)—S—, —C(O)—, —C(O)—O—, —O—C(O)—, —C(O)—S—, —C(O)—CHR$_8$—, —CHR$_8$—C(O)—, —N($R_8$)C(O)—, —C(O)N($R_8$)—, —S(O)—, —S(O)—CH($R_8$), —CH($R_8$)—S(O)—, —S(O)N($R_8$)—, —N($R_8$)S(O)—, —S(O)—N($R_8$)—CHR$_8$, —N($R_8$)—S(O)—CHR$_8$—, —CHR$_8$—S(O)$_2$, —S(O)$_2$—CH($R_8$)—, —CH($R_8$)—S(O)$_2$—, —S(O)$_2$N($R_8$)—, —N($R_8$)—S(O)$_2$—, S(O)$_2$—N($R_8$)—CHR$_8$ or —N($R_8$)—S(O)$_2$—CHR$_8$;
wherein $R_8$ is hydrogen or (C1-C12)-aliphatic;
T is selected from:
  (C6-C10)-aryl,
  (C6-C10)-aryl-(C1-C12)aliphatic,
  (C3-C10)-cycloalkyl or -cycloalkenyl,
  (C1-C12)-aliphatic-[(C3-C10)-cycloalkyl or cycloalkenyl],
  (C3-C10)-heterocyclyl,
  (C3-C10)-heterocyclyl-(C1-C12)-aliphatic,
  (C5-C10)heteroaryl, or
  (C5-C10)heteroaryl-(C1-C12)-aliphatic; or
T is selected from:

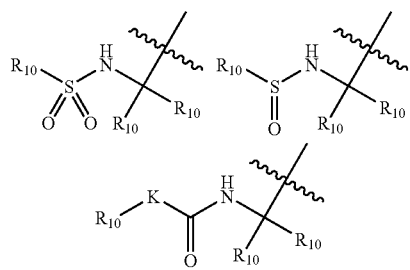

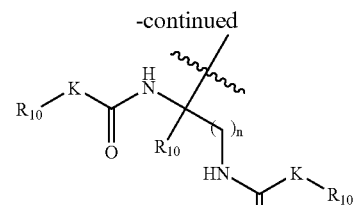

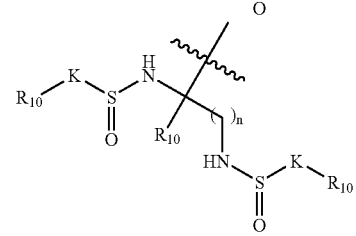

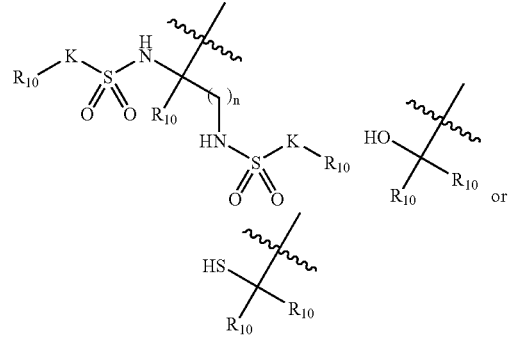

wherein:
  $R_{10}$ is:
    hydrogen,
    (C1-C12)-aliphatic,
    (C1-C12)-aliphatic-[(C3-C10)-cycloalkyl or -cycloalkenyl],
    (C6-C10)-aryl,
    (C6-C10)-aryl-(C1-C12)aliphatic,
    (C3-C10)-cycloalkyl or -cycloalkenyl,
    (C3-C10)-heterocyclyl,
    (C3-C10)-heterocyclyl-(C1-C12)-aliphatic,
    (C5-C10)-heteroaryl, or
    (C5-C10)-heteroaryl-(C1-C12)-aliphatic,
  wherein each T is optionally substituted with up to 3 J substituents;
  K is a bond, (C1-C12)-aliphatic, —O—, —S—, —NR$_9$—, —C(O)—, or —C(O)—NR$_9$—, wherein R$_9$ is hydrogen or (C1-C12)-aliphatic; and
  n is 1-3.

2. The compound according to claim 1, wherein:
  $R_5$ is —(C2-C7)alkyl optionally substituted with halogen;
  $R_2$ and $R_4$ are independently (C1-C12)-aliphatic;
  $R_3$ and $R_1$ are independently —(C1-C10)alkyl, —(C3-C7)cycloalkyl, or —((C1-C6)alkyl)-((C3-C7)cycloalkyl);
  V is a bond, —CH($R_8$)—, —N($R_8$)—, —O—, —O—CH($R_8$), —S—, —S—CH($R_8$), —C(O)—, —C(O)—O—, —C(O)—S—, —C(O)—CHR$_8$—, —C(O)N($R_8$)—, —S(O)—, —S(O)—CH($R_8$)—, —S(O)N($R_8$)—, —S(O)—N($R_8$)—CHR$_8$, —S(O)$_2$, —S—(O)$_2$—CH($R_8$)—, —S(O)$_2$N($R_8$)—, or —S(O)$_2$—N($R_8$)—CHR$_8$;
  wherein $R_8$ is hydrogen or —(C1-C3)alkyl;
  T is —(C6-C10)aryl, —(C5-C10)heteroaryl, —(C3-C6)cycloalkyl, —(C3-C10)heterocyclyl, —(C1-C6)alkyl-(C6-C10)aryl, —(C1-C6)alkyl-(C5-C10)heteroaryl, —(C1-C6)alkyl-(C3-C6)cycloalkyl, —(C1-C6)alkyl- (C3-C10)heterocyclyl, —(C2-C6)alkenyl-(C6-C10)aryl, —(C2-C6)alkenyl-(C5-C10)heteroaryl, —(C2-C6)alkenyl-(C3-C6)cycloalkyl, —(C2-C6)alkenyl-(C3-C10)heterocyclyl,

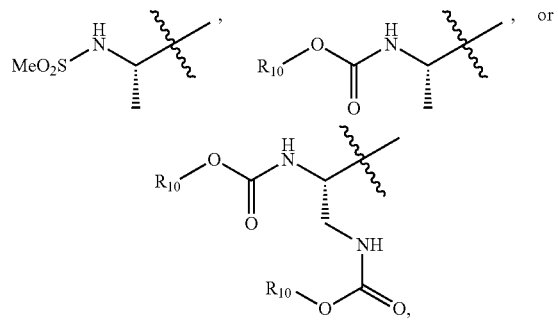

wherein:

R$_{10}$ is —(C1-C4)alkyl;

W is —C(O)OH, —C(O)—C(O)—R$_6$, or —C(O)—C(O)—NH(R$_6$) wherein:

R$_6$ is —(C1-C6)alkyl, —(C6-C10)aryl, —(C3-C6)cycloalkyl, —(C5-C10)heteroaryl, —(C3-C10)heterocyclyl, —NH—((C1-C6)alkyl), —NH—((C3-C6)cycloalkyl), —NH—CH(CH$_3$)-aryl, —NH—CH(CH$_3$)—(C5-C10)heteroaryl or —NH—CH(CH$_3$)—(C3-C10)heterocyclyl, wherein said aryl, heteroaryl, or heterocyclyl is optionally substituted with a suitable electron withdrawing group.

3. The compound according to claim 2, wherein V is —NH—.

4. The compound according to claim 2, wherein V is —C(O)—.

5. The compound according to claim 2, wherein T is a —(C5-C10)heteroaryl.

6. The compound according to claim 5, wherein T is:

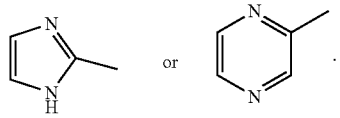

7. The compound according to claim 2, wherein T contains at least one hydrogen bond donor moiety selected from —NH$_2$, —NH—, —OH, and —SH.

8. The compound according to claim 7, wherein T is:

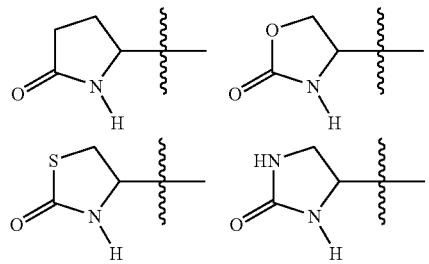

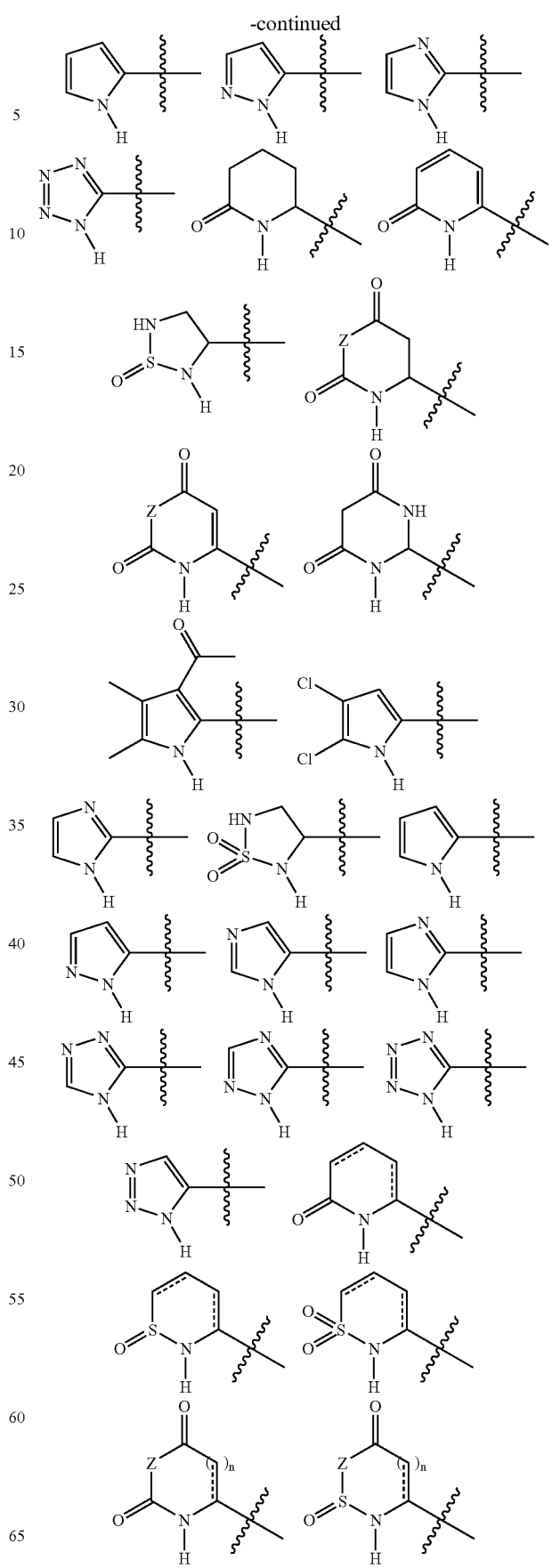

-continued

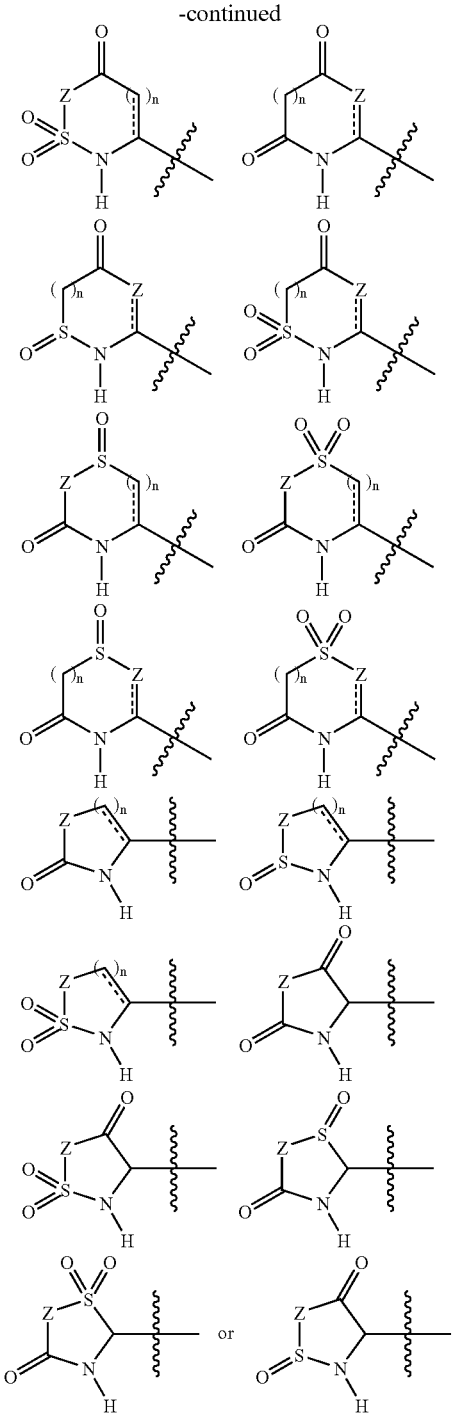

wherein:
T is optionally substituted with up to 3 J substituents, wherein J is halogen, —OR', —NO$_2$, —CF$_3$, —OCF$_3$, —R', oxo, —OR', —O-benzyl, —O-phenyl, 1,2-methylenedioxy, 1,2-ethylenedioxy, —N(R')$_2$, —SR', —SOR', —SO$_2$R', —C(O)R', —COOR' or —CON(R')$_2$, wherein R' independently selected from:
hydrogen,
(C1-C12)-aliphatic,
(C3-C10)-cycloalkyl or -cycloalkenyl,
(C1-C12)-aliphatic-[(C3-C10)-cycloalkyl or -cycloalkenyl],
(C6-C10)-aryl,
(C6-C10)-aryl-(C1-C12)aliphatic,
(C3-C10)-heterocyclyl,
(C6-C10)-heterocyclyl-(C1-C12)aliphatic,
(C5-C10)-heteroaryl, or
(C5-C10)-heteroaryl-(C1-C12)-aliphatic;
Z is independently O, S, NR$_{10}$, or C(R$_{10}$)$_2$;
n is independently 1 or 2; and
----- is independently a single bond or a double bond.

9. The compound according to claim 8, wherein T is:

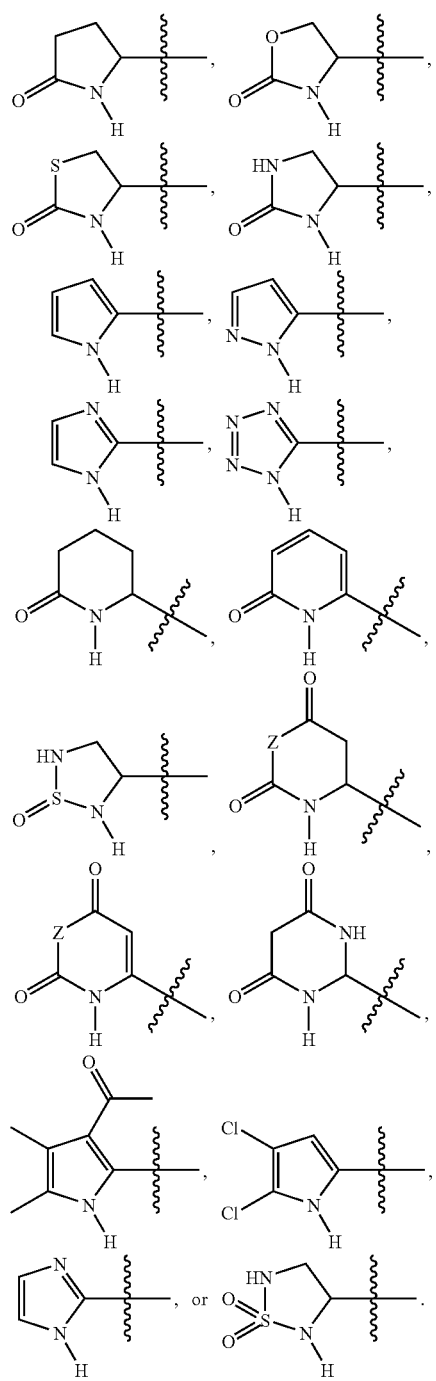

10. The compound according to claim 2, wherein T is:

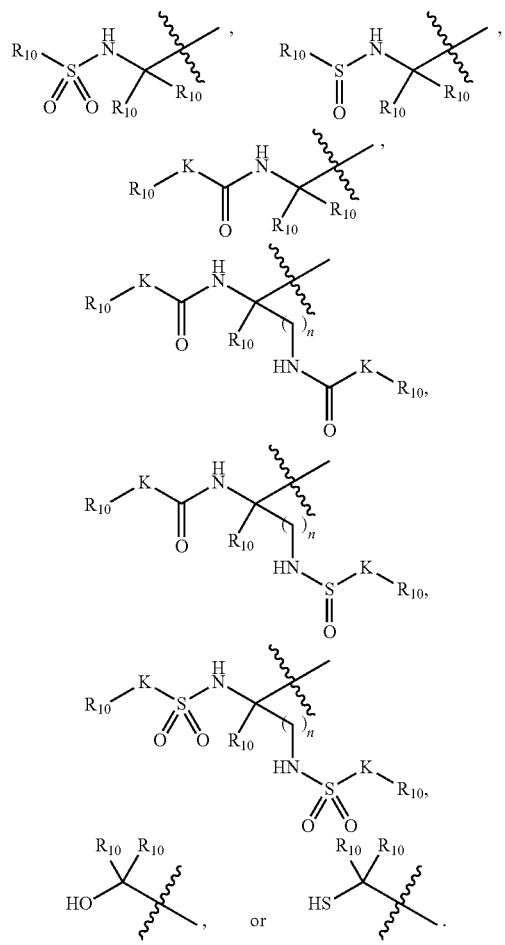

11. The compound according to claim 10, wherein T is:

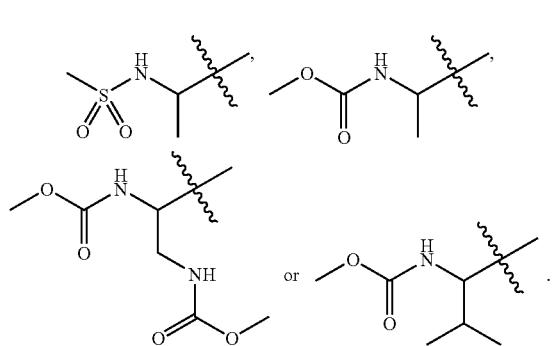

12. The compound according to claim 2, wherein $R_1$ is:

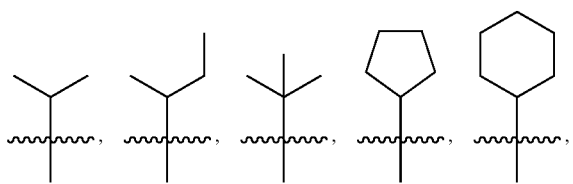

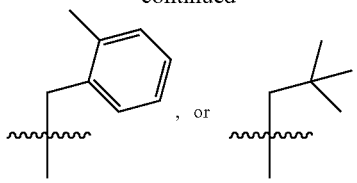

13. The compound according to claim 12, wherein $R_1$ is —$CH_2$—$C(CH_3)_3$, —$C(CH_3)_3$, —$CH(CH_3)_2$, —$CH(CH_3)$—$CH_2$—$CH_3$, or cyclohexyl.

14. The compound according to claim 13, wherein $R_1$ is cyclohexyl.

15. The compound according to claim 2, wherein $R_3$ is:

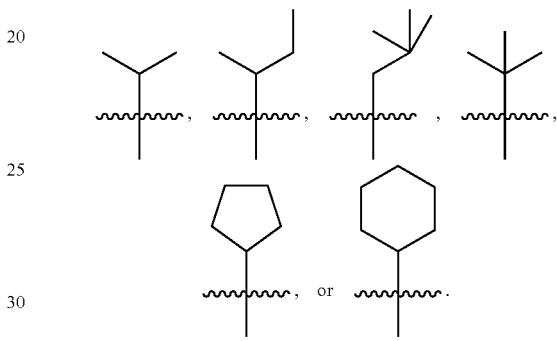

16. The compound according to claim 15, wherein $R_3$ is —$C(CH_3)_3$, —$CH(CH_3)_2$, —$CH(CH_3)$—$CH_2$—$CH_3$, or cyclohexyl.

17. The compound according to claim 16, wherein $R_3$ is —$C(CH_3)_3$ or —$CH(CH_3)_2$.

18. The compound according to claim 2, wherein $R_5$ is:

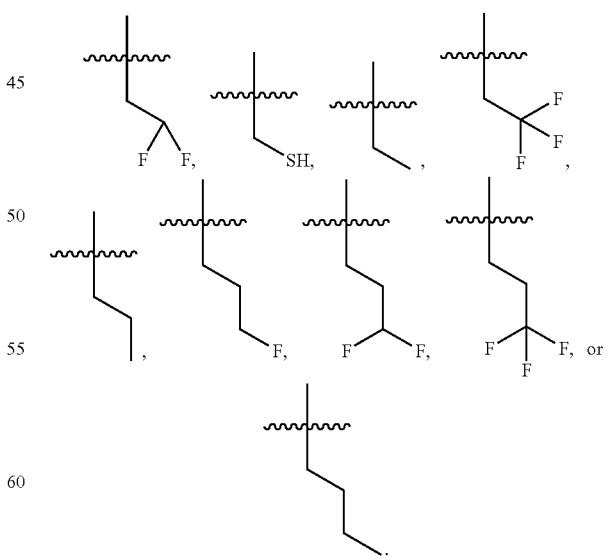

19. The compound according to claim 18, wherein $R_5$ is —$CH_2CH_2CH_3$, —$CH_2CH_2CH_2CH_3$, —$CH_2CH_2CH_2F$, —$CH_2CH_2CHF_2$, or —$CH_2CH_2CF_3$.

20. The compound according to claim 19, wherein $R_5$ is —$CH_2CH_2CH_2CH_3$ or —$CH_2CH_2CHF_2$.

21. The compound according to claim 20, wherein $R_5$ is —$CH_2CH_2CH_2CH_3$.

22. The compound according to claim 2, wherein $R_2$ and $R_4$ are each independently H, methyl, ethyl, or propyl.

23. The compound according to claim 2, wherein W is C(O)—C(O)—NH($R_6$).

24. The compound according to claim 23, wherein in the W, the —NH($R_6$) is —NH—($C_3$-$C_6$ cycloalkyl), —NH—CH(CH$_3$)-aryl, or —NH—CH(CH$_3$)-heterocyclyl, wherein said aryl or said heterocyclyl is optionally substituted with halogen.

25. The compound according to claim 24, wherein in the W, the NH($R_6$) is:

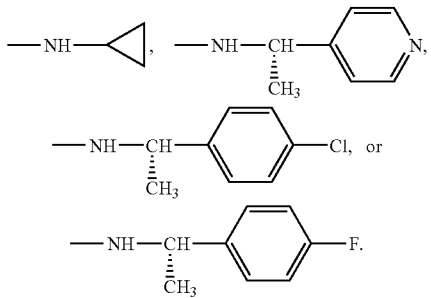

26. A composition comprising a compound according to claim 1 or a pharmaceutically acceptable salt, derivative or prodrug thereof in an amount effective to inhibit a serine protease; and a acceptable carrier, adjuvant or vehicle.

27. The composition according to claim 26, wherein said composition is formulated for administration to a patient.

28. The composition according to claim 27, wherein said composition comprises an additional agent selected from an immunomodulatory agent; an antiviral agent; a second inhibitor of HCV protease; an inhibitor of another target in the HCV life cycle; or combinations thereof.

29. The composition according to claim 28, wherein said immunomodulatory agent is $\tilde{\alpha}$,$\tilde{\beta}$, or γ-interferon; the antiviral agent is ribavirin or amantadine; or the inhibitor of another target in the HCV life cycle is an inhibitor of HCV helicase, polymerase, or metalloprotease.

30. A method of inhibiting the activity of a serine protease comprising the step of contacting said serine protease with a compound according to claim 1.

31. The method according to claim 30, wherein said protease is an HCV NS3 protease.

32. A method of treating an HCV infection in a patient comprising the step of administering to said patient a composition according to claim 27.

33. The method according to claim 32, comprising the additional step of administering to said patient an additional agent selected from an immunomodulatory agent; an antiviral agent; a second inhibitor of HCV protease; an inhibitor of another target in the HCV life cycle; or combinations thereof; wherein said additional agent is selected from an immunomodulatory agent; an antiviral agent; a second inhibitor of HCV protease; an inhibitor of another target in the HCV life cycle; or combinations thereof; and administered to said patient as part of said composition or as a separate dosage form.

34. The method according to claim 33, wherein said immunomodulatory agent is $\tilde{\alpha}$, $\tilde{\beta}$, or γinterferon; said antiviral agent is ribavirin or amantadine; or said inhibitor of another target in the HCV life cycle is an inhibitor of HCV helicase, polymerase, or metalloprotease.

* * * * *